US009963750B2

(12) United States Patent
Kessler et al.

(10) Patent No.: US 9,963,750 B2
(45) Date of Patent: May 8, 2018

(54) HIGH THROUGHPUT METHOD TO GENOTYPE PLANTS

(71) Applicant: COLORADO STATE UNIVERSITY RESEARCH FOUNDATION, Fort Collins, CO (US)

(72) Inventors: Kallie C. Kessler, Denver, CO (US); Eric L. Patterson, Fort Collins, CO (US); Margaret B. Fleming, Fort Collins, CO (US); Todd A. Gaines, Fort Collins, CO (US)

(73) Assignee: Colorado State University Research Foundation, Fort Collins, CO (US)

(*) Notice: Subject to any disclaimer, the term of this patent is extended or adjusted under 35 U.S.C. 154(b) by 0 days. days.

(21) Appl. No.: 15/589,172

(22) Filed: May 8, 2017

(65) Prior Publication Data

US 2017/0327905 A1 Nov. 16, 2017

Related U.S. Application Data

(60) Provisional application No. 62/462,219, filed on Feb. 22, 2017, provisional application No. 62/336,207, filed on May 13, 2016.

(51) Int. Cl.
*C12P 19/34* (2006.01)
*C12Q 1/68* (2018.01)

(52) U.S. Cl.
CPC ......... *C12Q 1/6895* (2013.01); *C12Q 1/6818* (2013.01); *C12Q 2600/13* (2013.01); *C12Q 2600/16* (2013.01)

(58) Field of Classification Search
USPC ................................. 435/6.12, 91.2
See application file for complete search history.

(56) References Cited

U.S. PATENT DOCUMENTS

| | | | |
|---|---|---|---|
| 9,133,509 B2 | 9/2015 | Robinson et al. | |
| 2002/0119891 A1 | 8/2002 | Netherland | |
| 2006/0141495 A1 | 6/2006 | Wu | |
| 2010/0273655 A1 | 10/2010 | Mango | |
| 2013/0067618 A1* | 3/2013 | Ader | A01H 3/04 800/278 |
| 2013/0157858 A1 | 6/2013 | Heilman et al. | |
| 2015/0018213 A1 | 1/2015 | Koschnick | |
| 2015/0218099 A1 | 8/2015 | Mann | |

FOREIGN PATENT DOCUMENTS

| | | |
|---|---|---|
| WO | 2014114189 A1 | 7/2014 |
| WO | 2015126766 A1 | 8/2015 |

OTHER PUBLICATIONS

Grafe, Simon F., et al., "A PCR-RFLP Method to Detect Hybridization between the Invasive Eurasian Watermilfoil (*Myriophyllum spicatum*) and the Native Northern Watermilfoil (*Myriophyllum sibiricum*), and its Application in Ontario Lakes", Botany (2015), 93: pp. 117-121.
Moody, Michael L., et al. "Evidence of Hybridity in Invasive Watermilfoil (*Myriophyllum*) Populations", PNAS (Nov. 12, 2002) vol. 99, No. 23, pp. 14867-14871.
Moody, M.L., et al., "Geographic Distribution and Genotypic Composition of Invasive Hybrid Watermilfoil (*Myriophyllum spicatum* x *M. sibiricum*) Populations in North America", Biol. Invasions (2007) 9: pp. 559-570.
Semagn, Kassa, et al., "Single Nucleotide Polymorphism Genotyping Using Kompetitive Allele Specific PCR (KASP): Overview of the Technology and its Application in Crop Improvement", Mol. Breeding (2014) 33: pp. 1-14.
Sturtevant, Ann P., et al., "Molecular Characterization of Eurasian Watermilfoil, Northern Milfoil, and the Invasive Interspecific Hybrid in Michigan Lakes", J. Aquat. Plant Manage. (2009) 47: pp. 128-135.
Yuan, Jiazheng, et al., "Introduction of High Throughput and Cost Effective SNP Genotyping Platforms in Soybean", Plant Genetics, Genomics, and Biotechnology (2014) 2(1): pp. 90-94.
GenBank Submission: AF513839.1, "Myriophyllum Spicatum Isolate FL36 Internal Transcribed Spacer 1, Partial Sequence; 5.8S Ribosomal RNA Gene, Complete Sequence; and Internal Transcribed Spacer 2, Partial Sequence", 2 pages, Apr. 14, 2009.
GenBank Submission: AF513849.1, "Myriophyllum Spicatum x Myriophyllum Sibiricum Isolate MN51 Internal Transcribed Spacer 2, Partial Sequence", 1 page, Apr. 14, 2009.
GenBank Submission: AF513850.1, "Myriophyllum Spicatum x Myriophyllum Sibiricum Isolate WI18 Internal Transcribed Spacer 2, Partial Sequence", 2 pages, Apr. 14, 2009.
GenBank Submission: DQ786012.1, "Myriophyllum Spicatum Clone 1 Internal Transcribed Spacer 1, Partial Sequence; 5.8S Ribosomal RNA Gene, Complete Sequence; and Internal Transcribed Spacer 2, Partial Sequence", 2 pages, Aug. 11, 2008.
GenBank Submission: DQ786029.1, "Myriophyllum Sibiricum tRNA-Leu (tmL) Gene, Partial Sequence", 2 pages, Aug. 11, 2008.

(Continued)

*Primary Examiner* — Kenneth R Horlick
(74) *Attorney, Agent, or Firm* — McKee, Voorhees & Sease, PLC

(57) ABSTRACT

Methods are provided for high throughput genotyping of plants, utilizing at least three primers, one primer recognizing a polymorphic sequence of a first species of a plant genus, a second primer recognizing a second polymorphic sequence of a second species, and a third primer that recognizes sequences of both the first and second species and producing a measurable signal when amplifying a plant DNA-containing sample. Additional primers recognizing additional species may also be employed. The method may be repeated for multiple sequences each diagnosing a species or hybrid, and results analyzed using data from multiple assays to improve the statistical robustness of genotyping results. Controls are provided in which the primer target sequences are introduced into and extracted from bacteria and the measurable signal used as a control. The methods are particularly useful for genotyping a population of plants, especially where weed species and/or hybrids are present.

23 Claims, 21 Drawing Sheets

(56) References Cited

OTHER PUBLICATIONS

GenBank Submission: FJ426346.1, "Myriophyllum Spicatum Isolate SpicMI1 18S Ribosomal RNA Gene, Partial Sequence; Internal Transcribed Spacer 1, 5.8S Ribosomal RNA Gene, and Internal Transcribed Spacer 2, Complete Sequence; and 26S Ribosomal RNA Gene, Partial Sequence", 2 pages, Oct. 31, 2009.
GenBank Submission: FJ426352.1, "Myriophyllum Sibiricum Isolate SpicMI1 18S Ribosomal RNA Gene, Partial Sequence; Internal Transcribed Spacer 1, 5.8S Ribosomal RNA Gene, and Internal Transcribed Spacer 2, Complete Sequence; and 26S Ribosomal RNA Gene, Partial Sequence", 2 pages, Oct. 31, 2009.
Cuenca, et al., "Assignment of SNP Allelic Configuration in Polyploids Using Competitive Allele-Specific PCR: Application to Citrus Triploid Progeny," Annals of Botany 111, pp. 731-742, published electronically Feb. 18, 2013.
LGC Group, "A Guide to the Analysis of KASP Genotyping Data Using Cluster Plots", https://www.lgcgroup.com/LGCGroup/media/PDFs/Products/Genotyping/Software/Analysis-of-KASP-genotyping-data-using-cluster-plots.pdf?ext=.pdf, 12 pages, accessed online Oct. 20, 2017.
LCG Group, "FAQs Relating to Genotyping", http://www.lgcgroup.com/products/kasp-genotyping-chemistry/faqs/, 4 pages, accessed online Nov. 8, 2017—RNase.
LCG Group, "FAQs Relating to Genotyping", http://www.lgcgroup.com/products/kasp-genotyping-chemistry/faqs/, 4 pages, accessed online Nov. 8, 2017—Controls.
Murphy et al., "A Quantitative Assay for Amaranthus Palmeri Identification", Accepted Article, Pest Management 11 pages (2017).
Colorado State University Research Foundation, PCT/US17/31536 filed Aug. 7, 2017, "Notification of Transmittal of the International Search Report and the Written Opinion of the International Searching Authority, or the Declaration", dated Aug. 7, 2017.
Chown, Steven L. et al., "Biological Invasions, Climate Change and Genomics", Evolutionary Applications, pp. 23-46 published online Dec. 9, 2014.
Gaines, Todd A., et al., "Interspecific Hybridization Transfers a Previously Unknown Glyphosate Resistance Mechanism in *Amaranthus* Species", Evolutionary Applications, pp. 29-38 published online Aug. 23, 2011.

\* cited by examiner

```
Amaranthus_palmeri        ------------------------TCGAAACCTGCCAAGCAGATTGACCAGCGAACAT-GTTTAT   40
Amaranthus_spinosus       ------------------------TCGAAACCTGCCTAGCAGATTGACCAGCGAACATGTTATAT   41
Amaranthus_albus          ------------------------TCGAAACCTGCCTAGCAGATTGACCAGCGAACACGTTTATC   41
Amaranthus_blitoides      ---------AAGGATCATTGTCGAAACCTGCCTAGCAGATTGACCAGCGAACACGTTTATC       52
Amaranthus_arenicola      ------------------------TCGAAACCTGCCTAGCAGATTGACCAGCGAACATGTTTATC   41
Amaranthus_tuberculatus   ACCTGCGCAAGGATCATTGTCGAAACCTGCCTAGCAGATTGACCAGCGAACATGTTTATC       60
Amaranthus_hybridus       ------------------------TCGAAACCTGCCTAGCAGATTGACCAGCGAACATGTTTATC   41
Amaranthus_powellii       ------------------------TCGAAACCTGCCTAGCAGATTGACCAGCGAACATGTTTATC   41
Amaranthus_retroflexus    ------------------------TCGAAACCTGCCTAGCAGATTGACCAGCGAACATGTTTATC   41
                                                  **********  *********************  *

Amaranthus_palmeri        CATACGTGGAGCGGGGTGCCCTAGCGAAGCCTTACGGACGAGCTATTGCACCCTCCTCCC       100
Amaranthus_spinosus       CATACGTGGAGCGGGGTGCCCTAGCGAAGCCTTACGGACGAGCTATTGCCCCTCCTCCC        100
Amaranthus_albus          ATAAGCGGAGCGGGGTGCCCTAGCGAAGCCTTACGGACGAGCTGTTGCCCCCTCCTCCC        101
Amaranthus_blitoides      ATAAGCGGAGCGGGGGTGCCCTAGCGAAGCCTTACGGACGAGCTGTTGCCCCCTCCTCCC       112
Amaranthus_arenicola      ATAAGTGGAGGGGGGTGCCCTAGCGAAGCCTTACGGACGAGCTGTTGCCCCCTCCTCCC        101
Amaranthus_tuberculatus   ATAAGTGGAGGGGGGTGCCCTAGCGAAGCCTTACGGACGAGCTGTTGCCCCCTCCTCCC        120
Amaranthus_hybridus       ATGAGTGGAGCGGGAGCGCCCTAGCGAAGCCTTACGGACGAGCTATTGCCCCCTCCTCCC       101
Amaranthus_powellii       ATGAGTGGAGCGGGAGCGCCCTAGCGAAGCCTTACGGACGAGCTATTGCCCTCTCCTCCC       101
Amaranthus_retroflexus    ATGAGTGGAGCGGGTGCGCCCTAGCGAAGCCTTACGGACGAGCTATTGCCCCCTCCTCCC       101
                              *    **  *  ****************************  **** * *******

Amaranthus_palmeri        AACGTCGGGCGGTGCTCCTTTGTGAGGGGTGCTGCTCGATGCAACAACGAACCCCGGCGC      160
Amaranthus_spinosus       AACGTCGGGCGGTGCTCCTTTGTGAGGGGTGCTGCTCGATGCAACAACGAACCCCGGCGC      161
Amaranthus_albus          GACGTCGGGCGGTGCTCCTCTGCGAGGGGCGCTGCTCGATGCAACAACGAACCCCGGCGC      161
Amaranthus_blitoides      GACGTCGGGCGGTGCTCCTCTGCGAGGGGCGCTGCTCGATGCAACAACGAACCCCGGCGC      172
Amaranthus_arenicola      AACGTCGCGTGGTGCTCCTCTCAGAGGGGTGCTGCTCGATGCAACAACGAACCCCGGCGC      161
Amaranthus_tuberculatus   AACGTCGGGTGGTGCTCCTCTGTGAGGGGTGCTGCTCGATGCAACAACGAACCCCGGCGC      180
Amaranthus_hybridus       AACGTCGGGTGGTGCTCCTTTCTGAGGGGTGCTGCTCGATGCAACAACGAACCCCGGCGC      161
Amaranthus_powellii       AACGTCGGGTGGTGCTCCTTTTTGAGGGGTGCTGCTCGATGCAACAACGAACCCCGGCGC      161
Amaranthus_retroflexus    AACGTCGGGTGGTGCTCCTTTTTGAGGGGTGCTGCTCGATGCAACAACGAACCCCGGCGC      161
                          ********  ******* *   ****** ******************************

Amaranthus_palmeri        GGTCTGCGCCAAGGAACATGAACTTGAGCGTGCTCGTCTCGTGCCCGGGTCCCGGCGCA       220
Amaranthus_spinosus       GGTCTGCGCCAAGGAACATGAACTTGAGCGTGCTCGTCTCGTGCCCGGGTCCCGGCGCA       221
Amaranthus_albus          GGTCTGCGCCAAGGAACATGAACTTGAGCGTGCTCGTCTCGTGCCCGGGTCGCCGGCGCA      221
Amaranthus_blitoides      GGTCTGCGCCAAGGAACATGAACTTGAGCGTGCTCGTCTCGTGCCCGGGTCGCCGGCGCA      232
Amaranthus_arenicola      GGTCTGCGCCAAGGAACATGAACTTGAGCGTGCTCGTCTTGTGCCCGGGTCACCGGCGCA      221
Amaranthus_tuberculatus   GGTCTGCGCCAAGGAACATGAACTTGAGCGTGCTCGTCTTGTGCCCGGGTCACCGGCGCA      240
Amaranthus_hybridus       GGTCTGCGCCAAGGAACATGAACTTGAGCGTGCTCGTCTTGTGCCCGGGTCACCGGCGCA      221
Amaranthus_powellii       GGTCTGCGCCAAGGAACATGAACTTGAGCGTGCTCGTCTTGTGCCCGGGTCACCGGCGCA      221
Amaranthus_retroflexus    GGTCTGCGCCAAGGAACATGAACTTGAGCGTGCTCGTCTTGTGCCCGGGTCACCGGCGCA      221
                          ********************************************** **********  *******

Amaranthus_palmeri        TGGGAGTGGATGCACCCAGTATTGAGTATTAAACGACTCTCGGCAACGGATATCTTGGCT      280
Amaranthus_spinosus       TGGGAGTGAATGCACCCAGTATTGAGTATTAAACGACTCTCGGCAACGGATATCTTGGCT      281
Amaranthus_albus          TGGGAGCGGATGCACCCAATATTGAGTATCAAACGACTCTCGGCAACGGATATCTTGGCT      281
Amaranthus_blitoides      TGGGAGCGGATGCACCCAATATTGAGTATCAAACGACTCTCGGCAACGGATATCTTGGCT      292
Amaranthus_arenicola      TGGGAGTGGATGCACCCAATATTGAGTATTGAACGACTCTCGGCAACGGATATCTTGGCT      281
Amaranthus_tuberculatus   TGGGAGTGGATGCACCCAATATTGAGTATTGAACGACTCTCGGCAACGGATATCTTGGCT      300
Amaranthus_hybridus       TGGGACTCCATGCACCCAATAATGAGTATTAAACGACTCTCGGCAACGGATATCTTGGCT      281
Amaranthus_powellii       TGGGAGTGGATGCACCCAATATTGAGTATTAAACGACTCTCGGCAACGGATATCTTGGCT      281
Amaranthus_retroflexus    TGGGAGTGGATGCACCCAATATTGAGTATTAAACGACTCTCGGCAACGGATATCTTGGCT      281
                          *****   ******** ** ******* ^ *****************************
```

FIG. 6A

```
Amaranthus_palmeri      CTCGCATCGATGAAGAACGTAGCGAAATGCGATACTTGGTGTGAATTGCAGAATCCCGTG   340
Amaranthus_spinosus     CTCGCATCGATGAAGAACGTAGCGAAATGCGATACTTGGTGTGAATTGCAGAATCCCGTG   341
Amaranthus_albus        CTCGCATCGATGAAGAACGTAGCGAAATGCGATACTTGGTGTGAATTGCAGAATCCCGTG   341
Amaranthus_blitoides    CTCGCATCGATGAAGAACGTAGCGAAATGCGATACTTGGTGTGAATTGCAGAATCCCGTG   352
Amaranthus_arenicola    CTCGCATCGATGAAGAACGTAGCGAAATGCGATACTTGGTGTGAATTGCAGAATCCCGTG   341
Amaranthus_tuberculatus CTCGCATCGATGAAGAACGTAGCGAAATGCGATACTTGGTGTGAATTGCAGAATCCCGTG   360
Amaranthus_hybridus     CTCGCATCGATGAAGAACGTAGCGAAATGCGATACTTGGTGTGAATTGCAGAATCCCGTG   341
Amaranthus_powellii     CTCGCATCGATGAAGAACGTAGCGAAATGCGATACTTGGTGTGAATTGCAGAATCCCGTG   341
Amaranthus_retroflexus  CTCGCATCGATGAAGAACGTAGCGAAATGCGATACTTGGTGTGAATTGCAGAATCCCGTG   341
                        ************************************************************

Amaranthus_palmeri      AACCATCGAGTTTTTGAACGCAAGTTGCGCCCGAAGCCTTTGGCCAGGGCACGTCTGCCT   400
Amaranthus_spinosus     AACCATCGAGTTTTTGAACGCAAGTTGCGCCCGAAGCCTTTGGCCAGGGCACGTCTGCCT   401
Amaranthus_albus        AACCATCGAGTTTTTGAACGCAAGTTGCGCCCGAAGCCTTTGGCCAGGGCACGTCTGCCT   401
Amaranthus_blitoides    AACCATCGAGTTTTTGAACGCAAGTTGCGCCCCAAGCCTTTGGCCAGGGCACGTCTGCCT   412
Amaranthus_arenicola    AACCATCGAGTTTTTGAACGCAAGTTGCGCCCGAAGCCTTTGGCCAGGGCACGTCTGCCT   401
Amaranthus_tuberculatus AACCATCGAGTTTTTGAACGCAAGTTGCGCCCGAAGCCTTTGGCCAGGGCACGTCTGCCT   420
Amaranthus_hybridus     AACCATCGAGTTTTTGAACGCAAGTTGCGCCCGAAGCCTTCGGCCAGGGCACGTCTGCCT   401
Amaranthus_powellii     AACCATCGAGTTTTTGAACGCAAGTTGCGCCCGAAGCCTTTGGCCAGGGCACGTCTGCCT   401
Amaranthus_retroflexus  AACCATCGAGTTTTTGAACGCAAGTTGCGCCCGAAGCCTTTGGCCAGGGCACGTCTGCCT   401
                        **************************************** ******************

Amaranthus_palmeri      GGGCGTCACGCAATGCGTCTCCCCCAACCCGCCTAGCTGCGGGAGGGGCGAGGAGGATGG   460
Amaranthus_spinosus     GGGCGTCACGCAATGCGTCTCCCCCAACCCGCCTAGCTGCGGGAGGGGCGAGGAGGATGG   461
Amaranthus_albus        GGGCGTCACGCACTGCGTCTCCCCCAACCCGCCCAGCTGCGGGAGGGGCGAGGAGGATGG   461
Amaranthus_blitoides    GGGCGTCACGCACTGCGTCTCCCCCAACCCGCCCAGCTGCGGGAGGGGCGAGGAGGATGG   472
Amaranthus_arenicola    GGGCGTCACGCACTGCGTCTCCCCCAACCCGCCTAGCTGTGGGAGGGGCGAGGAGGATGG   461
Amaranthus_tuberculatus GGGCGTCACGCACTGCGTCTCCCCCAACCCGCCTAGCTGTGGGAGGGGCGAGGAGGATGG   480
Amaranthus_hybridus     GGGCGTCACGCACTGCGTCTCCCCCAACCCACCTAGCTGTGGGAGGGGCGAGGAGGATGG   461
Amaranthus_powellii     GGGCGTCACGCACTGCGTCTCCCCCAACCCGCCTAGCTGTGGGAGGGGCGAGGAGGATGG   461
Amaranthus_retroflexus  GGGCGTCACGCACTGCGTCTCCCCCAACCCGCCTAGCTGTGGGAGGGGCGAGGAGGATGG   461
                        ************ ******************* ***** * *******************

Amaranthus_palmeri      TCTCCCATGCCTCGCCGGGCGTGGATGGCCTAAAAAGGGAGCCCGCGGTTTCGAGCTGCT   520
Amaranthus_spinosus     TCTCCCATGCCTCGCCGGGCGTGGATGGCCTAAAACAGGAGCCCGCGGTTTCGAGCTGCT   521
Amaranthus_albus        TCTCCCGTGCCTCACCGGGCGTGGATGGCCTAAAACAGGAGCCCACGGTTGCGAGCTGCT   521
Amaranthus_blitoides    TCTCCCGTGCCTCACCGGGCGTGGATGGCCTAAAACAGGAGCCCACGGTTGCGAGCTGCT   532
Amaranthus_arenicola    TCTCCCATGCCTCACCGGGCGTGGATGGCCTAAAACAGGAGCCCACGGTTTCGAGCTGCT   521
Amaranthus_tuberculatus TCTCCCATGCCTCACCGGGCGTGGATGGCCTAAAACAGGAGCCCACGGTTTCGAGCTGCT   540
Amaranthus_hybridus     TCTCCCATGCCTCACCGGGCGTGGATGGCCTAAAACAGGAGCCCACGGTTTCAAGCTGCT   521
Amaranthus_powellii     TCTCCCATGCCTCACCGGGCGTGGATGGCCTAAAACAGGAGCCCACGGTTTCGAGCTGCT   521
Amaranthus_retroflexus  TCTCCCATGCCTCACCGGGCGTGGATGGCCTAAAACAGGAGCCCACGGTTTGAGCTGCT   521
                        ****** ***** ********************* *********  *****   ******

Amaranthus_palmeri      GCGGCGATTGGTGGTGTGCAAGGCCTAGCCTAGAATGCAATCGCGTCGCACAGAGCGTGG   580
Amaranthus_spinosus     GCGGCGATTGGTGGTGTGCAAGGCCTAGCCTAGAATGCAATCGCGTCGCACAGAGCGTGG   581
Amaranthus_albus        GCGGCGATTGGTGGTGTGCAAGGCCTAGCCTAGAATGCAATCGCGTCGCACGGTGCGTGG   581
Amaranthus_blitoides    GCGGCGATTGGTGGTGTGCAAGGCCTAGCCTAGAATGCAATCGCGTCGCACGGTGCGTGG   592
Amaranthus_arenicola    GCGGCGATTGGTGGTGTGCAAGGCCTAGCCTAGAATGCAATCGCGTCGTACAGCGCGTGG   581
Amaranthus_tuberculatus GCGGCGATTGGTGGTGTGCAAGGCCTAGCCTAGAATGCAATCGCGTCGTACAGCGCGTGG   600
Amaranthus_hybridus     GCGGCGATTGGTGGTGTGCAAGGCCTAGCCTAGAATGCAATCGCGTCGCACAGTGCGTTG   581
Amaranthus_powellii     GCGGCGATTGGTGGTGTGCAAGGCCTAGCCTAGAATGCAATCGCGTCGCACAGTGCGTAG   581
Amaranthus_retroflexus  GCGGCGATTGGTGGTGTGCAAGGCCTAGCCTAGAATGCAATCGCGTCGCACAGTGCGTAG   581
                        ************************************************  **  ****  *
```

*FIG. 6B*

```
Amaranthus_palmeri        ACCTTGTGGCCTTGAGGACCCTAGAGCGTTGCCCGAGGGCGACCAACCACT---------  631
Amaranthus_spinosus       ACCTTGTGGCCTCGAGGACCCTAGAGCGTTGCCCGAGGGCGACCAACCACT---------  632
Amaranthus_albus          ACCTTGTGGCCTCGAGGACCCTAGAGTGTTGCCCGAGGGCGACCAACCACT---------  632
Amaranthus_blitoides      ACCTTGTGGCCTCGAGGACCCTAGAGTGTTGCCCGAGGGCGACCAACCACTGCGACCCCA  652
Amaranthus_arenicola      ACCTTGTGGCCTTGAGGACCCTAGAGTGTTGCCCGAGGGCGACCAACCACT---------  632
Amaranthus_tuberculatus   ACCTTGTGGCCTTGAGGACCCTAGAGTGTTGCCCGAGGGCGACCAACCACTGCGACCCCA  660
Amaranthus_hybridus       ACCTTGTGGCCTTGAGGACCCTAGAGCGTTGCCCGAGGGCGACCAACCAAT---------  632
Amaranthus_powellii       ACCTTGTGGCCTTGAGGACCCTAGAGCGTTGCCCGAGGGCGACCAACCACT---------  632
Amaranthus_retroflexus    ACCTTGTGGCCTTGAGGACCCTAGAGCGTTGCCCGAGGGCGACCAACCACT---------  632
                          **********  ************* ************************ *

Amaranthus_palmeri        ------------------------------  631
Amaranthus_spinosus       ------------------------------  632
Amaranthus_albus          ------------------------------  632
Amaranthus_blitoides      GGTCAGGCGGGACTACCCGCTGAGTTTAA    681
Amaranthus_arenicola      ------------------------------  632
Amaranthus_tuberculatus   GGTCAGGCGGGACTACCCGCTGAGTTTAA    689
Amaranthus_hybridus       ------------------------------  632
Amaranthus_powellii       ------------------------------  632
Amaranthus_retroflexus    ------------------------------  632
```

*FIG. 6C*

```
Amaranthus_tuberculatus   ACTAAGCATAATTATTTGGTGTTAGATGTTGAGGATATCCCTAGAATTGTTAAGGAAGCT   696
Amaranthus_palmeri        ACTAAGCATAATTATTTGGTGTTAGATGTTGAGGATATCCCTAGAATTGTTAAGGAAGCT   705
Amaranthus_spinosus       ACTAAGCATAATTATTTGGTGTTAGATGTTGAGGATATCCCTAGAATTGTTAAGGAAGCT   705
Amaranthus_powellii       ACCAAGCATAATTATTTGGTGTTAGATGTTGAGGATATTCCTAGAATTGTTAAGGAAGCT   714
Amaranthus_retroflexus    ACCAAGCATAATTATTTGGTGTTAGATGTTGAGGATATTCCTAGAATTGTTAAGGAAGCT   714
                          ** ***********************************  ********************
```

FIG. 7

```
Amaranthus_tuberculatus    ------------------------ATGGCGTCCACTTCTCAACCACCATTTTCTTCTTTTACTAAA    42
Amaranthus_palmeri         ------------------------ATGGCGTCCACTTCAACAAACCCACCATTTTCCTCTTTTACTAAA   45
Amaranthus_spinosus        ------------------ATGGCGTCCACTTCAACAAACCCACCATTTTCCTCTTTTACTAAA        45
Amaranthus_powellii        CTTCAAGCTTCAACAATGCGTCCACTTCTTCAAACCCACCATTTTCCTCTTTTACTAAA            60
Amaranthus_retroflexus     CTTCAAGCTTCAACAATGGCGTCCACTTCTTCAAACCCACCATTTTCCTCTTTTACTAAA           60
                                                   *  *   *   *   *  ************  ************

Amaranthus_tuberculatus    CCTAACAAAATCCCTAATCTTCAATCCTCCAFTTATGCTCTCCCTTTTTCCAATTCTCTT           102
Amaranthus_palmeri         CCTAACAAAATCCCTAATCTGCAATCATCCAFTTACGCTATCCCTTTTTCCAATTCTCTT           105
Amaranthus_spinosus        CCTAACAAAATCCCTAATCTGCAATCATCCATTTACGCTATCCCTTTTTCCAATTCTCTT           105
Amaranthus_powellii        CCTAACAAAATCCCTAATCTGCAATCATCCATTTACGCTATCCCTTTTTCCAATTCTCTT           120
Amaranthus_retroflexus     CCTAACAAAATCCCTAATCTGCAATCATCCATTTACGCTATCCCTTTTTCCAATTCTCTT           120
                           *******************  ****  *******  *** *** ********************

Amaranthus_tuberculatus    AAACCCGCTTCTT--------CATCTTCAATCCTCCGCCGCCCTCTTCAAATCTCATCATCT        156
Amaranthus_palmeri         AAACCCACTTCTTCTTCTTCTTCTTCAATCCTCCGCCGCCCTCTTCAAATCTCATCATCT          165
Amaranthus_spinosus        AAACCCACTTCTTCTTCTTCTTCTTCAATCCTCCGCCGCCCTCTTCAAATCTCATCATCT          165
Amaranthus_powellii        AAACCCACTTCTT--------CTTCTTCAATCCTCCGCCGCCCTCTTCAAATCTCATCATCT        174
Amaranthus_retroflexus     AAACCCACTTCTT--------CTTCTTCAATCCTCCGCCGCCCTCTTCAAATCTCATCATCT        174
                           ****** ******           * ************************************

Amaranthus_tuberculatus    TCTTCTCAATCACCTAAACCTAAACCTCCTTCCGCTACTATAACTCAATCACCTTCATCT           216
Amaranthus_palmeri         TCTTCTCAATCACCTAAACCTAAACCTCCTTCCGCTACTATAACTCAATCACCTTCATCT           225
Amaranthus_spinosus        TCTTCTCAATCACCTAAACCTAAACCTCCTTCCGCTACTATAACTCAATCACCTTCATCT           225
Amaranthus_powellii        TCTTCTCAATCACCTAAACCTAAACCTCCTTCCGCTACTATAACTCAATCACCTTCGTCT           234
Amaranthus_retroflexus     TCTTCTCAATCACCTAAACCTAAACCTCCTTCCGCTACTATAACTCAATCACCTTCGTCT           234
                           ********************************************************* ***

Amaranthus_tuberculatus    CTCACCGATGATAAACCCTCTTCTTTTGTTTTCCGATTTAGCCCTGATGAACCCAGAAAA           276
Amaranthus_palmeri         CTCACCGATGATAAACCCTCTTCTTTTGTTTCCCGATTTAGCCCTGAAGAACCCAGAAAA           285
Amaranthus_spinosus        CTCACCGATGATAAACCCTCTTCTTTTGTTTCCCGATTTAGCCCTGAAGAACCCAGAAAA           285
Amaranthus_powellii        CTCACCGATGATAAACCCTCTTCTTTTGTTTCCCGATTTAGCCCTGAAGAACCCAGAAAA           294
Amaranthus_retroflexus     CTCACCGATGATAAACCCTCTTCTTTTGTTTCCCGATTTAGTCCTGAAGAACCCAGAAAA           294
                           *******************************  ********  ***** ************

Amaranthus_tuberculatus    GGTTGCGATGTTCTCGTTGAAGCTCTTGAACGTGAAGGTGTTACCGATGTTTTTGCTTAC           336
Amaranthus_palmeri         GGTTGCGATGTTCTCGTTGAAGCTCTTGAACGTGAAGGTGTTACCGATGTTTTTGCTTAC           345
Amaranthus_spinosus        GGTTGCGATGTTCTCGTTGAAGCTCTTGAACGTGAAGGTGTTACCGATGTTTTTGCTTAC           345
Amaranthus_powellii        GGTTGCGATGTTCTCGTTGAAGCTCTTGAACGTGAAGGTGTTACCGATGTTTTTGCTTAC           354
Amaranthus_retroflexus     GGTTGCGATGTTCTCGTTGAAGCTCTTGAACGTGAAGGTGTTACCGATGTTTTTGCTTAC           354
                           ************************************************************

Amaranthus_tuberculatus    CCTGGTGGAGCTTCCATGGAAATCCATCAAGCTCTTACTCGTTCTAATATCATTAGAAAT           396
Amaranthus_palmeri         CCTGGTGGAGCATCCATGGAAATCCATCAAGCTCTTACTCGTTCTAATATCATTAGAAAT           405
Amaranthus_spinosus        CCTGGTGGAGCATCCATGGAAATCCATCAAGCTCTTACTCGTTCTAATATCATTAGAAAT           405
Amaranthus_powellii        CCTGGTGGAGCATCCATGGAAATTCATCAAGCTCTTACTCGTTCTAATATCATTAGAAAT           414
Amaranthus_retroflexus     CCTGGTGGAGCATCCATGGAAATTCATCAAGCTCTTACTCGTTCTAATATCATTAGAAAT           414
                           *********** *********** ************************************

Amaranthus_tuberculatus    GTTCTTCCTCGACATGAACAAGGTGGGGTTTTCGCTGCTGAAGGCTACGCTCGTGCTACT           456
Amaranthus_palmeri         GTTCTTCCTCGACATGAACAAGGTGGGGTTTTCGCTGCTGAAGGCTACGCTCGTGCTACT           465
Amaranthus_spinosus        GTTCTTCCTCGACATGAACAAGGTGGGGTTTTCGCTGCTGAAGGCTACGCTCGTGCTACT           465
Amaranthus_powellii        GTTCTTCCTCGACATGAACAAGGTGGGGTTTTCGCTGCTGAAGGCTACGCTCGTGCTACT           474
Amaranthus_retroflexus     GTTCTTCCTCGACATGAACAAGGTGGGGTTTTCGCTGCTGAAGGCTACGCTCGTGCTACT           474
                           ************************************************************
```

*FIG. 8A*

```
Amaranthus_tuberculatus    GGACGTGTTGGAGTTTGTAATGCCACTTCTGGTCCGGGTGCTACTAATCTTGTTTCCGGT    516
Amaranthus_palmeri         CGACGCCTTGCAGTTTGTAATGCCACTTCTGGTCCAGGTGCTACTAATCTTCTTTCTCGT    525
Amaranthus_spinosus        GGACGCGTTGGAGTTTGTATTGCCACTTCTGGTCCAGGTGCTACTAATCTTGTTTCTCGT    525
Amaranthus_powellii        GGACGCGTTGGAGTTTGTATTGCCACTTCTGGTCCAGGTGCTACTAATCTTGTTTCTCGT    534
Amaranthus_retroflexus     GGACGCGTTGGAGTTTGTATTGCCACTTCTGGTCCAGGTGCTACTAATCTTGTTTCTCGT    534
                           ***** ******* ***** ************** ********************* ***

Amaranthus_tuberculatus    TTTGCTGATGCACTTCTTGACTCAGTCCCGCTTGTCGCCATTACTGGGCAAGTTCCTCGG    576
Amaranthus_palmeri         CTTGCTGATGCACTTCTTGACTCAGTCCCGCTTGTCGCCATTACTGGGCAAGTTCCCCGG    585
Amaranthus_spinosus        CTTGCTGATGCACTTCTTGACTCAGTCCCGCTTGTCGCCATTACTGGGCAAGTTCCCCGG    585
Amaranthus_powellii        CTTGCTGATGCACTTCTTGACTCAGTCCCTCTTGTCGCCATTACTGGGCAAGTTCCCCGG    594
Amaranthus_retroflexus     CTTGCTGATGCACTTCTTGACTCAGTCCCTCTTGTCGCCATTACTGGGCAAGTTCCCCGG    594
                            **************************** ********************* *** ***

Amaranthus_tuberculatus    CGTATGATTGGTACTGATGCTTTTCAAGAGACTCCTATTGTTGAGGTAACTCGATCAATT    636
Amaranthus_palmeri         CGTATGATTGGTACTGATGCTTTTCAAGAGACTCCAATTGTTGAGGTAACTCGATCCATT    645
Amaranthus_spinosus        CGTATGATTGGTACTGATGCTTTTCAAGAGACTCCAATTGTTGAGGTAACTCGATCCATT    645
Amaranthus_powellii        CGTATGATTGGTACTGATGCTTTTCAAGAGACTCCAATTGTTGAGGTAACTCGATCCATT    654
Amaranthus_retroflexus     CGTATGATTGGTACTGATGCTTTTCAAGAGACTCCAATTGTTGAGGTAACTCGATCCATT    654
                           ***********************************  ******************** ***

Amaranthus_tuberculatus    ACTAAGCATAATTATTGGTGTTAGATGTTGAGGATATCCCTAGAATTGTTAAGGAAGCT    696
Amaranthus_palmeri         ACTAAGCATAATTATTGGTGTTAGATGTTGAGGATATTCCTAGAATTGTTAAGGAAGCT    705
Amaranthus_spinosus        ACTAAGCATAATTATTGGTGTTAGATGTTGAGGATATTCCTAGAATTGTTAAGGAAGCT    705
Amaranthus_powellii        ACCAAGCATAATTATTGGTGTTAGATGTTGAGGATATTCCTAGAATTGTTAAGGAAGCT    714
Amaranthus_retroflexus     ACCAAGCATAATTATTGGTGTTAGATGTTGAGGATATTCCTAGAATTGTTAAGGAAGCT    714
                           ** ***************************************** **************

Amaranthus_tuberculatus    TTCTTTTTAGCTAATTCTGGTAGACCTGGACCTGTTTTGATTGATATTCCTAAAGATATT    756
Amaranthus_palmeri         TTCTTTTTAGCTAATTCTGGTAGACCTGGACCTGTTTTGATTGATATTCCTAAAGATATT    765
Amaranthus_spinosus        TTCTTTTTAGCTAATTCTGGTAGACCTGGACCTGTTTTGATTGATATTCCTAAAGATATT    765
Amaranthus_powellii        TTCTTTTTAGCTAATTCTGGTAGACCTGGACCTGTTTTGATTGATATTCCTAAAGATATT    774
Amaranthus_retroflexus     TTCTTTTTAGCTAATTCTGGTAGACCTGGACCTGTTTTGATTGATATTCCTAAAGATATT    774
                           ************************************************************

Amaranthus_tuberculatus    CAGCAACAGTTGGTTGTTCCTAACTGGGAACAGCCCATTAAATTGGGTGGGTATCTTTCT    816
Amaranthus_palmeri         CAGCAACAATTAGTTGTTCCTAATTGGGAACAGCCCATTAAATTGGGTGGGTATCTTTCT    825
Amaranthus_spinosus        CAGCAACAATTAGTTGTTCCTAATTGGGAACAGCCCATTAAATTGGGTGGGTATCTTTCT    825
Amaranthus_powellii        CAGCAACAATTAGTTGTTCCTAATTGGGAACAGCCCATTAAATTGGGTGGGTATCTTTCT    834
Amaranthus_retroflexus     CAGCAACAATTAGTTGTTCCTAATTGGGAACAGCCCATTAAATTGGGTGGGTATCTTTCT    834
                           ********  ** ********** ************************************

Amaranthus_tuberculatus    AGGTTGCCTAAACCCACTTTTTCTGCTAATGAAGAGGGACTTCTTGATCAAATTGTGAGG    876
Amaranthus_palmeri         AGGTTGCCTAAACCCACTTATTCTGCTAATGAAGAGGGACTTCTTGATCAAATTGTAAGG    885
Amaranthus_spinosus        AGGTTGCCTAAACCCACTTATTCTGCTAATGAAGAGGGACTTCTTGATCAAATTGTAAGG    885
Amaranthus_powellii        AGGTTGCCTAAACCCACTTATTCTGCTAATGAAGAGGGACTTCTTGATCAAATTGTAAGG    894
Amaranthus_retroflexus     AGGTTGCCTAAACCCACTTATTCTGCTAATGAAGAGGGACTTCTTGATCAAATTGTAAGG    894
                           ******************* **************************** *** ***

Amaranthus_tuberculatus    TTGGTGGGTGAGTCTAAGAGACCTGTGCTGTATACTGGAGGTGGGTGTTTGAATTCTAGT    936
Amaranthus_palmeri         TTAGTGGGTGAGTCTAAGAGACCTGTGCTGTATACTGGAGGTGGGTGTTTGAATTCTAGT    945
Amaranthus_spinosus        TTAGTGGGTGAGTCTAAGAGACCTGTGCTGTATACTGGAGGTGGGTGTTTGAATTCTAGT    945
```

FIG. 8B

```
Amaranthus_powellii      TTAGTGGGTGAGTCTAAGAGACCTGTGCTGTATACTGGAGGTGGGTGTTTGAATTCTAGT   954
Amaranthus_retroflexus   TTAGTGGGTGAGTCTAAGAGACCTGTGCTGTATACTGGAGGTGGGTGTTTGAATTCTAGT   954
                         ** *********************************************************

Amaranthus_tuberculatus  GAAGAATTGAGGAAATTTGTCAAGTTGACAGGGATTCCGGTTGCTAGTACTTTAATGGGG   996
Amaranthus_palmeri       GAAGAATTGAGGAAATTTGTCGAATTGACAGGGATTCCGGTGGCTAGTACTTTAATGGGG  1005
Amaranthus_spinosus      GAAGAATTGAGGAAATTTGTCGAATTGACAGGGATTCCGGTGGCTAGTACTTTAATGGGG  1005
Amaranthus_powellii      GAAGAATTCAGGAAATTTGTCCAATTCACACGTATTCCCGTGGCTAGTACTTTAATGCGG  1014
Amaranthus_retroflexus   GAAGAATTGAGGAAATTTGTCGAATTGACAGGGTATTCCGGTGGCTAGTACTTTAATGGGG 1014
                         ******** ************ **  ***** ** ****** *****************

Amaranthus_tuberculatus  TTGGGGGCTTTCCCTTGTACTGATGATTTATCACTTCAAATGTTGGGAATGCACGGGACT  1056
Amaranthus_palmeri       TTGGGGGCTTTCCCTTGTACTGATGATTTATCACTTCATATGTTGGGAATGCATGGGACT  1065
Amaranthus_spinosus      TTGGGGGCTTTCCCTTGTACTGATGATTTATCACTTCATATGTTGGGAATGCATGGGACT  1065
Amaranthus_powellii      TTGGGGGCTTTCCCTTGTACTGATGATTTATCTCTTCATATGTTGGGAATGCACGGGACT  1074
Amaranthus_retroflexus   TTGGGGGCTTTCCCTTGTACTGATGATTTATCTCTTCATATGTTGGGAATGCACGGGACT  1074
                         ******************************** **** ************** ******

Amaranthus_tuberculatus  GTGTACGCGAATTACGCGGTGGATAAGGCTGATTTGTTGCTTGCTTCGGCGTTAGGTTT   1116
Amaranthus_palmeri       GTGTACGCGAATTACGCGGTTGATAAGGCCGATTTGTTGCTTGCTTCGGGGTTAGGTTT   1125
Amaranthus_spinosus      GTGTACGCGAATTACGCGGTTGATAAGGCCGATTTGTTGCTTGCTTCGGGGTTAGGTTT   1125
Amaranthus_powellii      GTGTACGCGAATTACGCGGTTGATAAGGCCGATTTGTTGCTTGCTTTTGGGGTTAGGTTT  1134
Amaranthus_retroflexus   GTGTACGCGAATTACGCGGTTGATAAGGCCGATTTGTTGCTTGCTTTTGGGGTTAGGTTT  1134
                         ******************** ******** *************** *  ***********

Amaranthus_tuberculatus  GATGATCGAGTGACTGGGAAGCTCGAGGCGTTTGCTAGCCGGGCTAAGATTGTGCACATC  1176
Amaranthus_palmeri       GATGATCGAGTGACTGGTAAGCTTGAGGCGTTTGCTAGCCGGGCTAAGATTGTGCACATC  1185
Amaranthus_spinosus      GATGATCGAGTGACTGGTAAGCTTGAGGCGTTTGCTAGCCGGGCTAAGATTGTGCACATC  1185
Amaranthus_powellii      GATGATCGAGTGACTGGTAAGCTCGAGGCGTTTGCTAGCCGGGCTAAGATTGTGCACATC  1194
Amaranthus_retroflexus   GATGATCGAGTGACTGGTAAGCTCGAGGCGTTTGCTAGCCGGGCTAAGATTGTGCACATC  1194
                         ***************** ***** ************************************

Amaranthus_tuberculatus  GATATCGACTCTGCTGAAATCGGGAAGAATAAGCAACCTCATGTGTCGATTTGTGGTGAT  1236
Amaranthus_palmeri       GATATCGACTCTGCTGAAATCGGGAAGAATAAGCAACCTCATGTGTCGATTTGTGGTGAT  1245
Amaranthus_spinosus      GATATCGACTCTGCTGAAATCGGGAAGAATAAGCAACCTCATGTGTCGATTTGTGGTGAT  1245
Amaranthus_powellii      GATATCGACTCTGCTGAAATCGGGAAGAATAAGCAACCTCATGTGTCGATTTGTGGTGAT  1254
Amaranthus_retroflexus   GATATCGACTCTGCTGAAATCGGGAAGAATAAGCAACCTCATGTGTCGATTTGTGGTGAT  1254
                         ************************************************************

Amaranthus_tuberculatus  GTTAAAGTGGCATTACGGGGGTTGAATAATATTTTGGAATCTAGAAAAGGAAAGGTGAAA  1296
Amaranthus_palmeri       GTTAAAGTGGCATTACAGGGTTTGAATAAGATTTTGGAATCTAGAAAAGGAAAGCTGAAA  1305
Amaranthus_spinosus      GTTAAAGTGGCATTACAGGGTTTGAATAAGATTTTGGAATCTAGAAAAGGAAAGCTGAAA  1305
Amaranthus_powellii      GTTAAAGTGGCATTACAGGGGTTGAATAAGATTTTGGAATCTAGAAAAGGAAAGCTGAAA  1314
Amaranthus_retroflexus   GTTAAAGTGGCATTACAGGGGTTGAATAAGATTTTGGAATCTAGAAAAGGAAAGCTGAAA  1314
                         **************** *** ******* *******************************

Amaranthus_tuberculatus  TTGGATTTCTCTAATTGGAGGGAGGAATTGAATGAGCAGAAAAGAAGTTTCCTTTGAGT  1356
Amaranthus_palmeri       TTGGATTTCTCTAATTGGAGGGAGGAGTTGAATGAGCAGAAAAGAAGTTTCCTTTAAGT  1365
Amaranthus_spinosus      TTGGATTTCTCTAATTGGAGGGAGGAGTTGAATGAGCAGAAAAGAAGTTTCCTTTAAGT  1365
Amaranthus_powellii      CTGGATTTCTCTAATTGGAGGGAGGAGTTGAATGAGCAGAAAAGAAGTTTCCTTTGAGT  1374
Amaranthus_retroflexus   TTCGATTTCTCTAATTGGACGCAGCAGTTGAATCAGCACAAAAGAAGTTTCCTTTCAGT  1374
                         *  **************** *  *  ******* **** ***************  ***
```

FIG. 8C

```
Amaranthus_tuberculatus    TTTAAGACTTTCGGGGATGCAATTCCTCCGCAATATGCCATTCAGGTTCTGGACGAGTTA    1416
Amaranthus_palmeri         TTTAAGACTTTCGGGGATGCAATTCCTCCGCAATACGCCATTCAGGTTCTTGACGAGTTG    1425
Amaranthus_spinosus        TTTAAGACTTTCGGGGATGCAATTCCTCCGCAATACGCCATTCAGGTTCTTGACGAGTTG    1425
Amaranthus_powellii        TTTAACACTTTCGGGCATCCAATTCCTCCCCAATACCCCATTCAGCTTCTTGACCAGTTG    1434
Amaranthus_retroflexus     TTTAAGACTTTCGGGGATGCAATTCCTCCGCAATACGCCATTCAGGTTCTTGACGAGTTG    1434
                           ***** ******* ** ** ********* ***** ******** ***** *** *****

Amaranthus_tuberculatus    ACGAAGGGTGATGCGATTGTAAGTACCGGTGTTGGGCAGCACCAAATGTGGGCTGCCCAA    1476
Amaranthus_palmeri         ACGAAGGGTGATGCGGTTGTAAGTACCGGTGTTGGGCAGCACCAAATGTGGGCTGCCCAA    1485
Amaranthus_spinosus        ACGAAGGGTGATGCGGTTGTAAGTACCGGTGTTGGGCAGCACCAAATGTGGGCTGCCCAA    1485
Amaranthus_powellii        ACGAAGGGCGATGCGGTTGTAAGTACTGGTGTTGGGCAGCACCAAATGTGGGCTGCCCAA    1494
Amaranthus_retroflexus     ACGAAGGGCGATGCGGTTGTAAGTACTGGTGTTGGGCAGCACCAAATGTGGGCTGCCCAA    1494
                           ******** ****** ********** ******* *************************

Amaranthus_tuberculatus    TTTTATAAGTACCGAAATCCTCGCCAATGGCTGACCTCGGGTGGTTTGGGGGCTATGGGG    1536
Amaranthus_palmeri         TTCTATAAGTACCGAAATCCTCGCCAATGGCTGACCTCGGCTGGTTTGGGGGCTATGGGG    1545
Amaranthus_spinosus        TTCTATAAGTACCGAAATCCTCGCCAATGGCTGACCTCGGGTGGTTTGGGGGCTATGGGG    1545
Amaranthus_powellii        TTCTATAAGTACCGAAATCCTCGCCAATGGCTGACCTCGGGTGGTTTGGGGGCTATGGGG    1554
Amaranthus_retroflexus     TTCTATAAGTACCGAATCCTCGCCAATGGCTGACCTCGGTGGTTTGGGGGCTATGGGG    1554
                           ** ************ ** ******************** ********************

Amaranthus_tuberculatus    TTTGGTCTACCAGCCGCTATTGGAGCTGCTGTTGCTCGACCAGATGCGGTGGTTGTAGAC    1596
Amaranthus_palmeri         TTTGGTCTACCAGCTGCTATTGGAGCTGCTGTTGCTCGACCAGATGCGGTGGTTGTAGAC    1605
Amaranthus_spinosus        TTTGGTCTACCAGCTGCTATTGGAGCTGCTGTTGCTCGACCAGATGCGGTGGTTGTAGAC    1605
Amaranthus_powellii        TTTGGTCTACCAGCTGCTATTGGAGCTGCTGTTGCTCGACCAGATGCGGTGGTTGTAGAC    1614
Amaranthus_retroflexus     TTTGGTCTACCAGCTGCTATTGGAGCTGCTGTTGCTCGACCAGATGCGGTGGTTGTAGAC    1614
                           ************** *********************************************

Amaranthus_tuberculatus    ATTGATGGGGACGGGAGTTTATCATGAATGTTCAAGAGTTGGCTACGATTAGGGTGGAG    1656
Amaranthus_palmeri         ATTGATGGGGATGGGAGTTTATCATGAATGTTCAAGAGTTGGCTACGATTAGGGTGGAG    1665
Amaranthus_spinosus        ATTGATGGGGATGGGAGTTTTATCATGAATGTTCAAGAGTTGGCTACGATTAGGGTGGAG    1665
Amaranthus_powellii        ATTGATGGGGATGGGAGTTTCATCATGAATGTTCAAGAGTTGGCTACGATTAGGGTAGAG    1674
Amaranthus_retroflexus     ATTGATGGGGATGGGAGTTTTATCATGAATGTTCAAGAGTTGGCTACGATTAGGGTAGAG    1674
                           *********** ******** *********************************  ***

Amaranthus_tuberculatus    AATCTCCCGGTTAAAATCATGCTCTTGAACAATCAACATTTAGGTATGGTTGTTCAATGG    1716
Amaranthus_palmeri         AATCTCCCGGTTAAAATCATGCTCTTGAACAATCAACATTTAGGTATGGTTGTTCAATTG    1725
Amaranthus_spinosus        AATCTCCCGGTTAAAATCATGCTCTTGAACAATCAACATTTAGGTATGGTTGTTCAATTG    1725
Amaranthus_powellii        AATCTCCCGGTTAAAATCATGCTCTTGAACAATCAACATTTAGGTATGGTTGTTCAATGG    1734
Amaranthus_retroflexus     AATCTCCCGGTTAAAATCATGCTCTTGAACAATCAACATTTAGGTATGGTTGTTCAATGG    1734
                           *********************************************************  *

Amaranthus_tuberculatus    GAAGATCGATTTTACAAAGCTAACCGGGCACATACATACCTCGGRAATCCNTCCAATTCT    1776
Amaranthus_palmeri         GAAGATCGATTTTACAAAGCTAACCGGGCACATACATACCTCGGGAATCCTTCCAATTCT    1785
Amaranthus_spinosus        GAAGATCGATTTACAAAGCTAACCGGGCACATACATACCTCGGGAATCCTTCCAATTCT    1785
Amaranthus_powellii        GAAGATCGATTTTACAAAGCTAACCGGGCACATACATACCTCGGGAATCCTTCCAATTCT    1794
Amaranthus_retroflexus     GAAGATCGATTTTACAAAGCTAACCGGGCACATACATACCTCGGGAATCCTTCCAATTCT    1794
                           ************ ******************************** ***** ********

Amaranthus_tuberculatus    TCMGAAATCTTCCCGGATATGCTSAAATTTGCTGAAGCATGTGATATACCAGCAGCCCGT    1836
Amaranthus_palmeri         TCCGAAATCTTCCCGGATATGCTCAAATTCGCTGAAGCATGTGATATACCAGCAGCTCGT    1845
Amaranthus_spinosus        TCCGAAATCTTCCCGGATATGCTCAAATTCGCTGAAGCATGTGATATACCAGCAGCTCGT    1845
Amaranthus_powellii        TCCGAAATCTTCCCGGATATGCTCAAATTTGCTGAAGCATGTGATATACCAGCAGCCCGT    1854
Amaranthus_retroflexus     TCCGAAATCTTCCCGGATATGCTCAAATTTGCTGAAGCATGTGATATACCAGCAGCCCGT    1854
                           ** ******************** ***** ************************** ***
```

*FIG. 8D*

```
Amaranthus_tuberculatus    GTTACCAAGGTGAGCGATTTAAGGGCTGCAATTCAAACAATGTTGGATACTCCAGGACCA    1896
Amaranthus_palmeri         GTTACCAAGGTGAGCGATTTAAGGGCTGCAATTCAAACAATGTTGGATACTCCAGGACCG    1905
Amaranthus_spinosus        GTTACCAAGGTGAGCGATTTAAGGGCTGCAATTCAAACAATGTTGGATACTCCAGGACCG    1905
Amaranthus_powellii        GTTACCAAGGTGAGCGATTTAAGGACTGCAATTCAAACAATGTTGGATACTCCAGGACCG    1914
Amaranthus_retroflexus     GTTACCAAGGTGAGCGATTTAAGGGCTGCAATTCAAACAATGTTGGATACTCCAGGACCG    1914
                           *********************** ************************************

Amaranthus_tuberculatus    TATCTGCTGGATGTAATCGTACCACATCAGGAGCATGTGCTGCCTATGATCCCTAGCGGT    1956
Amaranthus_palmeri         TATCTGCTGGATGTAATCGTACCACATCAGGAGCATGTGCTGCCTATGATCCCTAGCGGT    1965
Amaranthus_spinosus        TATCTGCTGGATGTAATCGTACCACATCAGGAGCATGTGCTGCCTATGATCCCTAGCGGT    1965
Amaranthus_powellii        TATCTGCTGGATGTAATCGTACCACATCAGGAGCATGTCCTGCCTATGATCCCTAGCGGT    1974
Amaranthus_retroflexus     TATCTGCTGGATGTAATCGTACCACATCAGGAGCATGTGCTGCCTATGATCCCTAGCGGT    1974
                           ************************************** *********************

Amaranthus_tuberculatus    GCCGCCTTCAAGGACACCATCACAGAGGGTGATGGAAGAAGGGCTTATTAG---------    2007
Amaranthus_palmeri         GCCGCCTTCAAGGACACCATCACAGAGGGTGATGGAAGAAGGGC----------------    2009
Amaranthus_spinosus        GCCGCCTTCAAGGACACCATCACAGAGGGTGATGGAAGAAGGGC----------------    2009
Amaranthus_powellii        GCCGCCTTCAAGGACACCATAACAGAGGGTGATGGAAGAAGGGCTTATTAGTTCGTTGGA    2034
Amaranthus_retroflexus     GCCGCCTTCAAGGACACCATAACAGAGGGTGATGGAAGAAGGGCTTATTAGTTCGTTGGA    2034
                           ******************** *********************

Amaranthus_tuberculatus    -------------------------------              2007
Amaranthus_palmeri         -------------------------------              2009
Amaranthus_spinosus        -------------------------------              2009
Amaranthus_powellii        GATCCTTATAGAGGAGAAGCTTTTTGTAGGA               2065
Amaranthus_retroflexus     GATCCTTATAGAGGAGAAGCTTTTTGTAGGA               2065
```

*FIG. 8E*

SEQUENCE LISTING

```
<160> NUMBER OF SEQ ID NOS: 47

<210> SEQ ID NO 1
<211> LENGTH: 22
<212> TYPE: DNA
<213> ORGANISM: Artificial Sequence
<220> FEATURE:
<223> OTHER INFORMATION: Forward Primer ITS Region

<400> SEQUENCE: 1
ggaagtaaaa gtcgtaacaa gg                                              22

<210> SEQ ID NO 2
<211> LENGTH: 20
<212> TYPE: DNA
<213> ORGANISM: Artificial Sequence
<220> FEATURE:
<223> OTHER INFORMATION: Primer Reverse

<400> SEQUENCE: 2
tcctccgctt attgatatgc                                                 20

<210> SEQ ID NO 3
<211> LENGTH: 753
<212> TYPE: DNA
<213> ORGANISM: Myriophyllum spictum

<400> SEQUENCE: 3
ggaagtaaaa gtcgtaacaa ggtttccgta ggtgaacctg cggaaggatc attgtcgaaa      60
cctgcacagc agaacgaccc gtgaactaat aaacacccgg ggggagagga gggagctgca     120
cttgtgcggc gccacccctc gcccccagt gcctagacgc gccccctgcc acaccggact      180
ttgttcggcg tcggcaggag gtcgtccatg gcgacaataa caaacccgg cgcggaaagc      240 gccaaggaaa tcatgacgaa cttagcacac cactagccga cttgtgcggc agcggcgttg     300
caaacttcga tacctaaacg actctcggca acggatatct cggctctcgc atcgatgaag     360
```

```
aacgtagcga aatgcgatac ttggtgtgaa ttgcagaatc ccgtgaacca tcgagttttt    420
gaacgcaagt tgcgcccgaa gccattcggc cgagggcacg tctgcctggg cgtcacgtat    480
cgcgttgctc ccaaagccca cccttcaagg ataaggcgct gcggaagcag atattggcct    540
cccgtgcctg cgcacggctg gcctaaatgc aagcctgggg gtgacgaaag ggtcacgaca    600
agcggtggtt gataactcag cctttgttgc gccgtgcccg ccgtgcccct tggagctcag    660
catccccgac gcgccgtctc gacggcgttt gcatcgcgac cccaggtcag gcgggactac    720
ccgctgagtt taagcatatc aataagcgga gga                                 753

<210> SEQ ID NO 4
<211> LENGTH: 751
<212> TYPE: DNA
<213> ORGANISM: Myriophyllum sibiricum

<400> SEQUENCE: 4
ggaagtaaaa gtcgtaacaa ggtttccgta ggtgaacctg cggaaggatc attgtcgaaa     60
cctgcacagc agaacgacct gtgaactaat aaacacccgg ggggcgagga gggagctgca    120
cttgtgcggc accacccctt gccccccagt gcctagacgc ccccctgcca caccggactt    180
gttcggcgtc ggcaggaggt cgtccgtggc gacaataaca aaccccggcg cggaaagcgc    240
caaggaaatc atgacgaact tagcacaccg ctagccgact tgtgcggcag cggcgttgca    300
aacttcgata cctaaacgac tctcggcaac ggatatctcg gctctcgcat cgatgaagaa    360
cgtagcgaaa tgcgatactt ggtgtgaatt gcagaatccc gtgaaccatc gagtttttga    420
acgcaagttg cgcccgaagc cattcggccg agggcacgtc tgcctgggcg tcacgtatcg    480
cgttgctccc aaagcccacc cttcaaggat atggtgctgc ggaagcagat attggcctcc    540
cgtgcctgtg cacggatggc ctaaatgcaa gcctgggggt gacgaaaggg tcacgacaag    600
cggtggttga taactcagcc tttgttgcgt cgtgcccgcc gtgccccttg gagctcagca    660
tccccgacgc gctgtctcga cggcgtttgc atcgcgaccc caggtcaggc gggactaccc    720
gctgagttta agcatatcaa taagcggagg a                                   751

<210> SEQ ID NO 5
<211> LENGTH: 163
<212> TYPE: DNA
<213> ORGANISM: Artificial Sequence
<220> FEATURE:
<223> OTHER INFORMATION: Vector control 1

<400> SEQUENCE: 5
catgacgaac ttagcacacc gctagccgac ttgtgcggca gcggcgttgc aaacttcgat     60
acctacaaag cccacccttc aaggatatgg tgctgcggaa gcagatattg gataactcag    120
cctttgttgc gtcgtgcccg ccgtgcccct tggagctcag cat                      163

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
catgacgwac ttagcacacc g                                               21

<210> SEQ ID NO 7
```

```
<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
catgacgaac ttagcacacc a                                            21

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
taggtatcga agtttgcaac gc                                           22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
caatatctgc ttccgcagca                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
caatatctgc ttccgcagcg                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
caaagcccac ccttcaagga                                              20

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gataactcag cctytgttgc gt                                           22

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
```

```
gataactcag cctttgttgc gc                                              22

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
atgctgagct ccaaggggca                                                 20

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gaaggtgacc aagttcatgc t                                               21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
gaaggtcgga gtcaacggat t                                               21

<210> SEQ ID NO 17
<211> LENGTH: 631
<212> TYPE: DNA
<213> ORGANISM: Amaranthus palmeri

<400> SEQUENCE: 17
tcgaaacctg ccaagcagat tgaccagcga acatgtttat catacgtgga gcggggtgcc     60
ctagcgaagc cttacggacg agctattgca ccctcctccc aacgtcgggc ggtgctcctt    120
tgtgaggggt gctgctcgat gcaacaacga accccggcgc ggtctgcgcc aaggaacatg    180
aacttgagcg tgctcgtctc gtgcccgggt ccccggcgca tgggagtgga tgcacccagt    240
attgagtatt aaacgactct cggcaacgga tatcttggct ctcgcatcga tgaagaacgt    300
agcgaaatgc gatacttggt gtgaattgca gaatcccgtg aaccatcgag tttttgaacg    360
caagttgcgc ccgaagcctt tggccagggc acgtctgcct gggcgtcacg caatgcgtct    420
cccccaaccc gctagctgc gggaggggcg aggaggatgg tctcccatgc ctcgccgggc    480
gtggatggcc taaaaaggga gcccgcggtt tcgagctgct gcggcgattg gtggtgtgca    540
aggcctagcc tagaatgcaa tcgcgtcgca cagagcgtgg accttgtggc cttgaggacc    600
ctagagcgtt gcccgagggc gaccaaccac t                                  631

<210> SEQ ID NO 18
<211> LENGTH: 632
<212> TYPE: DNA
<213> ORGANISM: Amaranthus spinosus

<400> SEQUENCE: 18
tcgaaacctg cctagcagat tgaccagcga acatgttata tcatacgtgg agcggggtgc     60
```

```
cctagcgaag ccttacggac gagctattgc cccctcctcc caacgtcggg cggtgctcct      120
ttgtgagggg tgctgctcga tgcaacaacg aaccccggcg cggtctgcgc caaggaacat      180
gaacttgagc gtgctcgtct cgtgcccggg tccccggcgc atgggagtga atgcacccag      240
tattgagtat taaacgactc tcggcaacgg atatcttggc tctcgcatcg atgaagaacg      300
tagcgaaatg cgatacttgg tgtgaattgc agaatcccgt gaaccatcga gttttttgaac     360 gcaagttgcg cccgaagcct ttggccaggg cacgtctgcc tgggcgtcac gcaatgcgtc      420
tcccccaacc cgcctagctg cgggaggggc gaggaggatg gtctcccatg cctcgccggg      480
cgtggatggc ctaaaacagg agcccgcggt ttcgagctgc tgcggcgatt ggtggtgtgc      540
aaggcctagc ctagaatgca atcgcgtcgc acagagcgtg gaccttgtgg cctcgaggac      600
cctagagcgt tgcccgaggg cgaccaacca ct                                    632

<210> SEQ ID NO 19
<211> LENGTH: 632
<212> TYPE: DNA
<213> ORGANISM: Amaranthus albus

<400> SEQUENCE: 19
tcgaaacctg cctagcagat tgaccagcga acacgtttat cataagcgga gcggggtgc       60 cctagcgaag ccttacggac gagctgttgc cccctcctcc cgacgtcggg cggtgctcct      120
ctgcgagggg cgctgctcga tgcaacaacg aaccccggcg cggtctgcgc caaggaacat      180
gaacttgagc gtgctcgtct cgtgcccggg tcgccggcgc atgggagcgg atgcacccaa      240
tattgagtat caaacgactc tcggcaacgg atatcttggc tctcgcatcg atgaagaacg      300
tagcgaaatg cgatacttgg tgtgaattgc agaatcccgt gaaccatcga gttttttgaac     360 gcaagttgcg cccgaagcct ttggccaggg cacgtctgcc tgggcgtcac gcactgcgtc      420
tcccccaacc cgcccagctg cgggaggggc gaggaggatg gtctcccgtg cctcaccggg      480
cgtggatggc ctaaaacagg agcccacggt tgcgagctgc tgcggcgatt ggtggtgtgc      540
aaggcctagc ctagaatgca atcgcgtcgc acggtgcgtg gaccttgtgg cctcgaggac      600
cctagagtgt tgcccgaggg cgaccaacca ct                                    632

<210> SEQ ID NO 20
<211> LENGTH: 652
<212> TYPE: DNA
<213> ORGANISM: Amaranthus blitoides

<400> SEQUENCE: 20
aaggatcatt gtcgaaacct gcctagcaga ttgaccagcg aacacgttta tcataagcgg      60
agcgggggtg ccctagcgaa gccttacgga cgagctgttg cccccctcctc ccgacgtcgg    120 gcggtgctcc tctgcgaggg gcgctgctcg atgcaacaac gaaccccggc gcggtctgcg     180
ccaaggaaca tgaacttgag cgtgctcgtc tcgtgcccgg gtcgccggcg catgggagcg     240
gatgcaccca atattgagta tcaaacgact ctcggcaacg gatatcttgg ctctcgcatc     300
gatgaagaac gtagcgaaat gcgatacttg gtgtgaattg cagaatcccg tgaaccatcg     360 agttttttgaa cgcaagttgc gcccgaagcc tttggccagg gcacgtctgc ctgggcgtca    420
cgcactgcgt ctcccccaac ccgcccagct gcgggagggg cgaggaggat ggtctcccgt     480
gcctcaccgg gcgtggatgg cctaaaacag gagcccacgg ttgcgagctg ctgcggcgat     540
tggtggtgtg caaggcctag cctagaatgc aatcgcgtcg cacggtgcgt ggaccttgtg     600
gcctcgagga ccctagagtg ttgcccgagg gcgaccaacc actgcgaccc ca             652
```

<210> SEQ ID NO 21
<211> LENGTH: 632
<212> TYPE: DNA
<213> ORGANISM: Amaranthus arenicola

<400> SEQUENCE: 21

| | | | | | |
|---|---|---|---|---|---|
| tcgaaacctg | cctagcagat | tgaccagcga | acatgtttat | cataagtgga | gggggggtgc | 60 |
| cctagcgaag | ccttacggac | gagctgttgc | cccctcctcc | caacgtcggg | tggtgctcct | 120 |
| ctcagagggg | tgctgctcga | tgcaacaacg | aaccccggcg | cggtctgcgc | caaggaacat | 180 |
| gaacttgagc | gtgctcgtct | tgtgcccggg | tcaccggcgc | atgggagtgg | atgcacccaa | 240 |
| tattgagtat | tgaacgactc | tcggcaacgg | atatcttggc | tctcgcatcg | atgaagaacg | 300 |
| tagcgaaatg | cgatacttgg | tgtgaattgc | agaatcccgt | gaaccatcga | gttttgaac | 360 |
| gcaagttgcg | cccgaagcct | ttggccaggg | cacgtctgcc | tgggcgtcac | gcactgcgtc | 420 |
| tcccccaacc | cgcctagctg | tgggaggggc | gaggaggatg | tctcccatg | cctcaccggg | 480 |
| cgtggatggc | ctaaaacagg | agcccacggt | ttcgagctgc | tgcggcgatt | ggtggtgtgc | 540 |
| aaggcctagc | ctagaatgca | atcgcgtcgt | acagcgcgtg | gaccttgtgg | ccttgaggac | 600 |
| cctagagtgt | tgcccgaggg | cgaccaacca | ct | | | 632 |

<210> SEQ ID NO 22
<211> LENGTH: 689
<212> TYPE: DNA
<213> ORGANISM: Amaranthus tuberculatus

<400> SEQUENCE: 22

| | | | | | |
|---|---|---|---|---|---|
| acctgcggaa | ggatcattgt | cgaaacctgc | ctagcagatt | gaccagcgaa | catgtttatc | 60 |
| ataagtggag | gggggtgcc | ctagcgaagc | cttacggacg | agctgttgcc | ccctcctccc | 120 |
| aacgtcgggt | ggtgctcctc | tctgagggg | gctgctcgat | gcaacaacga | accccggcgc | 180 |
| ggtctgcgcc | aaggaacatg | aacttgagcg | tgctcgtctt | gtgcccgggt | caccggcgca | 240 |
| tgggagtgga | tgcacccaat | attgagtatt | gaacgactct | cggcaacgga | tatcttggct | 300 |
| ctcgcatcga | tgaagaacgt | agcgaaatgc | gatacttggt | gtgaattgca | gaatcccgtg | 360 |
| aaccatcgag | tttttgaacg | caagttgcgc | ccgaagcctt | tggccagggc | acgtctgcct | 420 |
| gggcgtcacg | cactgcgtct | cccccaaccc | gcctagctgt | gggaggggcg | aggaggatgg | 480 |
| tctcccatgc | tcaccgggc | gtggatggcc | taaaacagga | gcccacggtt | tcgagctgct | 540 |
| gcggcgattg | gtggtgtgca | aggcctagcc | tagaatgcaa | tcgcgtcgta | cagcgcgtgg | 600 |
| accttgtggc | cttgaggacc | ctagagtgtt | gcccgagggc | gaccaaccac | tgcgacccca | 660 |
| ggtcaggcgg | gactacccgc | tgagtttaa | | | | 689 |

<210> SEQ ID NO 23
<211> LENGTH: 632
<212> TYPE: DNA
<213> ORGANISM: Amaranthus hybridus

<400> SEQUENCE: 23

| | | | | | |
|---|---|---|---|---|---|
| tcgaaacctg | cctagcagat | tgaccagcga | acatgtttat | catgagtgga | gcgggagcgc | 60 |
| cctagcgaag | ccttacggac | gagctattgc | cccctcctcc | caacgtcggg | tggtgctcct | 120 |
| ttctgagggg | tgctgctcga | tgcaacaacg | aaccccggcg | cggtctgcgc | caaggaacat | 180 |
| gaacttgagc | gtgctcgtct | tgtgcccggg | tcaccggcgc | atgggagtcg | atgcacccaa | 240 |

```
taatgagtat taaacgactc tcggcaacgg atatcttggc tctcgcatcg atgaagaacg    300
tagcgaaatg cgatacttgg tgtgaattgc agaatcccgt gaaccatcga gttttgaac    360 gcaagttgcg cccgaagcct tcggccaggg cacgtctgcc tgggcgtcac gcactgcgtc    420
tcccccaacc cacctagctg tgggaggggc gaggaggatg gtctcccatg cctcaccggg    480
cgtggatggc ctaaaacagg agcccacggt ttcaagctgc tgcggcgatt ggtggtgtgc    540
aaggcctagc ctagaatgca atcgcgtcgc acagtgcgtt gaccttgtgg ccttgaggac    600
cctagagcgt tgcccgaggg cgaccaacca at                                 632

<210> SEQ ID NO 24
<211> LENGTH: 631
<212> TYPE: DNA
<213> ORGANISM: Amaranthus powellii

<400> SEQUENCE: 24
tcgaaacctg cctagcagat tgaccagcga acatgtttat catgagtgga gcgggagcgc     60
cctagcgaag ccttacggac gagctattgc cctctcctcc caacgtcggg tggtgctcct    120
ttttgagggg tgctgctcga tgcaacaacg aaccccggcg cggtctgcgc caaggaacat    180
gaacttgagc gtgctcgtct tgtgcccggg tcaccggcgc atgggagtgg atgcacccaa    240
tattgagtat taaacgactc tcggcaacgg atatcttggc tctcgcatcg atgaagaacg    300
tagcgaaatg cgatacttgg tgtgaattgc agaatcccgt gaaccatcga gttttgaac    360 gcaagttgcg cccgaagcct ttggccaggg cacgtctgcc tgggcgtcac gcactgcgtc    420
tcccccaacc cgcctagctg tgggaggggc gaggaggatg gtctcccatg cctcaccggg    480
cgtggatggc ctaaaacagg agcccacggt ttcgagctgc tgcggcgatt ggtggtgtgc    540
aaggcctagc ctagaatgca atcgcgtcgc acagtgcgta gccttgtggc cttgaggacc    600
ctagagcgtt gcccgagggc gaccaaccac t                                  631

<210> SEQ ID NO 25
<211> LENGTH: 632
<212> TYPE: DNA
<213> ORGANISM: Amaranthus retroflexus

<400> SEQUENCE: 25
tcgaaacctg cctagcagat tgaccagcga acatgtttat catgagtgga gcgggtgcgc     60
cctagcgaag ccttacggac gagctattgc ccctcctcc caacgtcggg tggtgctcct    120
ttttgagggg tgctgctcga tgcaacaacg aaccccggcg cggtctgcgc caaggaacat    180
gaacttgagc gtgctcgtct tgtgcccggg tcaccggcgc atgggagtgg atgcacccaa    240
tattgagtat taaacgactc tcggcaacgg atatcttggc tctcgcatcg atgaagaacg    300
tagcgaaatg cgatacttgg tgtgaattgc agaatcccgt gaaccatcga gttttgaac    360 gcaagttgcg cccgaagcct ttggccaggg cacgtctgcc tgggcgtcac gcactgcgtc    420
tcccccaacc cgcctagctg tgggaggggc gaggaggatg gtctcccatg cctcaccggg    480
cgtggatggc ctaaaacagg agcccacggt tttgagctgc tgcggcgatt ggtggtgtgc    540
aaggcctagc ctagaatgca atcgcgtcgc acagtgcgta gaccttgtgg ccttgaggac    600
cctagagcgt tgcccgaggg cgaccaacca ct                                 632

<210> SEQ ID NO 26
<211> LENGTH: 2006
<212> TYPE: DNA
<213> ORGANISM: Amaranthus tuberculatus
```

<400> SEQUENCE: 26

```
atggcgtcca cttctcaacc accattttct tcttttacta acctaacaaa atccctaatc      60
ttcaatcctc catttatgct ctcccttttt ccaattctct taaacccgct tcttcatctt     120
caatcctccg ccgccctctt caaatctcat catcttcttc tcaatcacct aaacctaaac     180
ctccttccgc tactataact caatcacctt catctctcac cgatgataaa ccctcttctt     240
ttgttttccg atttagccct gatgaaccca gaaaaggttg cgatgttctc gttgaagctc     300
ttgaacgtga aggtgttacc gatgtttttg cttaccctgg tggagcttcc atggaaatcc     360
atcaagctct tactcgttct aatatcatta gaaatgttct tcctcgacat gaacaaggtg     420
gggttttcgc tgctgaaggc tacgctcgtg ctactggacg tgttggagtt gtattgcca      480
cttctggtcc gggtgctact aatcttgttt ccggttttgc tgatgcactt cttgactcag     540
tcccgcttgt cgccattact gggcaagttc ctcggcgtat gattggtact gatgcttttc     600
aagagactcc tattgttgag gtaactcgat caattactaa gcataattat ttggtgttag     660
atgttgagga tatccctaga attgttaagg aagctttctt tttagctaat tctggtagac     720
ctggacctgt tttgattgat attcctaaag atattcagca acagttggtt gttcctaact     780
gggaacagcc cattaaattg ggtgggtatc tttctaggtt gcctaaaccc acttttttctg    840
ctaatgaaga gggacttctt gatcaaattg tgaggttggt gggtgagtct aagagacctg     900
tgctgtatac tggaggtggg tgtttgaatt ctagtgaaga attgaggaaa tttgtcaagt     960
tgacagggat tccggttgct agtactttaa tggggttggg ggcttttcccct tgtactgatg   1020
atttatcact tcaaatgttg ggaatgcacg ggactgtgta cgcgaattac gcggtggata    1080
aggctgattt gttgcttgct ttcggcgtta ggtttgatga tcgagtgact gggaagctcg    1140
aggcgtttgc tagccgggct aagattgtgc acatcgatat cgattctgct gaaatcggga    1200
agaataagca acctcatgtg tcgatttgtg gtgatgttaa agtggcatta cgggggttga    1260
ataatatttt ggaatctaga aaaggaaagg tgaaattgga tttctctaat tggagggagg    1320
aattgaatga gcagaaaaag aagtttcctt tgagttttaa gactttcggg gatgcaattc    1380
ctccgcaata tgccattcag gttctggacg agttaacgaa gggtgatgcg attgtaagta    1440
ccggtgttgg gcagcaccaa atgtgggctg cccaattttta taagtaccga aatcctcgcc    1500
aatggctgac ctcgggtggt ttgggggcta tgggttttgg tctaccagcc gctattggag    1560
ctgctgttgc tcgaccagat gcggtggttg tagacattga tggggacggg agttttatca    1620
tgaatgttca agagttggct acgattaggg tggagaatct cccggttaaa atcatgctct    1680
tgaacaatca acatttaggt atggttgttc aatgggaaga tcgattttac aaagctaacc    1740
gggcacatac ataccctcggr aatccwtcca attcttcmga aatcttcccg gatatgctsa    1800
aatttgctga agcatgtgat ataccagcag cccgtgttac caaggtgagc gatttaaggg    1860
ctgcaattca aacaatgttg gatactccag gaccatatct gctggatgta atcgtaccac    1920
atcaggagca tgtgctgcct atgatcccta gcggtgccgc cttcaaggac accatcacag    1980
agggtgatgg aagaagggct tattag                                         2006
```

<210> SEQ ID NO 27
<211> LENGTH: 2009
<212> TYPE: DNA
<213> ORGANISM: Amaranthus palmeri

<400> SEQUENCE: 27

```
atggcgtcca cttcaacaaa cccaccattt tcctcttttta ctaaacctaa caaaatccct    60
aatctgcaat catccattta cgctatccct ttttccaatt ctcttaaacc cacttcttct   120
tcttcttctt caatcctccg ccgccctctt caaatctcat catcttcttc tcaatcacct   180
aaacctaaac ctccttccgc tactataact caatcacctt catctctcac cgatgataaa   240
ccctcttctt ttgtttcccg atttagccct gaagaaccca gaaaaggttg cgatgttctc   300
gttgaagctc ttgaacgtga aggtgttacc gatgttttg cttaccctgg tggagcatcc    360
atggaaatcc atcaagctct tactcgttct aatatcatta gaaatgttct tcctcgacat   420
gaacaaggtg gggttttcgc tgctgaaggc tacgctcgtg ctactggacg cgttggagtt   480
tgtattgcca cttctggtcc aggtgctact aatcttgttt ctggtcttgc tgatgcactt   540
cttgactcag tcccgcttgt cgccattact gggcaagttc cccggcgtat gattggtact   600 gatgctttc aagagactcc aattgttgag gtaactcgat ccattactaa gcataattat   660
ttggtgttag atgttgagga tattcctaga attgttaagg aagctttctt tttagctaat   720
tctggtagac ctggacctgt tttgattgat attcctaaag atattcagca acaattagtt   780
gttcctaatt gggaacagcc cattaaattg ggtgggtatc tttctaggtt gcctaaaccc   840
acttattctg ctaatgaaga gggacttctt gatcaaattg taaggttagt gggtgagtct   900
aagagacctg tgctgtatac tggaggtggg tgtttgaatt ctagtgaaga attgaggaaa   960
tttgtcgaat tgacagggat tccggtggct agtactttaa tggggttggg ggctttccct  1020
tgtactgatg atttatcact tcatatgttg ggaatgcatg ggactgtgta cgcgaattac  1080
gcggttgata aggccgattt gttgcttgct ttcggggtta ggtttgatga tcgagtgact  1140
ggtaagcttg aggcgtttgc tagccgggct aagattgtgc acatcgatat cgattctgct  1200
gaaatcggga gaataagca acctcatgtg tcgatttgtg gtgatgttaa agtggcatta  1260
cagggtttga ataagatttt ggaatctaga aaaggaaagg tgaaattgga tttctctaat  1320
tggagggagg agttgaatga gcagaaaaag aagtttcctt taagttttaa gactttcggg  1380
gatgcaattc ctccgcaata cgccattcag gttcttgacg agttgacgaa gggtgatgcg  1440
gttgtaagta ccggtgttgg gcagcaccaa atgtgggctg cccaattcta taagtaccga  1500
aatcctcgcc aatggctgac ctcgggtggt ttgggggcta tggggtttgg tctaccagct  1560
gctattggag ctgctgttgc tcgaccagat gcggtggttg tagacattga tggggatggg  1620
agttttatca tgaatgttca agagttggct acgattaggg tggagaatct cccggttaaa  1680
atcatgctct tgaacaatca acatttaggt atggttgttc aattggaaga tcgattttac  1740
aaagctaacc gggcacatac atacctcggg aatccttcca attcttccga aatcttcccg  1800
gatatgctca aattcgctga agcatgtgat ataccagcag ctcgtgttac caaggtgagc  1860
gatttaaggg ctgcaattca aacaatgttg gatactccag gaccgtatct gctggatgta  1920
atcgtaccac atcaggagca tgtgctgcct atgatcccta gcggtgccgc cttcaaggac  1980
accatcacag agggtgatgg aagaagggc                                    2009

<210> SEQ ID NO 28
<211> LENGTH: 2009
<212> TYPE: DNA
<213> ORGANISM: Amaranthus spinosus

<400> SEQUENCE: 28
atggcgtcca cttcaacaaa cccaccattt tcctcttttta ctaaacctaa caaaatccct    60
aatctgcaat catccattta cgctatccct ttttccaatt ctcttaaacc cacttcttct   120
```

```
tcttcttctt caatcctccg ccgccctctt caaatctcat catcttcttc tcaatcacct        180
aaacctaaac ctccttccgc tactataact caatcacctt catctctcac cgatgataaa        240
ccctcttctt tgtttcccg atttagccct gaagaaccca gaaaaggttg cgatgttctc         300
gttgaagctc ttgaacgtga aggtgttacc gatgttttg cttaccctgg tggagcatcc         360
atggaaatcc atcaagctct tactcgttct aatatcatta gaaatgttct tcctcgacat        420
gaacaaggtg gggttttcgc tgctgaaggc tacgctcgtg ctactggacg cgttggagtt        480
tgtattgcca cttctggtcc aggtgctact aatcttgttt ctggtcttgc tgatgcactt        540
cttgactcag tcccgcttgt cgccattact gggcaagttc cccggcgtat gattggtact        600
gatgcttttc aagagactcc aattgttgag gtaactcgat ccattactaa gcataattat        660
ttggtgttag atgttgagga tattcctaga attgttaagg aagctttctt tttagctaat        720
tctggtagac ctggacctgt tttgattgat attcctaaag atattcagca acaattagtt        780
gttcctaatt gggaacagcc cattaaattg ggtgggtatc tttctaggtt gcctaaaccc        840
acttattctg ctaatgaaga gggacttctt gatcaaattg taaggttagt gggtgagtct        900
aagagacctg tgctgtatac tggaggtggg tgtttgaatt ctagtgaaga attgaggaaa        960
tttgtcgaat tgacagggat tccggtggct agtactttaa tggggttggg ggctttccct       1020
tgtactgatg atttatcact tcatatgttg gaatgcatg ggactgtgta cgcgaattac        1080
gcggttgata aggccgattt gttgcttgct ttcggggtta ggtttgatga tcgagtgact       1140
ggtaagcttg aggcgtttgc tagccgggct aagattgtgc acatcgatat cgattctgct       1200
gaaatcggga agaataagca acctcatgtg tcgatttgtg gtgatgttaa agtggcatta       1260
cagggtttga ataagatttt ggaatctaga aaaggaaagg tgaaattgga tttctctaat       1320
tggagggagg agttgaatga gcagaaaaag aagtttcctt taagttttaa gactttcggg       1380
gatgcaattc ctccgcaata cgccattcag gttcttgacg agttgacgaa gggtgatgcg       1440
gttgtaagta ccggtgttgg gcagcaccaa atgtgggctg cccaattcta taagtaccga       1500
aatcctcgcc aatggctgac ctcgggtggt ttgggggcta tggggtttgg tctaccagct       1560
gctattggag ctgctgttgc tcgaccagat gcggtggttg tagacattga tggggatggg       1620
agttttatca tgaatgttca agagttggct acgattaggg tggagaatct cccggttaaa       1680
atcatgctct tgaacaatca acatttaggt atggttgttc aattggaaga tcgattttac       1740
aaagctaacc gggcacatac atacctcggg aatccttcca attcttccga aatcttcccg       1800
gatatgctca aattcgctga agcatgtgat ataccagcag ctcgtgttac caaggtgagc       1860
gatttaaggg ctgcaattca aacaatgttg gatactccag gaccgtatct gctggatgta       1920
atcgtaccac atcaggagca tgtgctgcct atgatcccta gcggtgccgc cttcaaggac       1980
accatcacag agggtgatgg aagaagggc                                          2009
```

<210> SEQ ID NO 29
<211> LENGTH: 2065
<212> TYPE: DNA
<213> ORGANISM: Amaranthus powellii

<400> SEQUENCE: 29

```
cttcaagctt caacaatggc gtccacttct tcaaacccac catttcctc tttactaaa         60 cctaacaaaa tccctaatct gcaatcatcc atttacgcta tccctttttc caattctctt       120
aaacccactt cttcttcttc aatcctccgc cgccctcttc aaatctcatc atcttcttct      180
```

```
caatcaccta aacctaaacc tccttccgct actataactc aatcaccttc gtctctcacc    240
gatgataaac cctcttcttt tgtttcccga tttagccctg aagaacccag aaaaggttgc    300
gatgttctcg ttgaagctct tgaacgtgaa ggtgttaccg atgttttttgc ttaccctggt   360 ggagcatcca tggaaattca tcaagctctt actcgttcta atatcattag aaatgttctt    420
cctcgacatg aacaaggtgg ggttttcgct gctgaaggct acgctcgtgc tactggacgc    480
gttggagttt gtattgccac ttctggtcca ggtgctacta tcttgtttc tggtcttgct     540 gatgcacttc ttgactcagt ccctcttgtc gccattactg ggcaagttcc ccggcgtatg    600
attggtactg atgcttttca agagactcca attgttgagg taactcgatc cattaccaag    660
cataattatt tggtgttaga tgttgaggat attcctagaa ttgttaagga agctttcttt    720
ttagctaatt ctggtagacc tggacctgtt tgattgata ttcctaaaga tattcagcaa     780
caattagttg ttcctaattg ggaacagccc attaaattgg gtgggtatct ttctaggttg    840
cctaaaccca cttattctgc taatgaagag ggacttcttg atcaaattgt aaggttagtg    900
ggtgagtcta agagacctgt gctgtatact ggaggtgggt gtttgaattc tagtgaagaa    960
ttgaggaaat ttgtcgaatt gacaggtatt ccggtggcta gtactttaat ggggttgggg   1020 gctttcccctt gtactgatga tttatctctt catatgttgg gaatgcacgg gactgtgtac   1080
gcgaattacg cggttgataa ggccgatttg ttgcttgctt ttggggttag gtttgatgat   1140
cgagtgactg gtaagctcga ggcgtttgct agccgggcta gattgtgca catcgatatc    1200 gattctgctg aaatcgggaa gaataagcaa cctcatgtgt cgatttgtgg tgatgttaaa   1260
gtggcattac aggggttgaa taagattttg gaatctagaa aaggaaaggt gaaactggat   1320
ttctctaatt ggagggagga gttgaatgag cagaaaaaga gtttcctttt gagttttaag   1380
actttcgggg atgcaattcc tccgcaatac gccattcagg ttcttgacga gttgacgaag   1440
ggcgatgcgg ttgtaagtac tggtgttggg cagcaccaaa tgtgggctgc ccaattctat   1500
aagtaccgaa atcctcgcca atggctgacc tcggtggtt tgggggctat ggggtttggt    1560
ctaccagctg ctattggagc tgctgttgct cgaccagatg cggtggttgt agacattgat   1620
ggggatggga gtttcatcat gaatgttcaa gagttggcta cgattagggt agagaatctc   1680
ccggttaaaa tcatgctctt gaacaatcaa catttaggta tggttgttca atgggaagat   1740
cgattttaca aagctaaccg ggcacataca tacctcggga atccttccaa ttcttccgaa   1800
atcttcccgg atatgctcaa atttgctgaa gcatgtgata taccagcagc ccgtgttacc   1860
aaggtgagcg atttaaggac tgcaattcaa acaatgttgg atactccagg accgtatctg   1920
ctggatgtaa tcgtaccaca tcaggagcat gtgctgccta tgatccctag cggtgccgcc   1980
ttcaaggaca ccataacaga gggtgatgga agaagggctt attagttggt tggagatcct   2040
tatagaggag aagctttttg tagga                                         2065
```

<210> SEQ ID NO 30
<211> LENGTH: 2065
<212> TYPE: DNA
<213> ORGANISM: Amaranthus retroflexus

<400> SEQUENCE: 30

```
cttcaagctt caacaatggc gtccacttct tcaaacccac cattttcctc ttttactaaa    60
cctaacaaaa tccctaatct gcaatcatcc atttacgcta tccctttttc caattctctt   120
aaacccactt cttcttcttc aatcctccgc cgccctcttc aaatctcatc atcttcttct   180
caatcaccta aacctaaacc tccttccgct actataactc aatcaccttc gtctctcacc   240
```

-continued

```
gatgataaac cctcttcttt tgtttcccga tttagtcctg aagaacccag aaaaggttgc    300
gatgttctcg ttgaagctct tgaacgtgaa ggtgttaccg atgttttgc ttaccctggt     360 ggagcatcca tggaaattca tcaagctctt actcgttcta atatcattag aaatgttctt    420
cctcgacatg aacaaggtgg ggttttcgct gctgaaggct acgctcgtgc tactggacgc    480
gttggagttt gtattgccac ttctggtcca ggtgctacta atcttgtttc tggtcttgct    540
gatgcacttc ttgactcagt ccctcttgtc gccattactg gcaagttcc ccggcgtatg     600 attggtactg atgctttca agagactcca attgttgagg taactcgatc cattaccaag     660
cataattatt tggtgttaga tgttgaggat attcctagaa ttgttaagga agctttcttt    720
ttagctaatt ctggtagacc tggacctgtt ttgattgata ttcctaaaga tattcagcaa    780
caattagttg ttcctaattg ggaacagccc attaaattgg gtgggtatct ttctaggttg    840
cctaaaccca cttattctgc taatgaagag ggacttcttg atcaaattgt aaggttagtg    900
ggtgagtcta agagacctgt gctgtatact ggaggtgggt gtttgaattc tagtgaagaa    960
ttgaggaaat tgtcgaatt gacaggtatt ccggtggcta gtactttaat ggggttgggg   1020 gctttcccctt gtactgatga tttatctctt catatgttgg aatgcacgg gactgtgtac   1080 gcgaattacg cggttgataa ggccgatttg ttgcttgctt ttggggttag gtttgatgat   1140
cgagtgactg gtaagctcga ggcgtttgct agccgggcta agattgtgca catcgatatc   1200
gattctgctg aaatcgggaa gaataagcaa cctcatgtgt cgatttgtgg tgatgttaaa   1260
gtggcattac aggggttgaa taagattttg gaatctagaa aaggaaaggt gaaattggat   1320
ttctctaatt ggagggagga gttgaatgag cagaaaaaga gtttcctttt gagttttaag   1380
actttcgggg atgcaattcc tccgcaatac gccattcagg ttcttgacga gttgacgaag   1440
ggcgatgcgg ttgtaagtac tggtgttggg cagcaccaaa tgtgggctgc ccaattctat   1500
aagtaccgga atcctcgcca atggctgacc tcggtggtt tgggggctat ggggtttggt    1560
ctaccagctg ctattggagc tgctgttgct cgaccagatg cggtggttgt agacattgat   1620
ggggatggga gttttatcat gaatgttcaa gagttggcta cgattagggt agagaatctc   1680
ccggttaaaa tcatgctctt gaacaatcaa catttaggta tggttgttca atgggaagat   1740
cgattttaca aagctaaccg ggcacataca tacctcggga atccttccaa ttcttccgaa   1800
atcttcccgg atatgctcaa atttgctgaa gcatgtgata taccagcagc ccgtgttacc   1860
aaggtgagcg atttaagggc tgcaattcaa acaatgttgg atactccagg accgtatctg   1920
ctggatgtaa tcgtaccaca tcaggagcat gtgctgccta tgatccctag cggtgccgcc   1980
ttcaaggaca ccataacaga gggtgatgga agaagggctt attagttggt tggagatcct   2040
tatagaggag aagcttttg tagga                                          2065
```

<210> SEQ ID NO 31
<211> LENGTH: 96
<212> TYPE: DNA
<213> ORGANISM: Artificial Sequence
<220> FEATURE:
<223> OTHER INFORMATION: Primer

<400> SEQUENCE: 31

```
ccgggcgtgg atggcctaaa aagcaggagc ccgcggtttc gagctgctgc ggcgattggt    60
ggtgtgcaag gcctagccta gaatgcaatc gcgtcg                              96
```

<210> SEQ ID NO 32

-continued

```
<211> LENGTH: 121
<212> TYPE: DNA
<213> ORGANISM: Artificial Sequence
<220> FEATURE:
<223> OTHER INFORMATION: Primer

<400> SEQUENCE: 32
ggtctgcgcc aaggaacatg aacttgagcg tgctcgtctt gtgcccgggt caccggcgca      60
tgggagtgga tgcacccaat attgagtatt gaaacgactc tcggcaacgg atatcttggc    120
t                                                                    121

<210> SEQ ID NO 33
<211> LENGTH: 43
<212> TYPE: DNA
<213> ORGANISM: Artificial Sequence
<220> FEATURE:
<223> OTHER INFORMATION: Primer

<400> SEQUENCE: 33
gaaggtgacc aagttcatgc tcgggcgtgg atggcctaaa aag                       43

<210> SEQ ID NO 34
<211> LENGTH: 43
<212> TYPE: DNA
<213> ORGANISM: Artificial Sequence
<220> FEATURE:
<223> OTHER INFORMATION: Primer

<400> SEQUENCE: 34
gaaggtcgga gtcaacggat tcgggcgtgg atggcctaaa aca                       43

<210> SEQ ID NO 35
<211> LENGTH: 18
<212> TYPE: DNA
<213> ORGANISM: Artificial Sequence
<220> FEATURE:
<223> OTHER INFORMATION: Primer

<400> SEQUENCE: 35
accaatcgcc gcagcagc                                                   18

<210> SEQ ID NO 36
<211> LENGTH: 42
<212> TYPE: DNA
<213> ORGANISM: Artificial Sequence
<220> FEATURE:
<223> OTHER INFORMATION: Primer

<400> SEQUENCE: 36
gaaggtgacc aagttcatgc tatccgttgc cgagagtcgt tc                        42

<210> SEQ ID NO 37
<211> LENGTH: 42
<212> TYPE: DNA
<213> ORGANISM: Artificial Sequence
<220> FEATURE:
<223> OTHER INFORMATION: Primer

<400> SEQUENCE: 37
gaaggtcgga gtcaacggat tatccgttgc cgagagtcgt tt                        42

<210> SEQ ID NO 38
<211> LENGTH: 23
<212> TYPE: DNA
<213> ORGANISM: Artificial Sequence
```

<220> FEATURE:
<223> OTHER INFORMATION: Primer

<400> SEQUENCE: 38
acatgaactt gagcgtgctc gtc                                          23

<210> SEQ ID NO 39
<211> LENGTH: 51
<212> TYPE: DNA
<213> ORGANISM: Artificial Sequence
<220> FEATURE:
<223> OTHER INFORMATION: Primer

<400> SEQUENCE: 39
gaaggtgacc aagttcatgc taaaaagaaa gcttccttaa caattctagg g           51

<210> SEQ ID NO 40
<211> LENGTH: 51
<212> TYPE: DNA
<213> ORGANISM: Artificial Sequence
<220> FEATURE:
<223> OTHER INFORMATION: Primer

<400> SEQUENCE: 40
gaaggtcgga gtcaacggat taaaaagaaa gcttccttaa caattctagg a           51

<210> SEQ ID NO 41
<211> LENGTH: 29
<212> TYPE: DNA
<213> ORGANISM: Artificial Sequence
<220> FEATURE:
<223> OTHER INFORMATION: Primer

<400> SEQUENCE: 41
gttgaggtaa ctcgatcaca ttactaagc                                    29

<210> SEQ ID NO 42
<211> LENGTH: 706
<212> TYPE: DNA
<213> ORGANISM: Myriophyllum spicatum

<400> SEQUENCE: 42
gtcgtaacaa ggtttccgta ggtgaacctg cggaaggatc attgtcgaaa cctgcacagc   60
agaacgaccc gtgaactaat aaacacccgg ggggagagga gggagctgca cttgtgcggc  120
gccacccctc gcccccagt gcctagacgc gcccctgcc tacaccggac tttgttcggc   180
gtcggcagga ggtcgtccat ggcgacaata acaaaccccg cgcggaaag cgccaaggaa   240 atcatgacga acttagcaca ccactagccg acttgtgcgg cagcggcgtt gcaaacttcg  300 ataccctaaac gactctcggc aacggatatc tcggctctcg catcgatgaa gaacgtagcg  360
aaatgcgata cttggtgtga attgcagaat cccgtgaacc atcgagtttt tgaacgcaag  420
ttgcgcccga agccattcgg ccgagggcac gtctgcctgg gcgtcacgta tcgcgttgct  480
cccaaagccc acccttcaag gataaggcgc tgcggaagca gatattggcc tcccgtgcct  540
gcgcacggct ggcctaaatg caagcctggg ggtgacgaaa gggtcacgac aagcggtggt  600
tgataactca gcctttgttg cgccgtgccc gccgtgcccc ttggagctca gcatcccga   660 cgcgccgtct cgacggcgtt tgcatcgcga ccccaggtca ggcggg                706

<210> SEQ ID NO 43
<211> LENGTH: 198
<212> TYPE: DNA

```
<213> ORGANISM: Myriophyllum spicatum

<400> SEQUENCE: 43
aaagcccacc cttcaaggat atggtgctgc ggaagcagat attggcctcc cgtgcctgtg     60
cacggatggc ctaaatgcaa gcctggggct gacgaaaggg tcacgacaag cggtggttga    120
taactcagcc tttgttgcgt cgtgcccgcc gtgccccttg gagctcagca tccccgacgc    180
gctgtctcga cggcgttt                                                  198

<210> SEQ ID NO 44
<211> LENGTH: 165
<212> TYPE: DNA
<213> ORGANISM: myriophyllum spicatum

<400> SEQUENCE: 44
aaagcccacc cttcaaggat aaggcgctgc ggaagcagat attggcctcc cgtgtctgcg     60
cacggctggc ctaaatgcaa gcctgggggt gacgaaaggg tcacgacaag cggtggttga    120
taactcagcc tttgttgcgc cgtgcccgcc gtgccccttg gagct                    165

<210> SEQ ID NO 45
<211> LENGTH: 541
<212> TYPE: DNA
<213> ORGANISM: Myriophyllum spicatum

<400> SEQUENCE: 45
atacgcgccc cctgccacac cggactttgt tcggcgtcgg caggaggtcg tccatggcga     60
caataacaaa ccccggcgcg gaaagcgcca aggaaatcat gacgaactta gcacaccact    120
agccgacttg tgcggcagcg gcgttgcaaa cttcgatacc taaacgactc tcggcaacgg    180
atatctcggc tctcgcatcg atgaagaacg tagcgaaatg cgatacttgg tgtgaattgc    240
agaatcccgt gaaccatcga gtttttgaac gcaagttgcg cccgaagcca ttcggccgag    300
ggcacgtctg cctgggcgtc acgtatcgcg ttgctcccaa agcccaccct tcaaggataa    360
ggcgctgcgg aagcagatat tggcctcccg tgcctgcgca cggctggcct aaatgcaagc    420
ctgggggtga cgaaagggtc acgacaagcg gtggttgata actcagcctt tgttgcgccg    480
tgcccgccgt gccccttgga gctcagcatc cccgacgcgc cgtctcgacg gcgtttgcat    540
c                                                                    541

<210> SEQ ID NO 46
<211> LENGTH: 421
<212> TYPE: DNA
<213> ORGANISM: Myriophyllum sibiricum

<400> SEQUENCE: 46
taaagtcgac ggattttcct cttactataa atttcattgt tgtcatcatt gacatgtaga     60
atgggactct atctttattc tcgtccgatt aatcagctcg tcaaaatctc tatcagattt    120
tggaagtgaa tgattttatc aatgaataaa tgaatattcg attctttctt cacctaggaa    180
tttattcaca aaaattcttt catttttata tattttcata aaaaaaaatt tcataaaaaa    240
aaaaagattt gaatcatccg ttgatgttga tatagtattt cagtacgtat atatatggtt    300
tatcattcat cctttcggga gtttgggtgg agggattcct ttaccaacgc aacgtagtca    360
actccttttg ttagaacaac ttccattgag tctctgcacc tatccttctt tttttatttt    420
a                                                                    421
```

```
<210> SEQ ID NO 47
<211> LENGTH: 163
<212> TYPE: DNA
<213> ORGANISM: Artificial Sequence
<220> FEATURE:
<223> OTHER INFORMATION: Vector control 2

<400> SEQUENCE: 47
catgacgaac ttagcacacc actagccgac ttgtgcggca gcggcgttgc aaacttcgat     60
acctacaaag cccacccttc aaggataagg cgctgcggaa gcagatattg gataactcag   120
cctttgttgc gccgtgcccg ccgtgcccct tggagctcag cat                     163
```

HIGH THROUGHPUT METHOD TO GENOTYPE PLANTS

REFERENCE TO RELATED APPLICATIONS

This application claims priority to previously filed and provisional application U.S. Ser. No. 62/336,207, filed May 13, 2016, the contents of which are incorporated herein by reference in its entirety and provisional application U.S. Ser. No. 62/462,219 filed Feb. 22, 2017 the contents of which are incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on May 5, 2017, is named CSURF_SEQ_ST25 and is 33,083 bytes in size.

BACKGROUND

In any particular geographic area, whether aquatic or land, it is often desirable to determine in a population of plants the genotype of those plants. A particular challenge is when in a population of plants there exists more than one species of a genus of the plant, where one or more species has a characteristic distinct from the other, yet is morphologically indistinct. An example of such a situation is where within a population of plants, the wild type species is inter-planted with another species that is more aggressive, more resistant to herbicide application, or has another undesirable characteristic. This is complicated further when the species inter-breed, producing a hybrid.

An example is watermilfoil plants of the genus *Myriophyllum*. The invasive aquatic plant Eurasian watermilfoil (*Myriophyllum spicatum* L.) readily hybridizes with the related North American native species northern watermilfoil (*M. sibiricum* Kom.). Hybrid watermilfoil (*M. spicatum*×*M. sibiricum*) populations have higher fitness and reduced sensitivity to some commonly used herbicides, making management more difficult. There is growing concern that management practices using herbicides with mixed populations such as watermilfoil species may further select for hybrid individuals due to the difference in herbicide sensitivity. Accurate and cost-effective identification of hybrid individuals within populations is therefore critical for management decisions.

Still another example are the land plants of the genus *Amaranthus*. Palmer amaranth (*Amaranthus palmeri*) and waterhemp (*Amaranthus tuberculatus*) are important weed species that can contaminate seeds for sale (e.g., wildflowers, native grasses). Palmer amaranth has been listed as a prohibited noxious weed species in some US states, meaning that a seed lot containing Palmer amaranth may not legally be sold. Waterhemp is prohibited from seeds for sale in Canada and China. Waterhemp and Palmer amaranth seeds cannot be distinguished visually from other, non-noxious *Amaranthus* species, such as redroot pigweed (*Amaranthus retroflexus*), smooth pigweed (*Amaranthus hybridus*), and spiny amaranth (*Amaranthus spinosus*). There is no fast and inexpensive method for the seed testing industry to reliably assess bulked amaranth seed samples as containing Palmer amaranth or not. Therefore, the seed production and analysis industry has considerable interest in a DNA-based test to identify the presence of any Palmer amaranth and waterhemp seeds.

SUMMARY

A method for determining the genotype of a population of plants is provided with a system using at least three primers, a first primer recognizing a target sequence specific to a species of the plant genus of interest, a second primer recognizing a target in the second species, and a third primer recognizing a third target sequence in both the first and second species or group of species. Under proper amplification conditions, a DNA-containing sample produces a measurable signal that allows the sample to be sample determined as a member of the first or second species, a mixture of the species, or a hybrid. Multiple species may be determined in this manner. The process provides for fast identification of a large number of samples such that the population of plants can be genotyped. In one example, proper application of appropriate herbicide or other control measures to the population may be more accurately determined as a result of such genotyping. In an embodiment, the process is repeated three times with different target sequences and the results analyzed to produce increased accuracy of genotyping. Another embodiment provides for a control for comparison of results by transforming bacteria with one of the target sequences, or a 1:1 mixture of the two target sequences, contacting the plasmids with the primers to produce a measurable signal for control measurements.

BRIEF DESCRIPTION OF THE DRAWINGS

FIGS. 2 A, B, and C are SNPs 118, 363, and 478, respectively. Dashed lines represent cutoffs for making genotyping calls. The solid quarter circle line is the cutoff for no-amplification.

FIGS. 5A-B is an alignment of the Internal Transcribed Spacer (ITS) region from nine *Amaranthus* species with A showing polymorphism that differentiates Palmer amaranth with ⁀ and Panel B polymorphism that differentiates waterhemp with ˆ.

FIGS. 6A-C is an alignment of nine *Amaranthus* species of the ITS genomic region.

FIG. 7 is an alignment of the acetolactate synthase (ALS) gene from five *Amaranthus* species showing polymorphism that differentiates waterhemp indicated with ˆ.

FIGS. 8A-E is an alignment of the ALS gene from five *Amaranthus* species.

DESCRIPTION

Figure 1:
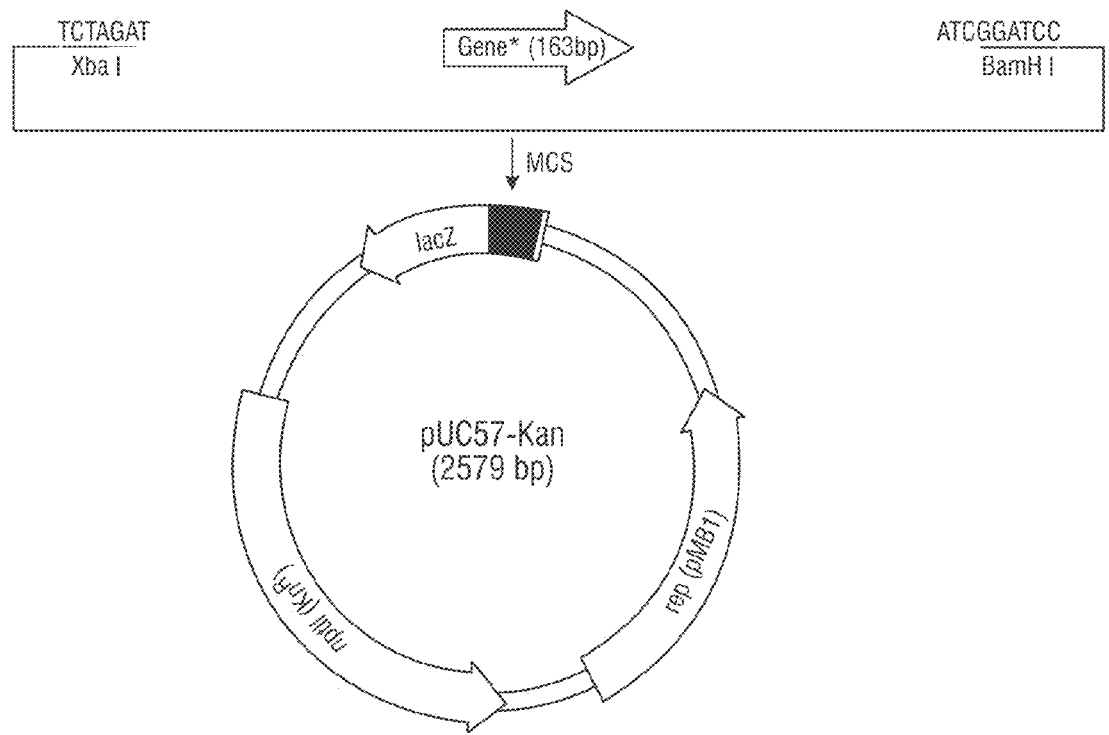
FIG. 1 is a graphic representation of the cloning strategy for two plasmid inserts in the pUC57-Kan plasmid. The cloning strategy and insert size is identical for the two plasmids, so a generic map is given that represents the strategy for both plasmids.

Provided here are methods of genotyping a population of plants using high throughput methodology that is capable of distinguishing one species of genus or group of species from another and further can distinguish plants that are a hybrid of species within a genus. With the methods described here hundreds and thousands of plants may be screened in a day and at a cost that is 1/10 the cost of present processes (in one instance costing less than $10 whereas genotyping with RFLP is approximately $20-$30 per sample). The reduction in cost compared to RFLP identification methods can be one times, two times, ten times, three times, four times, five times, six times, seven times, eight times, nine times, ten times or more less than RFLP process. The methods are especially useful where analyzing a population of plants, and, in particular, invasive weedy plants, in order to select the most efficient means of eradication of the invasive plant.

When referring to genotyping plants is meant to include genotyping a population of plants, plant parts, tissue or seed. The DNA sample may be obtained in any convenient matter, as from any tissue, callus, organ or plant part for example. The term plant or plant material or plant part is used broadly herein to include any plant at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or aggregate of cells such as a friable callus, or a cultured cell, or can be part of a higher organized unit, for example, a plant tissue, plant organ, or plant. Thus, a plant cell can be a protoplast, a gamete producing cell, or a cell or collection of cells that can regenerate into a whole plant. As such, a seed, which comprises multiple plant cells and is capable of regenerating into a whole plant, is considered a plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like. The tissue culture will preferably be capable of regenerating plants.

In one example described in more detail below, the invasive aquatic plant of the *Myriophyllum* genus damages aquatic environments by outcompeting native plants and forming mats that damage other beneficial vegetation. Two species include *Myriophyllum sibiricum*, and the aggressive *Myriophyllum spicatum*. Hybrids of the two species are considerably less susceptible to herbicide and thus pose a particular environmental concern. Additional challenges are that the invasive and native plants are phenotypically the same and hybridization blurs the ability to identify variations. Currently, PCR-RFLP is used to distinguish one species from another.

A still further example is Palmer amaranth (*Amaranthus palmeri*) and waterhemp (*Amaranthus tuberculatus*), important weed species that can contaminate seeds for sale (e.g., wildflowers, native grasses). Palmer amaranth has been listed as a prohibited noxious weed species in some US states, meaning that a seed lot containing Palmer amaranth may not legally be sold. Waterhemp is prohibited from seeds for sale in Canada. Waterhemp and Palmer amaranth seeds cannot be distinguished visually from other, non-noxious *Amaranthus* species, such as redroot pigweed (*Amaranthus retroflexus*), smooth pigweed (*Amaranthus hybridus*), and spiny amaranth (*Amaranthus spinosus*).

The process described here uses Kompetitive Allele Specific PCR, also known as a KASP™ assay. It is based on competitive allele-specific PCR and allows scoring of single nucleotide polymorphisms (SNPs), as well as deletions and insertions at specific loci. Two allele specific forward primers are used having the target SNP at the 3' end and a common reverse primer is used for both. The primers have a unique "tail" sequence (reporter nucleotide sequence) compatible with a different fluorescent reporter (reporter molecule). The primers are contacted with the sample along with a mix which includes a universal Fluorescence Resonant Energy Transfer (FRET) cassette and Taq polymerase. During rounds of PCR cycling, the tail sequences allow the FRET cassette to bind to the DNA and emit fluorescence. See, e.g. Yan et al. "Introduction of high throughput and cost effective SNP genotyping platforms in soybean" *Plant Genetics, Genomic and Biotechnology* 2(1): 90-94 (2014); Semagn et al. "Single nucleotide polymorphism genotyping using Kompetitive Allele Specific PCR (KASP): overview of the technology and its application in crop improvement" *Molecular Breeding* 33(1): 1-14 (2013). In the present process, emission of one fluorescent signal (reporter molecule) or the other indicates the plant is one of the two species, where presence of both signals indicates a hybrid. Examples here show use of 6-carboxyfluorescein (FAM); and 6-carboxy-2',4,4',5',7,7'-hexachlorofluorescein (HEX) fluorophores, however any convenient means of producing a measurable signal may be used. Examples without intending to be limiting include tetrachlorofluorescein (TET); cyan florescent protein, yellow fluorescent protein, luciferase, SyBR Green I; ViC; CAL Fluor Gold 540, ROX Texas Red; CAL Fluor Red 610; CYS; Quasar 670; Quasar 705; and Fret.

In sum, a first primer is produced recognizing a first target nucleotide sequence in the genome of a first species, a second primer is produced recognizing a second target nucleotide sequence of a second species and the third common reverse primer universal to all genotypes allows for amplification. A "tail" reporter sequence is provided with the primer. The expression cassette comprises sequences complementary to the reporter sequence. With rounds of PCR, the cassette is no longer quenched and a measurable signal is produced.

Further variations for identifying weedy species can be employed. In an embodiment, a noxious or weed species may be identified by a first primer as above, specific to the weedy species, and a first tail reporter sequence (such as FAM, for example), and a second primer common to other non-weedy species and a different tail (such as HEX) may be used to determine if a weedy species is present.

The process further can employ additional primers that recognize target sequence of a third, fourth or additional species of the genus. The process adds one or more primers which each have a "tail" reporter sequence, the expression cassette comprises sequences complementary to the reporter sequence and when bound produces an additional different reporter molecule. The method thus can further comprise at least one additional primer recognizing a target nucleotide sequence in the genome of said plant genus specific to a species other than the first or second species and further comprising a reporter sequence other than the first or second reporter sequence, the third primer recognizing a target nucleotide sequence in the genome of said first species, second species and said species other than said first or second species, and where the expression cassette includes a sequence complementary to the sequence other than said first or second reporter sequence and a sequence encoding a reporter molecule and determining if said sample DNA comprises DNA of said first species, second species, species other than said first or said species, or a hybrid of any of said species.

In the present process KASP™ assays are employed for genotyping a large population of plants and in an embodiment a population of weedy plants which can be invasive plants, or any plants that grow where they are not desired, and plants that need to be eradicated as a group. By using the assay, it is possible to obtain a DNA sample for a large number of plants in a population, determine which species they are, and if they are hybrid, and adjust eradication methods for optimum use with the plant population. By way of example without limitation, a 96 well plate can be used to analyze 90 plants using six wells for control, for an improved determination of the predominate genotype of a plant population. In another example, 1500 plants can be analyzed with 35 controls, allowing for even large sampling of a population. Rather than each well subject to a different assay, an individual plant is assayed in each well. Using these methods, as demonstrated below, the ability to detect variation within a population is increased. In one example, 36 individual plants were assayed, only one of which was a hybrid.

In an embodiment, the assay provides for an improved control for measuring results of the KASP™ assay. Typically, a control plant is grown in hydroponic culture to serve as a control. Here, DNA is cloned, placed in an *E. coli* vector and introduced into *E. coli* for amplification. Each different species may be introduced into *E. coli*. The DNA may be extracted from the *E. coli* for use as a control. Where a hybrid control is to be produced, the two plasmids with DNA of each species are mixed at a ratio of 1:1. The result is a less expensive, less time consuming control that does not require greenhouse conditions or tissue culture.

In a further embodiment the control consists of a mixture of plant tissue, such as plant seeds. The seeds are a collection of different species of a plant genus, provided in known ratios dependent upon the detection limit that is useful for a particular population. In one example, set forth in more detail below, Palmer amaranth seeds were mixed with redroot pigweed in ratios that provided, there Palmer amaranth seeds were mixed with redroot pigweed in ratios of 10:0, 8:2, 6:4, 4:6, 2:8, and 0:10. The specific ratios will vary depending upon the mix of species expected and at the level of detection desired. In a still further embodiment, plasmids may be used as controls, as discussed above, where a plasmid is provided for each species to be detected, as referred to above.

Still another embodiment provides for increased efficacy by performing the KASP assay at three distinct loci. The inventors have found that when they perform the assay on three loci with different SNPs, each using its own set of primers, and combine the results in discriminate analysis, up to 100% accuracy is obtained. For example, discriminant analysis is used to predict which species a plant belongs to (a categorical variable) by the observed (continuous) fluorescence values. When a single SNP is used, the separation between the different fluorescence values for species one, species two, and the hybrid may be clear leading to 100% likelihood of the individual plant belonging to the group it is assigned to by discriminant analysis. However, for some SNPs, the separation between the different fluorescence values is less clear, leading to a less than 100% likelihood of the group assignment being correct (although usually the likelihood is still over 90%). When multiple SNPs are tested in the same plant, discriminant analysis can be performed on all the fluorescence values obtained from the different assays. Since a plant can only belong to one of the three groups (species one, species two, or hybrid), the combination of information from the different SNPs leads to a higher probability that the assignment is correct.

The primers recognize target sequences which distinguish one species of the genus of plant from another species or group of species. Below an example is provided of the Internal Transcribed Spacer region which is useful in identifying one species of watermilfoil or *Amaranthus* from another. Any target sequence in a plant genus may be used where a polymorphism distinguishes between species of plants. Thousands of single nucleotide polymorphisms have been identified over the years that distinguish plant species and a skilled person may select from the many nucleic acid sequences or SNPs available. For example, thousands of SNPs are available readily through such databases as maizegdb.org; soybase.org.snps; 1001genomes.org (*Arabidopsis*); and described in many articles such as Maughan et al. (2011) "Development, characterization and linkage mapping of SNPs in grain amaranths" *Plant Gen* 4:92-101 doi:10/38351/plantgenome2010.12.0027. Any convenient target sequences may be used in the process.

The process in an embodiment is especially useful with weedy, invasive and noxious plant control. Weedy plants are those growing where they are not desired. The USDA maintains a list of federal and state noxious weeds. A noxious weed is defined as a plant that can directly or indirectly injure or cause damage to crops, livestock, poultry or other interest of agriculture, irrigation, navigation, the natural resources of the United States, the public health or the environment. 7 U.S.C. § 7702 (12). Examples, without intending to be limiting, of noxious aquatic species are *Azolla pinnata Caulerpa taxifolia* (Mediterranean strain), *Eichhornia azurea, Hydrilla verticillate, Hygrophila polysperma, Ipomoea aquatica, Lagarosiphon major Limnophila sessiliflora, Melaleuca quinquenervia, Monochoria hastate, Monochoria vaginalis, Ottelia alismoides, Sagittaria sagittifolia, Salvinia auriculata, Salvinia biloba, Salvinia herzogii, Salvinia molesta* and *Solanum tampicense*. Examples of land weeds include, without limitation, *Acacia nilotica, Ageratina adenophora, Ageratina riparia, Alternanthera sessilis, Amaranthus genus, Arctotheca calendula,*

*Asphodelus fistulosis, Avena sterilis, Carthamus oxyacantha, Chrysopogon aciculatus, Commelina benghalensis, Crupina vulgaris, Digitaria scalarum, Digitaria velutina, Drymaria arenariodes, Emex australis, Emex spinose, Euphorbia terracina, Galega officinalis, Heracleum mantegazzianum, Imperata brasiliensis, Imperata cylindrica, Inula britannica, Ischaemum rugosum, Leptochloa chinensis, Lycium ferocissimum, Lygodium flexuosum, Lygodium microphyllum, Melastoma malabathricum, Mikania cordata, Mikania micrantha, Mimosa invisa, Mimosa pigra, Moraea collina, Moraea flaccida, Moraea miniate, Moraea ochroleuca, Moraea pallida, Nassella trichotoma, Onopordum acaulon, Onopordum Illyricum, Opuntia aurantiaca, Oryza longistaminata, Oryza punctate, Oryza rufipogon, Paspalum scrobiculatum, Pennisetum clandestinum, Pennisetum macrourum, Pennisetum pedicellatum, Pennisetum polystachion, Prosopis genus, Rottboellia cochinchinensis Rubus fruticosis Rubus moluccanus Saccharum spontaneum Sagittaria sagittifolia Salsola vermiculata Senecio inaequidens Senecio madagascariensis, Setaria pumila* ssp. *pallidefusca* (Now: ssp. *subtesselata*), *Solanum torvum Solanum viarum, Spermacoce alata, Tridax procumbens*, and *Urochloa panicoides*.

An embodiment allows the genotyping of a population of watermilfoil aquatic plants, distinguishing between the Eurasian watermilfoil (*Myriophyllum spicatum*), Northern watermilfoil (*Myriophyllum sibiricum*) and hybrids of the two. A further embodiment provides for distinguishing the species and hybrid by identifying a SNP within the nuclear ribosomal Internal Transcribed Spacer Region (ITS) of the plant genome. The ITS region can differentiate nearly all North American watermilfoil species, which are inherited biparentally and thus can be used also to identify hybrids. This region of the genome has been identified by Moody and Les (2007) and is found at GenBank accession numbers AF513849, AF513850, DQ786012-DQ786029. See Moody and Les "Geographic distribution and genotypic composition of invasive hybrid watermilfoil (*Myriophyllum spicatum*×*M. sibiricum*) populations in North America" *Biol. Invasions* 9:559-570 (2007).

Watermilfoil molecular studies are set forth in Sturtevant et al. which also sets forth twenty-three SNPs. Sturtevant et al, "Molecular Characterization of Eurasian Watermilfoil, Northern Milfoil, and the Invasive Interspecific Hybrid in Michigan Lakes" *J. Aquat. Plant Manage* 47:128-135 (2009). When referring here to digestion at base pair 274 or 551 of the ITS PCR product, is referring to Grafe et al "A PCR-RFLP method to detect hybridization between the invasive Eurasian watermilfoil (*Myriophyllum spicatum*) and the native northern watermilfoil (*Myriophyllum sibiricum*), and its application in Ontario lakes" Botany 93:117-121 (2015). The ITS region was amplified with the universal primers (forward) ITS5 (5'-GGAAGTAAAAGTCG-TAACAAGG-3' (SEQ ID NO: 1)), and (reverse) ITS4 (5'-TCCTCCGCTTATTGATATGC-3'(SEQ ID NO: 2)) (White et al 1990) producing a product of 750 bp. In Grafe et al, the authors aligned sequences obtained to the reference sequence FJ426346.1 (SEQ ID NO: 3), from Sturtevant et al 2009. However, to find the restriction sites, they looked through all the published ITS sequences for *M. spicatum* and *M. sibiricum*. In FJ426346, which is *M. spicatum*, FspI cuts at bp 551. In FJ426352 (SEQ ID NO: 4), which is *M. sibiricum*, BmtI cuts at bp 274.

The process is useful in determining the best methods for control of a plant population. When a population of plants is determined to have a higher proportion of weed plants and/or more aggressive hybrids, it is possible to adjust control methods for the particular population. More aggressive measures can be taken when the population contains a higher amount of such noxious or invasive species or hybrids. The control methods can reduce growth of a higher number of plants in such instances. After genotyping of the population, control measures may be adjusted. Control methods can reduce growth of undesired plants, can reduce the growth of the entire population, or enhance desired plants. It is useful with any control or eradication measures, whether physical removal, application of biological controls such as insects, fungi, microbes or the like, application of naturally occurring compositions that impact plant growth, chemical applications such as herbicides, or any other convenient method. In one example, once the population of watermilfoil is genotyped, it is possible to adjust eradication methods, and, for example, apply a higher rate of herbicide where the population is predominately hybrid. Methods of control of weeds such as aquatic weeds are well known, such as that discussed at Heilman et al. US20130157857; Mann, US20150218099; Koschnick et al. US20150018213; and Mango US20100273655.

The ability to genotype dozens of individuals provides the ability to identify the presence of rare individuals, such as a less common parental species or the inter-specific hybrid. Land populations and lakes with complex species distribution dynamics, such as low proportion of hybrids, are where herbicide application or choice of herbicide must be carefully made so as not to select for the more vigorous and less herbicide sensitive hybrid individuals. With the ability to genotype hundreds of individuals rapidly and inexpensively using KASP™, weed managers will be able to make more informed decisions about herbicide type and application rates, such as choosing specific herbicides and rate to control hybrid individuals only when they are confirmed to be present. Larger data sets comprised of accurate genotyping data will allow modeling of plants including weedy invasive plants such as *Myriophyllum* species distribution dynamics, testing the hypothesis that increased selection pressure from herbicide application favors hybrid individuals due to their decreased herbicide sensitivity. In one example, populations can be genotyped using KASP™ both before and after herbicide applications to quantify shifts in species distribution dynamics towards invasive species or hybrid individuals.

The following is provided by way of exemplification without intending to be limiting to the scope of the invention. References cited here are incorporated herein by reference in their entirety.

EXAMPLES

Example 1

The invasive aquatic plant Eurasian watermilfoil (*Myriophyllum spicatum* L.) was introduced to the United States from Asia during the 1940s (Couch and Nelson 1988; Moody et al. 2016). After introduction, this submersed species spread rapidly throughout the United States, forming dense monotypic mats that have caused economic and ecological damage to infested lakes, streams, and reservoirs (Eiswerth et al. 2000; Olden and Tamayo 2014). The decrease in native plant diversity that occurs after *M. spicatum* invasion is an alarming ecological impact (Madsen et al. 1991). Furthermore, it is now apparent that the invasive *M. spicatum* readily hybridizes with the related North American native species northern watermilfoil (*M. sibiricum* Kom.) (Grafe et al. 2015; Moody and Les 2007; Zuellig and Thum 2012).

Some hybrid watermilfoil (*M. spicatum*×*M. sibiricum*) populations appear to have higher fitness manifested as faster and more aggressive growth rate both in laboratory and field conditions than either parental species, making management more difficult (Hovick and Whitney 2014; LaRue et al. 2013). Additionally, hybrid populations are less sensitive to some commonly used herbicides, including 2,4-D, fluridone, norflurazon, and topramazone (Berger et al. 2015; LaRue et al. 2013). There is growing concern that current management practices in lakes with mixed populations of watermilfoil species, which rely heavily on herbicide application, may further select for hybrid populations due to the difference in herbicide sensitivity.

Several methods to accurately identify *M. spicatum, M. sibiricum*, and *M. spicatum*×*M. sibiricum* hybrid individuals using morphological characteristics have been proposed. Morphological characteristics, while sufficient to distinguish between *M. spicatum* and *M. sibiricum*, are no longer reliable once hybrid individuals are present, as the hybrid characteristics are often intermediate between the two species (e.g., the number of pinnae or leaflet pairs) (Coffey and McNabb 1974; Moody and Les 2007).

Sufficient genetic variation exists between the two species that genotyping is an accurate method for species identification (Moody and Les 2002; Sturtevant et al. 2009). Current methods rely on single nucleotide polymorphisms (SNPs) within the nuclear ribosomal internal transcribed spacer (ITS) regions of *M. spicatum* and *M. sibiricum* (Moody and Les 2002), using 23 intra-genic polymorphic SNPs in the first and second Internal Transcribed Spacer regions (ITS1 and ITS2). Of these SNPs, 11 clearly distinguish between *M. spicatum* and *M. sibiricum*. When a single individual is heterozygous for both alleles of a single SNP, it indicates the individual is an inter-specific hybrid. That individual will also be heterozygous for the remaining 10 SNPs due to linkage of the SNPs within the ITS regions.

SNP genotyping in these species has been performed using several methods. Originally, the ITS region was amplified via polymerase chain reaction (PCR), the PCR products were cloned, and multiple clones were sequenced to determine whether an individual was homozygous or heterozygous at the ITS SNPs (Grafe et al. 2014). This process requires the longest time and highest cost per sample of available methods. Subsequently, genotyping was streamlined with the development of a PCR restriction fragment length polymorphism (PCR-RFLP) assay using either a BmtI or FspI restriction digest that cut at base pair (bp) 274 or 551 of the ITS amplicon, respectively as discussed supra. By eliminating the cloning and sequencing for species identification with the PCR-RFLP assay, Grafe et al. (2014) were able to substantially decrease the amount of time and money per sample required for positive species identification of individual watermilfoil specimens. The higher throughput enabled larger sample sizes per lake, providing a more accurate estimate of *Myriophyllum* species distribution dynamics.

Advances in SNP genotyping provide more cost-effective and accurate results than PCR-RFLP. Currently, the Kompetitive Allele Specific PCR (KASP) assay is a common technique for genotyping SNPs. This assay is used in several fields, including plant breeding, disease identification, and species identification (Semagn et al. 2014). KASP is able to discriminate between two alleles of a SNP using a common reverse primer paired with two forward primers, one specific to each allele. Each forward primer also has a nucleotide sequence that hybridizes in one example to either the HEX or FAM fluorophore quencher. Amplification proceeds using stringent conditions to only permit forward primers to bind if they are perfectly complementary to the template sequence. Fluorophores are released from the quencher molecule when a forward primer is incorporated in a PCR product, causing the released fluorophore to fluoresce. This fluorescence is detected at the end of the assay using a real-time PCR machine, and the proportion of fluorescence from HEX, FAM, or both indicates the genotype of the sample.

KASP genotyping has several advantages compared to PCR-RFLP assays. KASP assays are more convenient, as they are both faster and less expensive. Eighty or more individuals can be genotyped simultaneously (in a 96 well plate), giving a much more accurate view of the *Myriophyllum* species distribution dynamics within a lake, and providing an increased likelihood of detecting a rare hybrid individual. KASP assay design is very flexible, as primer design is not limited to available restriction enzyme recognition sites, and primers can even cover stretches of sequence containing multiple SNPs by incorporating degenerate or mixed bases into the primer sequence. A target sequence thus can be one or more SNPs in an example. KASP assays are quantitative and therefore amenable to statistical analysis, such that probabilities can be assigned to genotyping calls. Data from multiple SNP genotyping assays can be integrated into a single model, increasing the robustness of species diagnostics.

Here we describe KASP assays for three SNPs in the ITS region to genotype individuals from both parental watermilfoil species and their hybrid, using synthesized plasmids containing the respective sequences as positive controls. Using KASP we genotyped dozens of individuals from two lakes, giving a highly accurate picture of *Myriophyllum* species distribution dynamics in each case. Discriminant analysis showed that while a single SNP was generally sufficient for genotyping an individual, using multiple SNPs increased the reliability of genotyping.

Materials and Methods

Plant Collection

Several previously identified *M. spicatum* biotypes and known inter-specific watermilfoil hybrid (*M. spicatum*×*M. sibiricum*) biotypes (eight biotypes each) were harvested from aquaponics cultures maintained in the CSU Weed Research lab. Unknown *Myriophyllum* individuals were collected from two lakes in northern Colorado, Rainbow Lake located at 40.506758, −104.989224 and Walleye Lake at 40.505680, −104.982883. Individual stems (Rainbow, n=23; Walleye, n=16) were collected from each lake by rake throws. A single leaf was used for DNA extraction and therefore a tissue sample is assumed to represent a unique individual. Tissue samples were stored in sealed bags with damp paper towels at 4 C until DNA extraction.

Plant DNA Extraction

DNA was extracted from 50 mg of watermilfoil leaf tissue using a modified CTAB method (Doyle 1991). All steps were performed at room temperature (22° C.) unless otherwise indicated. In brief, tissue was initially ground to a fine powder with a metal bead in 500 µL of 2×CTAB buffer (2% CTAB, 1% PVP, TRIS-EDTA pH 5) using a Qiagen TissueLyser at 30 oscillations/second for 1 minute. Ground samples were incubated at 65° C. for 1 hour, after which 500 µL of phenol:chloroform:isoamyl alcohol (25:24:1) was added. The samples were slowly rocked on an orbital shaker for 15 minutes. Samples were centrifuged at 10,000×g for 5 minutes. The upper phase was transferred to a new tube, to which 500 µL of chloroform:isoamyl alcohol (24:1) was added. The samples were again centrifuged at 10,000×g for 5 minutes. The upper phase was transferred to a new tube and nucleic acids were precipitated using 0.1 volumes of 3 M sodium acetate and 2.5 volumes of 100% ethanol. Samples were precipitated at 4° C. for 15 minutes and then centrifuged at 15,000×g for 15 minutes. The resulting pellets were re-suspended in 50 µL of sterilized water. DNA concentrations and quality were assessed using a spectrophotometer (NanoDrop 2000 Spectrophotometer, Thermo Fisher Scientific, Wilmington, Del., USA). Samples were subsequently diluted to 5 ng/µL for use in all KASP assays.

Plasmid Design

Two plasmids were designed as positive controls for the KASP assay. Plasmid inserts were comprised of the sequence within the ITS region complementary to the genotyping primers, with all inter-primer sequence removed (FIG. 1). The complete oligonucleotides were synthesized by GenScript in the puc57-Kan plasmid. Below are the sequence of the M. sibiricum and M. spicatum positive plasmid controls.

Plasmid Sequence

```
Plasmid 1

Gene name: M_Sib_Positive_Control

Length: 163 bp

Vector name: pUC57-Kan

Sequence (SEQ ID NO: 5):
CATGACGAACTTAGCACACCGCTAGCCGACTTGTGCGGCAGCGGCGTTGC

AAACTTCGATACCTACAAAGCCCACCCTTCAAGGATATGGTGCTGCGGAA

GCAGATATTGGATAACTCAGCCTTTGTTGCGTCGTGCCCGCCGTGCCCCT

TGGAGCTCAGCAT

Plasmid 2
Gene name: M_Spi_Positive_Control

Length: 163 bp

Vector name: pUC57-Kan

Sequence (SEQ ID NO: 47):
CATGACGAACTTAGCACACCACTAGCCGACTTGTGCGGCAGCGGCGTTGC

AAACTTCGATACCTACAAAGCCCACCCTTCAAGGATAAGGCGCTGCGGAA

GCAGATATTGGATAACTCAGCCTTTGTTGCGCCGTGCCCGCCGTGCCCCT

TGGAGCTCAGCAT
```

Control plasmids were transformed into Dh5α E. coli cells using a standard heat transformation protocol (provided by GenScript). First all reagents (plasmid and Dh5α cells) were thawed on ice. Next 1 µL of plasmid at 100 ng/µL was added to the Dh5α cells and mixed gently. The mixture was incubated on ice for 30 minutes and then placed in a hot water bath at 42° C. for 45 sec. Tubes were returned to an ice bath for 2 minutes. Next, 1 mL of liquid LB was added to the E. coli and allowed to incubate at 37° C. for 1 hour. Plates containing LB+Kan (Kan at 50 µg/ml) were pre-warmed to 37° C. during this incubation. Next, 200 µL of the E. coli transformation was added to the warmed LB+Kan plate, spread evenly, and allowed to grow at 37° C. for 16 hr. Individual colonies were transferred to a numbered patch plate and allowed to grow at 37° C. for 16 hr.

E. coli DNA Extraction

DNA was extracted from cultures grown from ten colonies on each patch plate. A toothpick was dipped into the E. coli colony and used to inoculate 1 mL of LB+Kan. After incubating for 16 hours at 37° C. with shaking, the E. coli cultures were pelleted by centrifugation at 8000 rcf. DNA was extracted from the pellets using the standard extraction protocol provided with the Qiagen Miniprep kit. DNA concentrations and quality were assessed using a NanoDrop 2000 spectrophotometer. Extracted plasmids were subsequently diluted to 5 pg/µL for use in all KASP assays. A 1:1 mixture of the diluted plasmids was used in KASP assays to simulate an inter-specific hybrid.

Primer Design

Three primer sets were designed for the KASP assay to distinguish three diagnostic SNPs at bp 118, 363, and 478 in the Internally Transcribed Spacer (ITS) region. For each primer set, the forward primer for M. spicatum was assigned the HEX tag while the forward primer for M. sibiricum was assigned the FAM tag. Some primers spanned sequences containing SNPs that discriminate between sub-populations of M. sibiricum, which required the use of degenerate bases in the primers. Primers are shown in Table 1. Degenerate bases are indicated according to the universal code.

TABLE 1

KASP Primers for SNPs 118, 363, and 478 in the Myriophyllum ITS region.

| Primer Name | Primer Sequence (5'-3') | OligoAnalyzer 3.1 Predicted Melting Temperature | SEQ ID NO |
|---|---|---|---|
| SNP 118 (G/A) | | | |
| M. sibiricum FP-118 | CATGACGWACTTAGCACACCG | 55.9 C. | SEQ ID NO: 6 |
| M. spicatum FP-118 | CATGACGAACTTAGCACACCA | 55.2 C. | SEQ ID NO: 7 |
| Universal RP-118 | TAGGTATCGAAGTTTGCAACGC | 55.5 C. | SEQ ID NO: 8 |
| SNP 363 (A/G) | | | |
| M. sibiricum FP-363 | CAATATCTGCTTCCGCAGCA | 55.6 C. | SEQ ID NO: 9 |
| M. spicatum FP-363 | CAATATCTGCTTCCGCAGCG | 56.6 C. | SEQ ID NO: 10 |
| Universal RP-363 | CAAAGCCCACCCTTCAAGGA | 57.7 C. | SEQ ID NO: 11 |

TABLE 1-continued

KASP Primers for SNPs 118, 363, and 478 in the Myriophyllum ITS region.

| Primer Name | Primer Sequence (5'-3') | OligoAnalyzer 3.1 Predicted Melting Temperature | SEQ ID NO |
|---|---|---|---|
| SNP 478 (T/C) | | | |
| M. sibiricum FP-478 | GATAACTCAGCCTYTGTTGCGT | 56.4 C. | SEQ ID NO: 12 |
| M. spicatum FP-478 | GATAACTCAGCCTTTGTTGCGC | 56.9 C. | SEQ ID NO: 13 |
| Universal RP478 | ATGCTGAGCTCCAAGGGGCA | 61.8 C. | SEQ ID NO: 14 |
| 5' FAM TAG (M. sibiricum) | GAAGGTGACCAAGTTCATGCT | | SEQ ID NO: 15 |
| 5' HEX TAG (M. spicatum) | GAAGGTCGGAGTCAACGGATT | | SEQ ID NO: 16 |

KASP Assay

A primer master mix including forward and reverse primers for a single SNP was made. All primers were first re-suspended in Tris-HCl, pH 8.3, at 100 μM. Primer mixes were made according to the manufacturer's recommendations (LGC Genomics), with 18 μL of the M. spicatum forward primer, 18 μL of the M. sibiricum forward primer, 45 μL of the common reverse primer, and 69 μL of 10 mM Tris-HCl, pH 8.3. KASP master mixes were made with 432 μL LGC Genomics Master Mix (which includes polymerase, dNTPs, buffer, and HEX- and FAM-tagged oligonucleotides) and 11.88 μL of primer master mix.

KASP reactions were assembled in a 96-well plate with 4 μL of master mix and either 4 μL water (no template control), 4 μL genomic DNA at 5 ng/μL, or 4 μL of plasmid DNA at 5 pg/μL. Reactions were performed in a BioRad CFX Connect according to the following standard KASP PCR program: Activation at 94° C. for 15 minutes, then 10 touchdown cycles of 94° C. for 20 seconds (denaturing), 61-55° C. for 60 seconds (dropping 0.6 C per cycle, for annealing and elongation), 23° C. for 30 seconds (to permit accurate plate reading), followed by 26 cycles of 94 C for 20 seconds, 55° C. for 60 seconds, 23° C. for 30 seconds. Fluorescence was tracked in real-time with plate reads at the end of every amplification cycle. Fluorescence data from the cycle showing the greatest distinction between clusters without any background amplification was used for genotyping, which was determined to be cycles 22-24 of the amplification phase.

Data Analysis

Due to slight variations in maximum fluorescence and fluorescence in the no template controls between plates, HEX and FAM fluorescence for each data point were transformed as a percentage of the maximum fluorescence for each fluorophore within a plate. Maximum fluorescence is defined as the highest FAM or HEX signal from any reaction in a 96-well plate. Cutoffs for genotyping calls on unknown samples were drawn by calculating the point halfway between the mean x,y coordinate of the control hybrid and either the control M. sibiricum or M. spicatum clusters, then drawing a line from that point to the origin (0,0). Additionally, a zone of "no amplification" was defined by the maximum fluorescence of no-template controls. A quarter circle around the axis intercept was used to define this zone. Genotypes were assigned to unknown samples based on where in the plot their fluorescence values occurred.

Once all samples (experimental samples as well as controls) were assigned a genotype, linear discriminant analysis was performed in JMP 12.2 (SAS Institute Inc., Cary, N.C., USA) to evaluate the probability of an individual having its assigned genotype. Genotyping results from each SNP were first assessed independently, then using all three SNPs combined to provide more robust probabilities.

Results and Discussion

We developed three KASP primer sets that distinguish between the native M. sibiricum and the invasive M. spicatum species as well as inter-specific hybrids. Our KASP primers utilize the previously identified SNPs at base pairs 118, 363, and 478 of the ITS region (Table 1). We tested the primer sets on plasmids containing known sequences; on known lab biotypes of M. spicatum and hybrids; and on unknown Myriophyllum individuals harvested from two lakes in northern Colorado. We assigned genotypes manually, and then measured the reliability of the genotyping calls using discriminant analysis to assign probabilities to calls from each SNP individually as well as using all three SNPs together.

KASP Assays on Plasmids

We developed plasmids to serve as positive controls for the KASP-PCR reaction. Plasmid controls were ideal because they allow for rapid generation of DNA of a known genotype and eliminate the need to maintain both species of Myriophyllum as well as the inter-specific hybrid in hydroponic culture as positive genotyping controls.

Figure 2A:
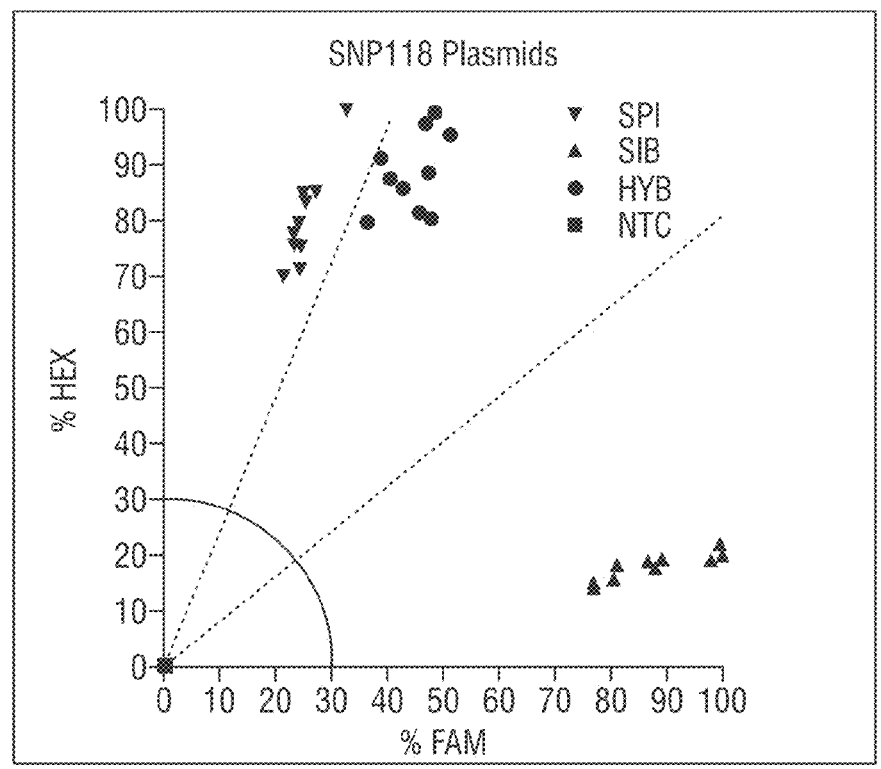
FIGS. 2A-C are graphs showing KASP results for plasmids containing the M_Sib_Positive_Control (▼), M_Spi_Positive_Control (▲), 1:1 mixture of the two to represent hybrids (●), and no template controls (■).
Figure 2B:
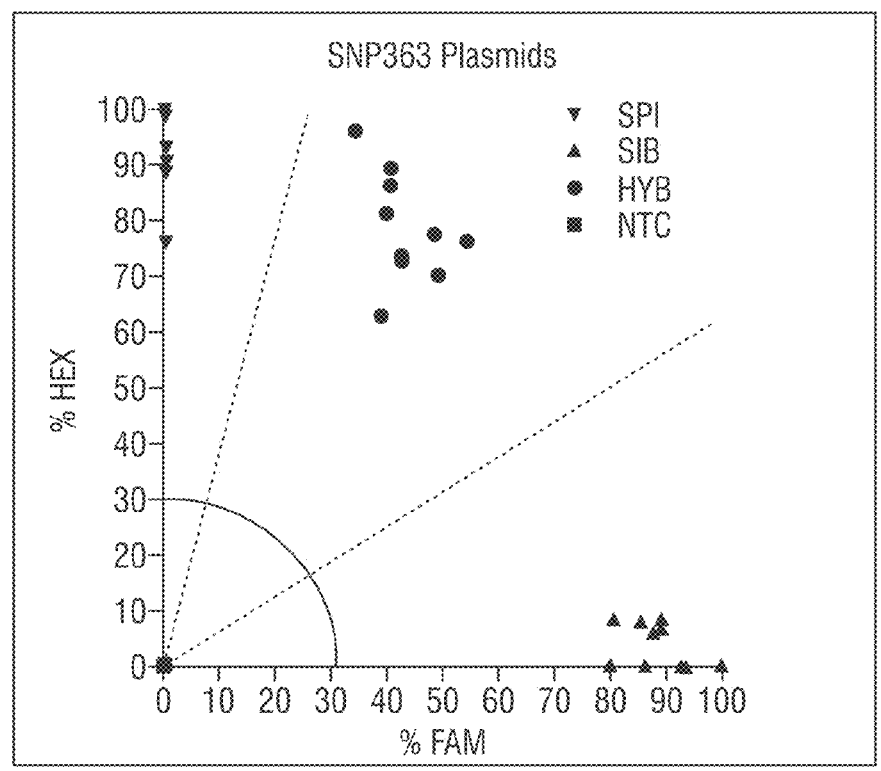
Figure 2C:
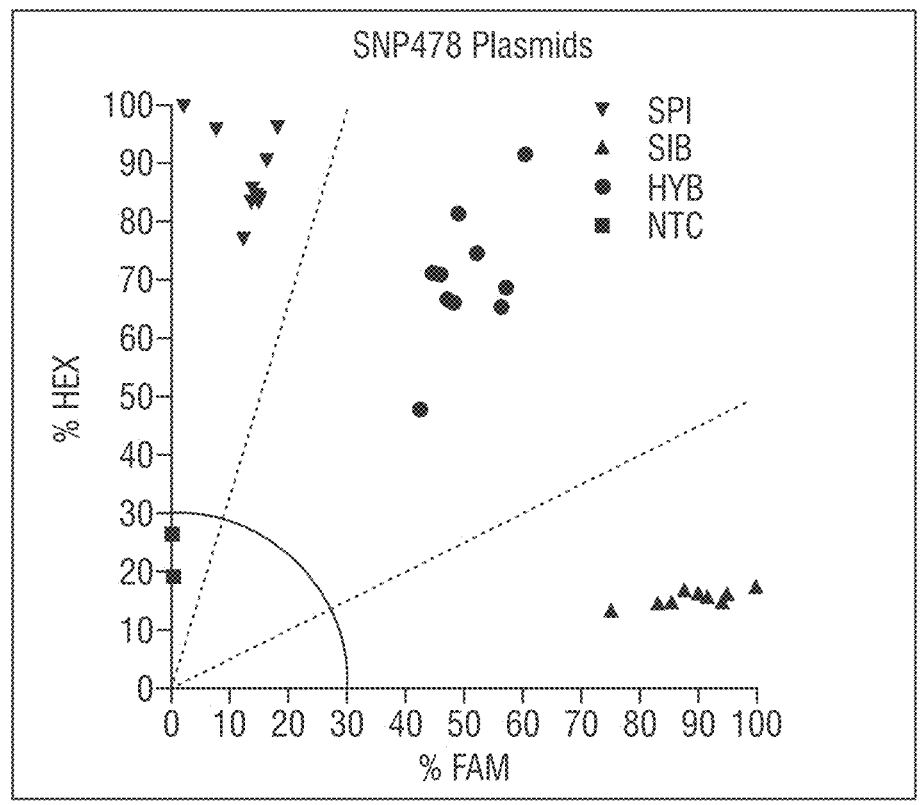

The plasmid DNA performed consistently from assay to assay and allowed us to more accurately characterize unknown individuals in the KASP assay. For SNP 118, SNP 363, and SNP 478, all ten samples from a given genotype formed a tight, distinct cluster on the HEX-FAM x-y plot (FIG. 2). SNP 118 had a very clear M. sibiricum cluster, but the M. spicatum and the 1:1 synthetic hybrids were relatively close to each other, due to increased FAM fluorescence for the M. spicatum samples (FIG. 2A). However, there was no overlap between the M. spicatum samples and the synthetic hybrid samples. SNP 363 and SNP 478 show obvious separation of the fluorescence signal from each of the three possible genotypes, with the M. spicatum plasmids having almost exclusively HEX signal, M. sibiricum plasmids having almost exclusively FAM signal, and the 1:1 mixture of each genotype having both HEX and FAM signal (FIGS. 2B, C). No plasmid had an ambiguous call or fell below the 30% fluorescence threshold for any of the three SNPs. This test confirmed the utility of plasmids as internal positive controls for the subsequent genotyping.

KASP Assays on Lab Biotypes

Figure 3A:
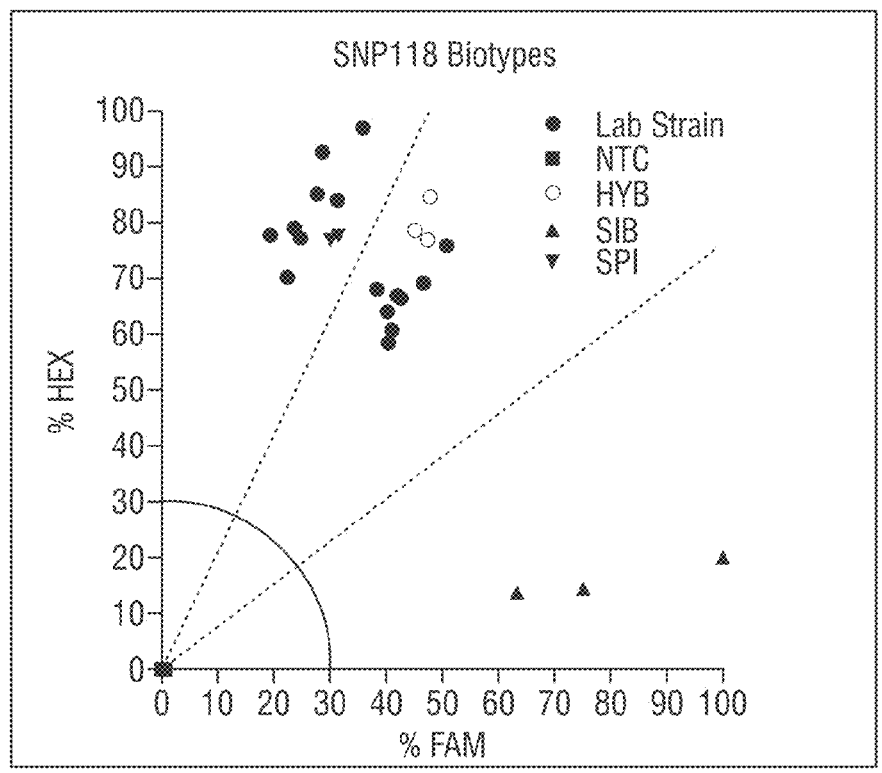
FIGS. 3A-C are graphs showing KASP assays for SNPs 118 (A), 363 (B), and 478 (C) from 16 lab biotypes (eight known inter-specific hybrids and eight known *M. spicatum* biotypes. M_Sib_Positive_Control (▼), M_Spi_Positive_Control (▲), a 1:1 mixture of the two to represent hybrids (●), no template controls (■), and known watermilfoil biotypes (●). Dashed lines represent cutoffs for making genotyping calls. The solid quarter circle line is the cutoff for no-amplification.
Figure 3B:
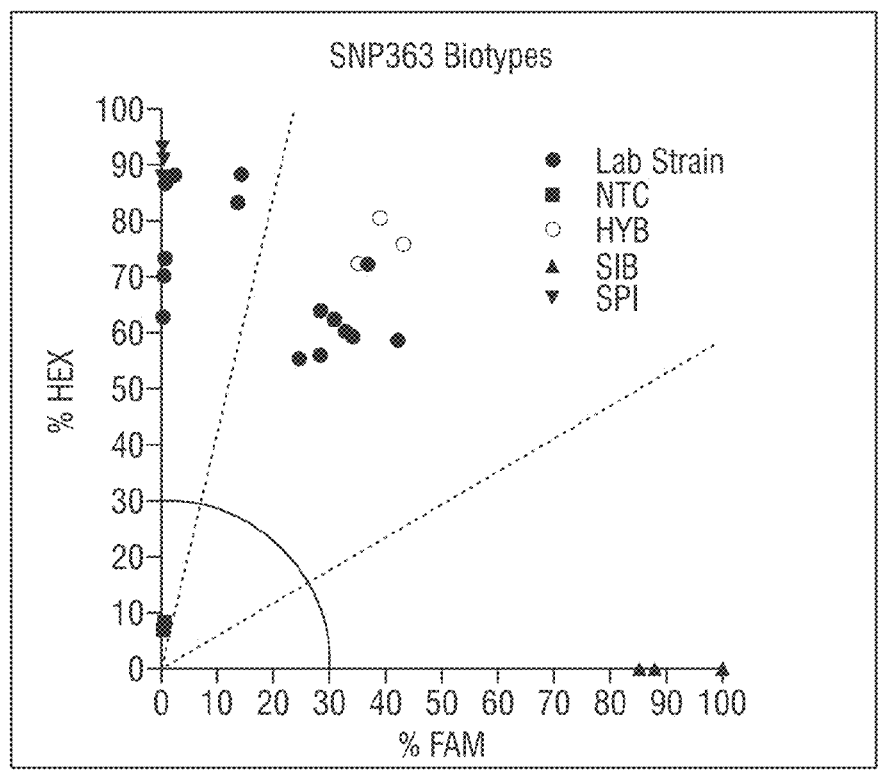
Figure 3C:
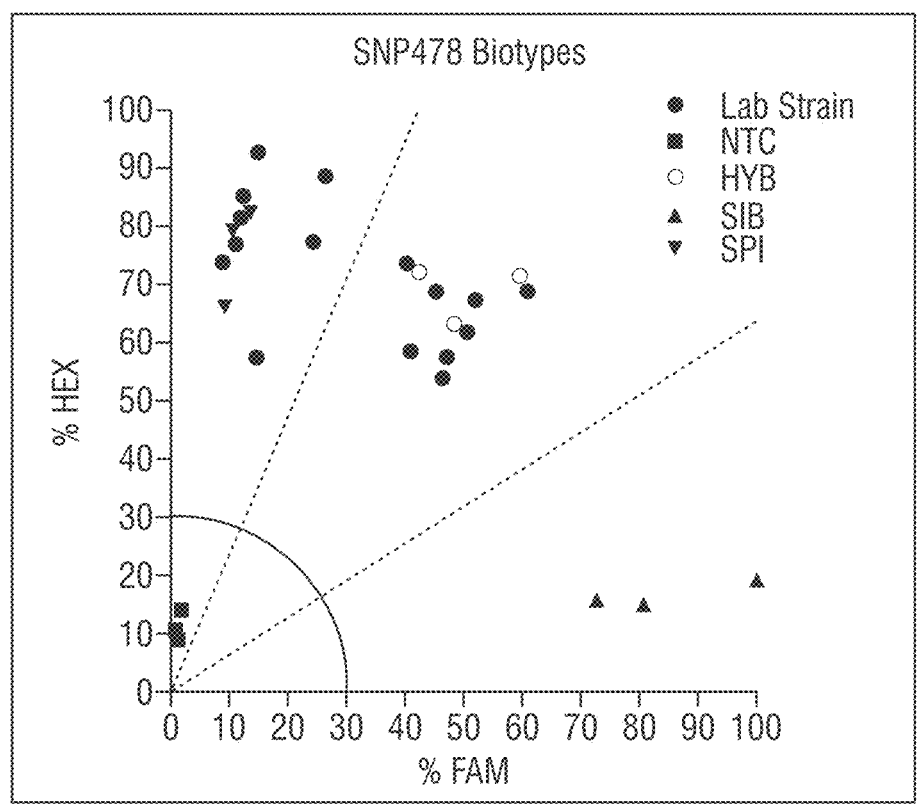

We tested several biotypes of *Myriophyllum* that are maintained in aquaponics culture at CSU. These biotypes were originally collected from various locations in North America (Table 2). The KASP results from all three SNP primer sets showed that eight of these biotypes clustered with the *M. spicatum* plasmid control, with high HEX signal and minimal FAM signal (Norway, CSU KCK, 4BC, St Helens, Hall, Stoney 2, Fawn, Hanbury), while eight clustered with the 1:1 synthetic hybrid mixture of *M. spicatum* and *M. sibiricum* plasmid controls, with approximately equal HEX and FAM fluorescent signals (Hayden, Mattoon, Houghton, Alpine 2, Alpine 3, Richard Farm, Jeff, Alpine 1) (Table 2, FIG. 3).

The predicted probability that a genotype call was correct was calculated by performing discriminant analysis on the corrected fluorescence data for each SNP separately and for all three SNPs together (Table 2). Particularly for SNP118, several individuals had a reduced probability that the genotype was correct (e.g., Norway or Stoney 2). However, when all three SNPs were considered together, the probability was 100% for each genotype call (Table 2). These results confirm that all three SNPs are strongly linked and co-inherited and therefore the three SNPs can be used together to provide accurate genotyping.

TABLE 2

KASP SNP genotyping calls and predicted probability of accuracy for eight known *M. spicatum* (*M. spi*,) biotypes and eight known hybrid (Hyb,) watermilfoil (*M. spicatum* × *M. sibiricum*) biotypes.

| | All three SNPs | | SNP 118 | | SNP 363 | | SNP 478 | |
|---|---|---|---|---|---|---|---|---|
| Sample | Call | Prob (Pred) | Call | Prob (Pred) | Call | Prob (Pred) | Call | Prob (Pred) |
| Norway | *M. spi* | 1.00 | *M. spi* | 0.76 | *M. spi* | 1.00 | *M. spi* | 1.00 |
| Hayden | Hyb | 1.00 | Hyb | 1.00 | Hyb | 1.00 | Hyb | 1.00 |
| Mattoon | Hyb | 1.00 | Hyb | 1.00 | Hyb | 1.00 | Hyb | 1.00 |
| Houghton | Hyb | 1.00 | Hyb | 1.00 | Hyb | 1.00 | Hyb | 1.00 |
| CSU KCK | *M. spi* | 1.00 | *M. spi* | 0.99 | *M. spi* | 1.00 | *M. spi* | 1.00 |
| Alpine 2 | Hyb | 1.00 | Hyb | 1.00 | Hyb | 1.00 | Hyb | 1.00 |
| Alpine 3 | Hyb | 1.00 | Hyb | 1.00 | Hyb | 1.00 | Hyb | 1.00 |
| Richard Farm | Hyb | 1.00 | Hyb | 1.00 | Hyb | 1.00 | Hyb | 1.00 |
| 4BC | *M. spi* | 1.00 | *M. spi* | 0.95 | *M. spi* | 1.00 | *M. spi* | 1.00 |
| St Helens | *M. spi* | 1.00 | *M. spi* | 0.89 | *M. spi* | 1.00 | *M. spi* | 1.00 |
| Jeff | Hyb | 1.00 | Hyb | 1.00 | Hyb | 1.00 | Hyb | 1.00 |
| Hall | *M. spi* | 1.00 | *M. spi* | 0.95 | *M. spi* | 1.00 | *M. spi* | 0.99 |
| Stoney 2 | *M. spi* | 1.00 | *M. spi* | 0.78 | *M. spi* | 1.00 | *M. spi* | 0.98 |
| Fawn | *M. spi* | 1.00 | *M. spi* | 0.95 | *M. spi* | 1.00 | *M. spi* | 1.00 |
| Alpine 1 | Hyb | 1.00 | Hyb | 1.00 | Hyb | 1.00 | Hyb | 1.00 |
| Hanbury | *M. spi* | 1.00 | *M. spi* | 0.99 | *M. spi* | 1.00 | *M. spi* | 1.00 |

KASP Assays on Rainbow and Walleye Lake

Figure 4A:
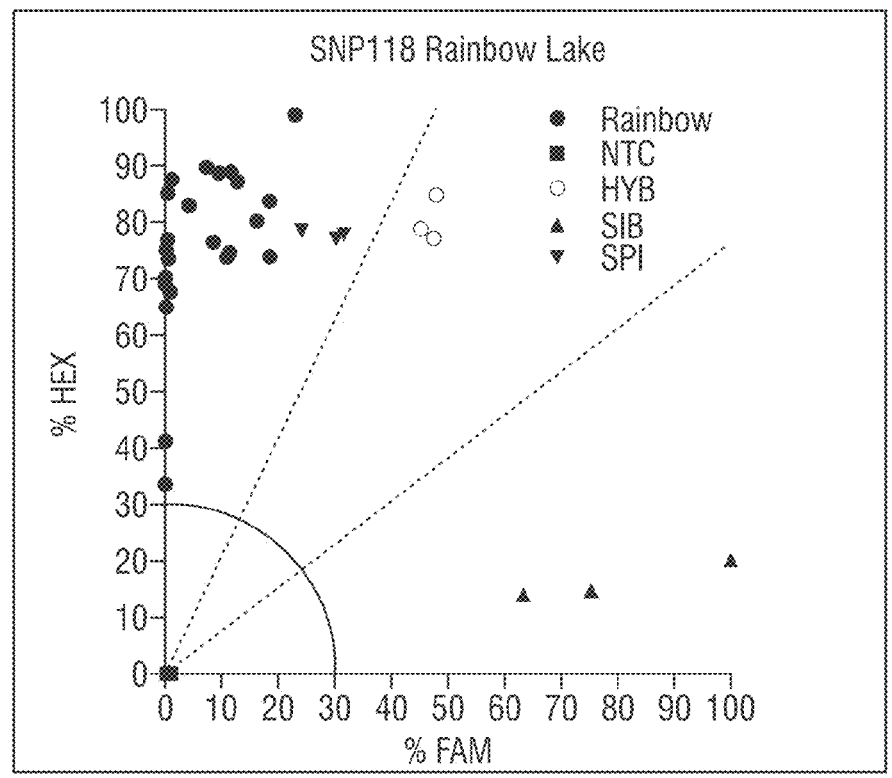
FIGS. 4A-F are graphs showing KASP assays for SNPs 118, 363, and 478 from wild collections of unknown watermilfoil individuals from Rainbow Lake (A, B, C) and Walleye Lake (D, E, F).
Figure 4B:
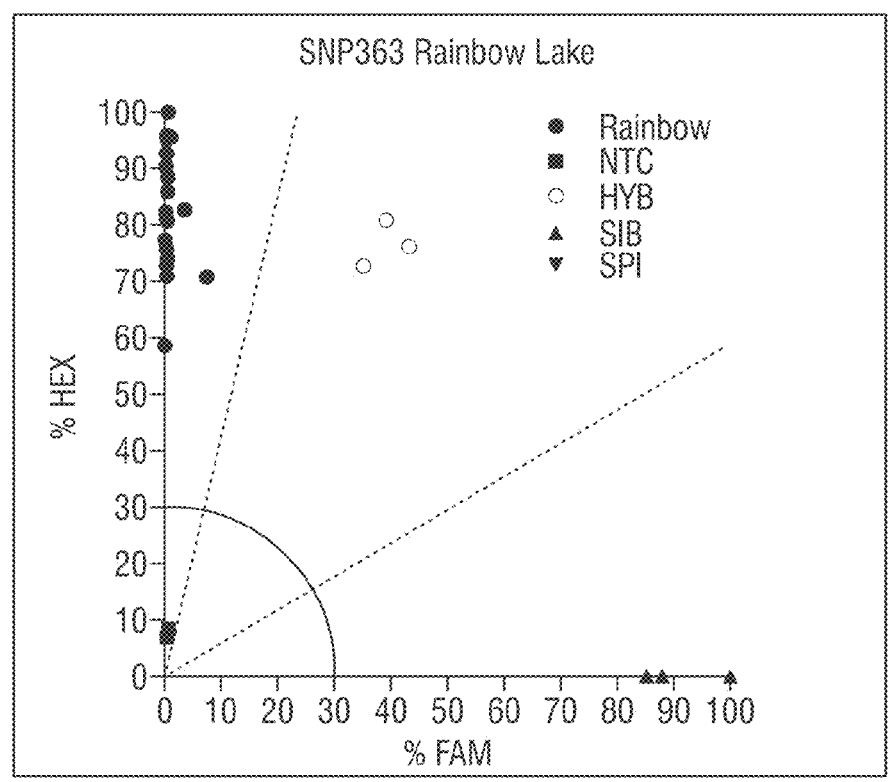
Figure 4C:
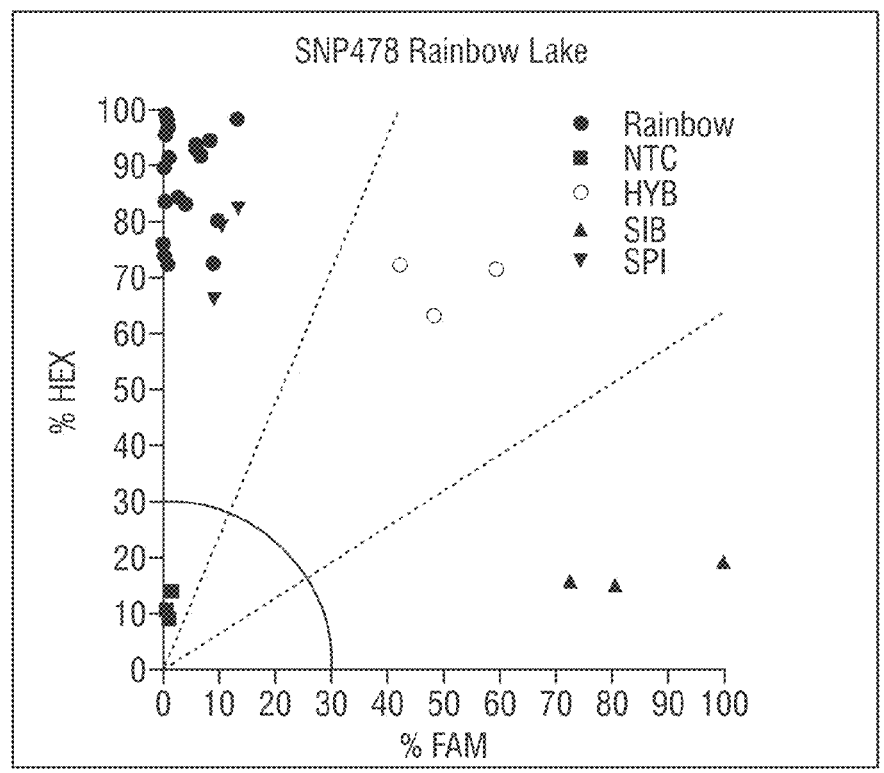

We also tested our assay on individuals from two lakes in northern Colorado, Rainbow Lake (n=23) and Walleye Lake (n=16). For Rainbow Lake, all sampled individuals were the invasive *M. spicatum*, as the fluorescence signal from all three SNPs for each individual was predominantly the HEX wavelength (Table 3, FIGS. 4A, 4B, 4C).

TABLE 3

KASP SNP genotyping calls and predicted probability of accuracy for 23 unknown watermilfoil individuals from Rainbow Lake; *M. spicatum* (*M. spi*)

| | All three SNPs | | SNP 118 | | SNP 363 | | SNP 478 | |
|---|---|---|---|---|---|---|---|---|
| Sample | Call | Prob (Pred) | Call | Prob (Pred) | Call | Prob (Pred) | Call | Prob (Pred) |
| Plant 1 | *M. spi* | 1.00 | *M. spi* | 1.00 | *M. spi* | 1.00 | *M. spi* | 1.00 |
| Plant 2 | *M. spi* | 1.00 | *M. spi* | 1.00 | *M. spi* | 1.00 | *M. spi* | 1.00 |
| Plant 3 | *M. spi* | 1.00 | *M. spi* | 1.00 | *M. spi* | 1.00 | *M. spi* | 1.00 |
| Plant 4 | *M. spi* | 1.00 | *M. spi* | 1.00 | *M. spi* | 1.00 | *M. spi* | 1.00 |
| Plant 5 | *M. spi* | 1.00 | *M. spi* | 1.00 | *M. spi* | 1.00 | *M. spi* | 1.00 |
| Plant 6 | *M. spi* | 1.00 | *M. spi* | 1.00 | *M. spi* | 1.00 | *M. spi* | 1.00 |
| Plant 7 | *M. spi* | 1.00 | *M. spi* | 1.00 | *M. spi* | 1.00 | *M. spi* | 1.00 |
| Plant 8 | *M. spi* | 1.00 | *M. spi* | 1.00 | *M. spi* | 1.00 | *M. spi* | 1.00 |
| Plant 9 | *M. spi* | 1.00 | *M. spi* | 1.00 | *M. spi* | 1.00 | *M. spi* | 1.00 |
| Plant 10 | *M. spi* | 1.00 | *M. spi* | 1.00 | *M. spi* | 1.00 | *M. spi* | 1.00 |
| Plant 11 | *M. spi* | 1.00 | *M. spi* | 1.00 | *M. spi* | 1.00 | *M. spi* | 1.00 |
| Plant 12 | *M. spi* | 1.00 | *M. spi* | 1.00 | *M. spi* | 1.00 | *M. spi* | 1.00 |
| Plant 13 | *M. spi* | 1.00 | *M. spi* | 1.00 | *M. spi* | 1.00 | *M. spi* | 1.00 |
| Plant 14 | *M. spi* | 1.00 | *M. spi* | 1.00 | *M. spi* | 1.00 | *M. spi* | 1.00 |

TABLE 3-continued

KASP SNP genotyping calls and predicted probability of accuracy for 23 unknown watermilfoil individuals from Rainbow Lake; *M. spicatum* (*M. spi*)

| | All three SNPs | | SNP 118 | | SNP 363 | | SNP 478 | |
|---|---|---|---|---|---|---|---|---|
| Sample | Call | Prob (Pred) | Call | Prob (Pred) | Call | Prob (Pred) | Call | Prob (Pred) |
| Plant 15 | *M. spi* | 1.00 | *M. spi* | 1.00 | *M. spi* | 1.00 | *M. spi* | 1.00 |
| Plant 16 | *M. spi* | 1.00 | *M. spi* | 1.00 | *M. spi* | 1.00 | *M. spi* | 1.00 |
| Plant 17 | *M. spi* | 1.00 | *M. spi* | 0.98 | *M. spi* | 1.00 | *M. spi* | 1.00 |
| Plant 18 | *M. spi* | 1.00 | *M. spi* | 1.00 | *M. spi* | 1.00 | *M. spi* | 1.00 |
| Plant 19 | *M. spi* | 1.00 | *M. spi* | 1.00 | *M. spi* | 1.00 | *M. spi* | 1.00 |
| Plant 20 | *M. spi* | 1.00 | *M. spi* | 0.88 | *M. spi* | 1.00 | *M. spi* | 1.00 |
| Plant 21 | *M. spi* | 1.00 | *M. spi* | 1.00 | *M. spi* | 1.00 | *M. spi* | 1.00 |
| Plant 22 | *M. spi* | 1.00 | *M. spi* | 1.00 | *M. spi* | 1.00 | *M. spi* | 1.00 |
| Plant 23 | *M. spi* | 1.00 | *M. spi* | 0.085 | *M. spi* | 1.00 | *M. spi* | 1.00 |

Figure 4D:
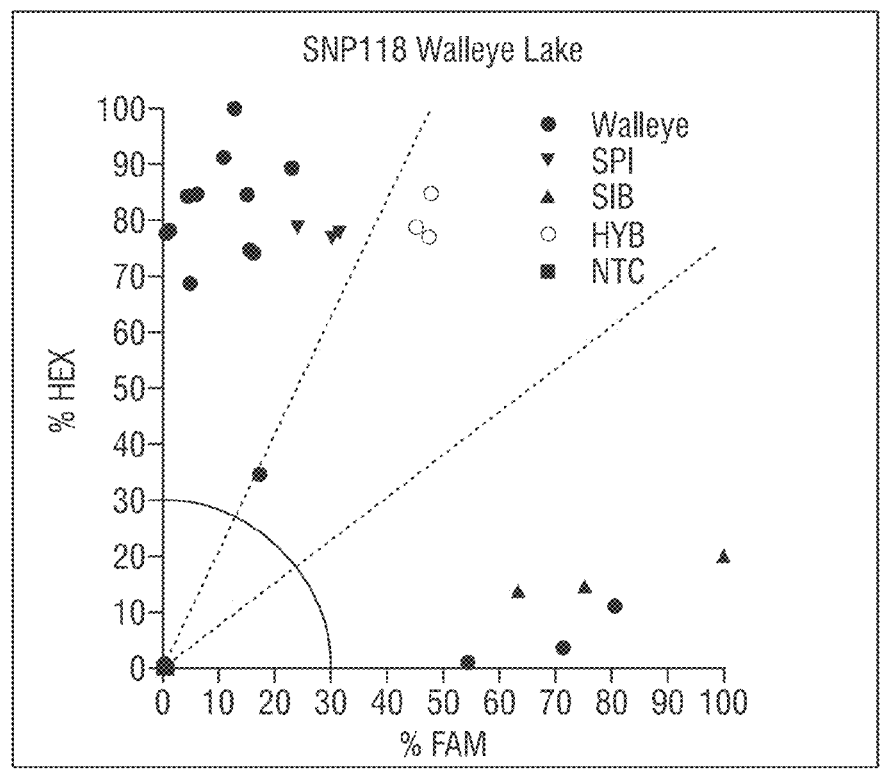
Figure 4E:
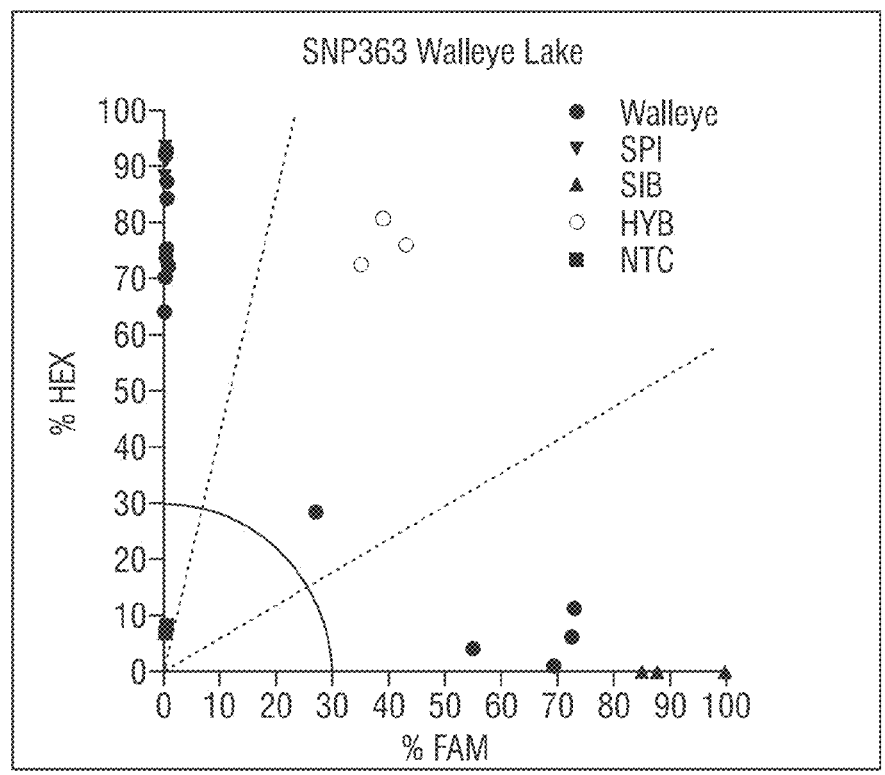
Figure 4F:
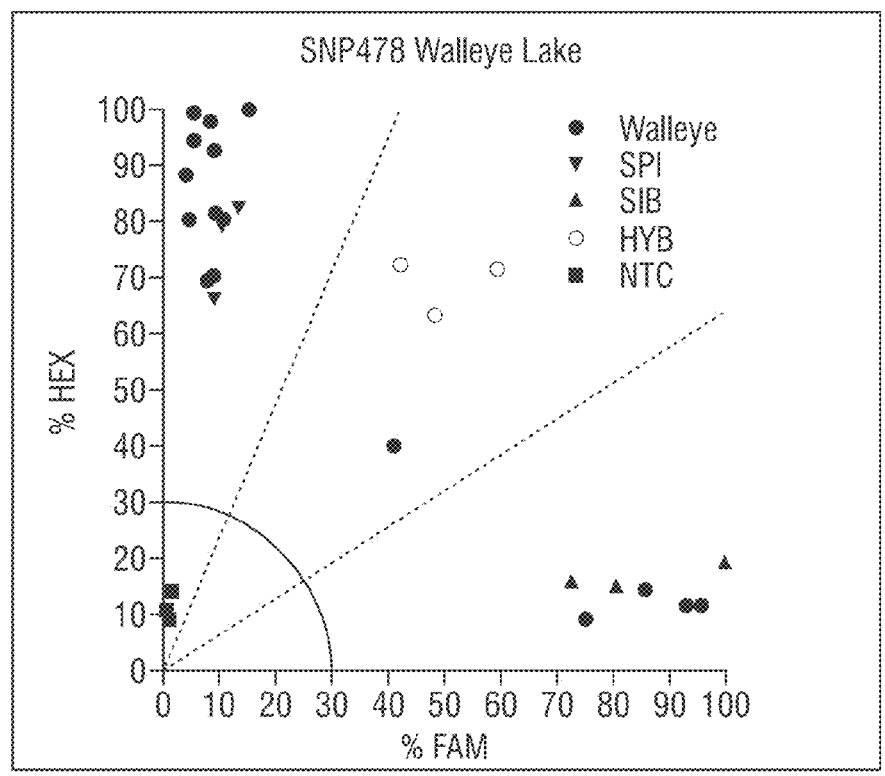

Walleye Lake, however, contained individuals of both *M. spicatum* and *M. sibiricum*, with 11 individuals showing predominantly HEX fluorescence and clustering with the *M. spicatum* plasmid controls, while four individuals (plants 2, 3, 8, and 12) showed predominantly FAM fluorescence and clustered with the *M. sibiricum* plasmid controls (Table 4, FIGS. 4D, 4E, 4F). Additionally, one individual (plant 1) had a hybrid genotype, as for all three SNPs it showed unambiguous dual HEX and FAM fluorescence and clustered with the artificial hybrid (Table 4, FIGS. 4D, 4E, 4F).

TABLE 4

KASP SNP genotyping calls and predicted probability of accuracy for 16 unknown watermilfoil individuals from Walleye Lake. *M. spicatum* (*M. spi*,); inter-specific hybrid (*M. spicatum* × *M. sibiricum*, Hyb,); *M. sibiricum* (*M. sib*,).

| | All three SNPs | | SNP 118 | | SNP 363 | | SNP 478 | |
|---|---|---|---|---|---|---|---|---|
| Sample | Call | Prob (Pred) | Call | Prob (Pred) | Call | Prob (Pred) | Call | Prob (Pred) |
| Plant 1 | Hyb | 1.00 | Hyb | 0.49 | Hyb | 1.00 | Hyb | 1.00 |
| Plant 2 | *M. sib* | 1.00 | *M. sib* | 1.00 | *M. sib* | 1.00 | *M. sib* | 1.00 |
| Plant 3 | *M. sib* | 1.00 | *M. sib* | 1.00 | *M. sib* | 1.00 | *M. sib* | 1.00 |
| Plant 4 | *M. spi* | 1.00 | *M. spi* | 1.00 | *M. spi* | 1.00 | *M. spi* | 1.00 |
| Plant 5 | *M. spi* | 1.00 | *M. spi* | 1.00 | *M. spi* | 1.00 | *M. spi* | 1.00 |
| Plant 6 | *M. spi* | 1.00 | *M. spi* | 1.00 | *M. spi* | 1.00 | *M. spi* | 1.00 |
| Plant 7 | *M. spi* | 1.00 | *M. spi* | 1.00 | *M. spi* | 1.00 | *M. spi* | 1.00 |
| Plant 8 | *M. sib* | 1.00 | *M. sib* | 1.00 | *M. sib* | 1.00 | *M. sib* | 1.00 |
| Plant 9 | *M. spi* | 1.00 | *M. spi* | 1.00 | *M. spi* | 1.00 | *M. spi* | 1.00 |
| Plant 10 | *M. spi* | 1.00 | *M. spi* | 1.00 | *M. spi* | 1.00 | *M. spi* | 1.00 |
| Plant 11 | *M. spi* | 1.00 | *M. spi* | 0.99 | *M. spi* | 1.00 | *M. spi* | 1.00 |
| Plant 12 | *M. sib* | 1.00 | *M. sib* | 1.00 | *M. sib* | 1.00 | *M. sib* | 1.00 |
| Plant 13 | *M. spi* | 1.00 | *M. spi* | 1.00 | *M. spi* | 1.00 | *M. spi* | 1.00 |
| Plant 14 | *M. spi* | 1.00 | *M. spi* | 1.00 | *M. spi* | 1.00 | *M. spi* | 1.00 |
| Plant 15 | *M. spi* | 1.00 | *M. spi* | 1.00 | *M. spi* | 1.00 | *M. spi* | 1.00 |
| Plant 16 | *M. spi* | 1.00 | *M. spi* | 0.99 | *M. spi* | 1.00 | *M. spi* | 1.00 |

Discriminant analysis again verified the accuracy of the genotyping calls, with a few individuals having a lower-confidence genotype from SNP 118 (plants 20 and 23 from Rainbow Lake and plant 1 from Walleye Lake) but 100% probability of a correct call when data from all three SNPs were considered simultaneously. Both SNP 118 and SNP 478 used one degenerate base each. The calls for SNP 478 were much more accurate than for SNP 118, possibly due to the distribution of the two degenerate base within the respective forward primer. The degenerate bases in each case were for SNPs that distinguish between different sub-populations of *M. sibiricum*.

Example 2

This process will allow the seed certification industry to reliably assess bulked *Amaranthus* seed samples as containing Palmer amaranth or not and to assess bulked *Amaranthus* seed samples as containing waterhemp or not. Several *Amaranthus* species are very common and are not prohibited noxious weeds (e.g., redroot pigweed, smooth pigweed, etc.), and seeds of the various *Amaranthus* species (Table 5) cannot be reliably visually identified. This invention describes a DNA genotyping method to detect either Palmer amaranth or waterhemp in a mixture of bulked *Amaranthus* seeds.

TABLE 5

*Amaranthus* species included in the diagnostic assay.

| Scientific Name | Common Name |
|---|---|
| *Amaranthus palmeri* | Palmer amaranth |
| *Amaranthus spinosus* | Spiny amaranth |
| *Amaranthus albus* | Prostrate pigweed |
| *Amaranthus blitoides* | Mat amaranth |
| *Amaranthus arenicola* | Sandhill amaranth |

TABLE 5-continued

Amaranthus species included in the diagnostic assay.

| Scientific Name | Common Name |
|---|---|
| Amaranthus tuberculatus (syn. A. rudis) | Waterhemp (syn. Common waterhemp, tall waterhemp) |
| Amaranthus hybridus | Smooth pigweed |
| Amaranthus powellii | Powell amaranth |
| Amaranthus retroflexus | Redroot pigweed |

Methods:

DNA is extracted from *Amaranthus* seeds using a standard CTAB DNA extraction protocol (see description, supra. Due to the presence of phenols and other compounds in seeds which may inhibit PCR, the DNA samples are further purified using a OneStep PCR Inhibitor Removal Kit (Zymo Research). DNA may also be extracted using any commercially available kits, such as Qiagen DNEasy.

The Internal Transcribed Spacer (ITS) region in *Amaranthus* species contains sequence polymorphisms that enable the identification of each of nine *Amaranthus* species. Single nucleotide polymorphisms (SNPs) can be quickly genotyped using the KASP marker system. An alignment of nine *Amaranthus* species (*A. palmeri, A. spinosus, A. albus, A. blitoides, A. arenicola, A. tuberculatus, A. hybridus, A. powellii,* and *A. retroflexus*) (FIG. 5) shows where SNPs occur among the species. FIG. 5A indicates (with ^^) where a double SNP (two consecutive nucleotides) differentiates *A. palmeri* from the other eight species (Table 6; see FIG. 6 for entire ITS alignment). Table 7 lists the *A. palmeri* specific forward primer used in a KASP assay to amplify this specific sequence, along with the forward primer that amplifies the other eight species and the universal reverse primer.

FIG. 5B indicates with a single ^ where *A. tuberculatus* can be distinguished from seven other common *Amaranthus* species (Table 6). FIG. 6 shows the ITS alignment across the species. *A. arenicola* is a rarer species that is closely related to *A. tuberculatus* and cannot be distinguished using the ITS sequence (SEQ ID NO: 17-25). *A. tuberculatus* is much more likely to be present in a native plant seed sample than *A. arenicola*. Table 7 lists the *A. tuberculatus* specific forward primer used in a KASP assay to amplify this specific sequence, along with the forward primer that amplifies the other seven species and the universal reverse primer.

Additionally, a SNP in the acetolactate synthase (ALS) gene enables identification of waterhemp from Palmer amaranth, spiny amaranth, Powell amaranth, and redroot pigweed (See FIG. 8 for alignment of ALS sequence among five species, SEQ ID NO: 26-30). The primers for this KASP assay are listed in Table 8.

The PCR protocol for both ITS assays is conducted on a real-time thermal cycler as follows: Touch down for ten cycles, (each cycle includes 94 C for 30 sec, followed by annealing and amplification at 63 C for 30 sec, dropping 0.6 C per cycle). The protocol then includes 24 cycles of 94 C for 30 sec and 57 C for 60 sec. The fluorescence in the plate is recorded after each cycle, and data from the last cycle are used for species identification.

TABLE 6

Polymorphic regions in ITS used to identify Amaranthus species.
Bold indicates common sequence for diagnostic, fluoresence labeled
primer, polymorphic sequence shown in parentheses, italics
indicates universal sequence for primer used to amplify all
sequences.

| Assay | Sequence |
|---|---|
| Palmer amaranth identification in bulk | CCGGGCGTGGATGGCCTAAAA(AG/CA)GGAGCCCGCGGTTTCGA*GCTGC TGCGGCGATTGGTGGTGTGCAAGGCCTAGCCTAGAATGCAATCGCGTCG* SEQ ID NOT: 31 |
| Waterhemp identification in bulk | GGTCTGCGCCAAGGA*A*CATGAACTTGAGCGTGCTCGTCTTGTGCCCGGGT CACCGGCGCATGGGAGTGGATGCACCCAATATTGAGTATT(G/A)AACGA CTCTCGGCAACGGAT*ATCTTGGCT* SEQ ID NO: 32 |

TABLE 7

Primers used in the Amaranthus species identification assay.

| Assay | Primer ID | Sequence | Label |
|---|---|---|---|
| Palmer amaranth identification in bulk | >Amaranth_Palmer_ITS_FP_FAM | GAAGGTGACCAAGTTCATGCTCGG GCGTGGATGGCCTAAAAAG SEQ ID NO: 33 | FAM |
| | >Amaranth_Others_ITS_FP_HEX | GAAGGTCGGAGTCAACGGATTCGG GCGTGGATGGCCTAAAACA SEQ ID NO: 34 | HEX |
| | >Amaranth_Universal_ITS_RP | *ACCAATCGCCGCAGCAGC* SEQ ID NO: 35 | N/A |
| Waterhemp identification in bulk | >Ama_Tu/AREN_ITS269_FP_FAM | GAAGGTGACCAAGTTCATGCTATC CGTTGCCGAGAGTCGTTC SEQ ID NO: 36 | FAM |

TABLE 7-continued

Primers used in the Amaranthus species identification assay.

| Assay | Primer ID | Sequence | Label |
|---|---|---|---|
| | >Ama_Others_ITS269_FP_HEX | GAAGGTCGGAGTCAACGGATTATC CGTTGCCGAGAGTCGTTT<br>SEQ ID NO: 37 | HEX |
| | >Ama_Universal_ITS269_RP | ACATGAACTTGAGCGTGCTCGTC<br>SEQ ID NO: 38 | |

TABLE 8

Primers used KASP on ALS sequences to differentiate waterhemp from other species including Palmer amaranth. The sequence specific to waterhemp (AMATA) and other Amaranthus species (denoted by AMAPA) is indicated by underlining.

| Assay | Primer ID | Sequence | Label |
|---|---|---|---|
| Waterhemp identification in bulk | AMATA_ALS_KASP_SNP_FAM | GAAGGTGACCAAGTTCATGCT<u>AAA AAGAAAGCTTCCTTAACAATTCTA GGG</u><br>SEQ ID NO: 39 | FAM |
| | AMAPA_ALS_KASP_SNP_HEX | GAAGGTCGGAGTCAACGGATT<u>AAA AAGAAAGCTTCCTTAACAATTCTA GGA</u><br>SEQ ID NO: 40 | HEX |
| | AMAPA_ALS_KASP_RP | GTTGAGGTAACTCGATC(A/C)ATTA CTAAGC<br>SEQ ID NO: 41 | N/A |

Figure 9:
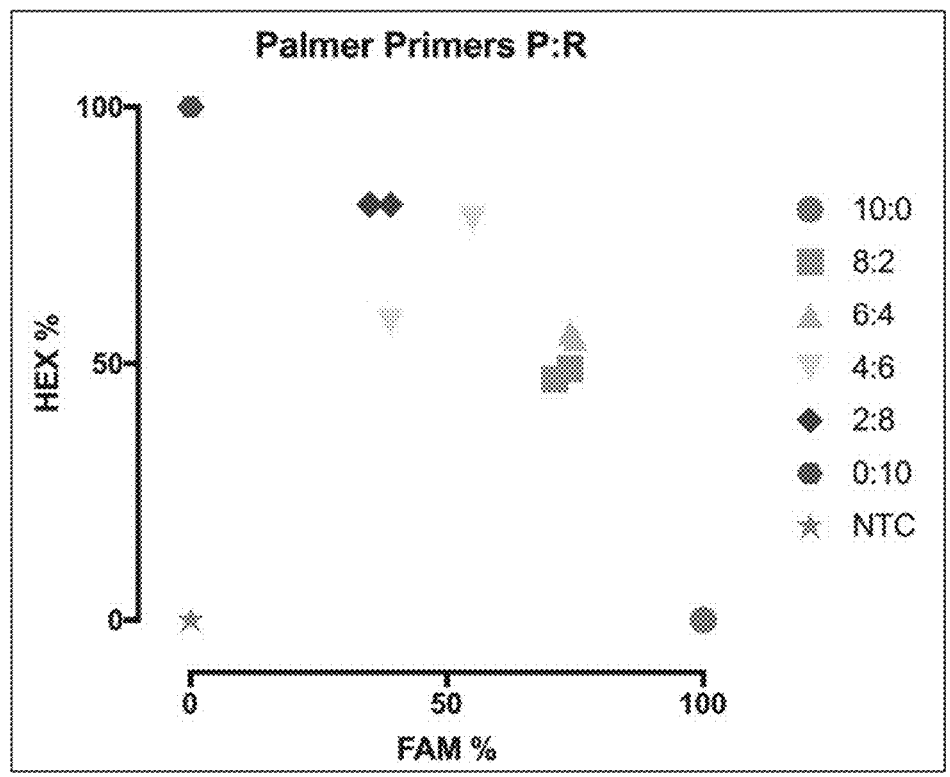
FIG. 9 is a graph showing results of an assay where Palmer amaranth is identified with a FAM forward primer and all other *Amaranthus* species identified with forward primer HEX. NTC refers to no template controls.
Figure 10:
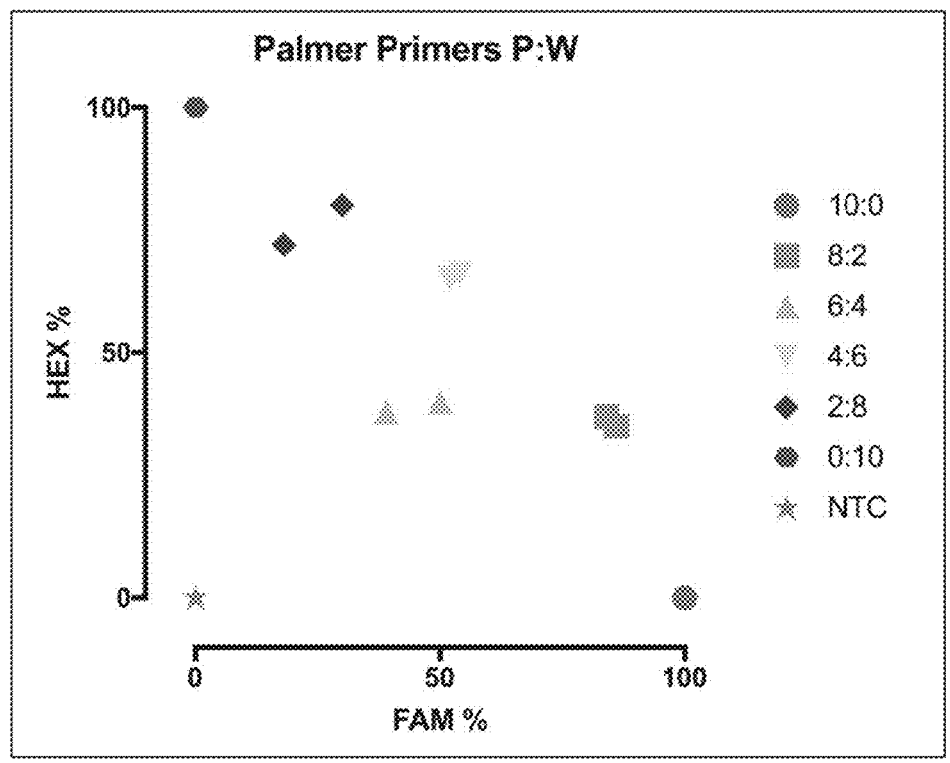
FIG. 10 is a graph showing results of an assay where Palmer amaranth is identified with a FAM forward primer and all other *Amaranthus* species identified with forward primer HEX. NTC refers to no template controls.

Results:

FIG. 9 is a graph showing results with the Palmer amaranth forward primer (FAM) and all other *Amaranthus* species forward primer (HEX). In this case, Palmer amaranth seeds were mixed with redroot pigweed in ratios of 10:0, 8:2, 6:4, 4:6, 2:8, and 0:10 to test for specificity between these two species. No template controls (NTC) were included to control for non-specific fluorescence in the assay. The assay is able to identify 1 Palmer amaranth seed in a mixture of 4 total seeds (see 2:8 mixture ratio). FIG. 10 shows results with Palmer amaranth forward primer (FAM) and all other *Amaranthus* species forward primer (HEX). Palmer amaranth seeds were mixed with waterhemp in ratios of 10:0, 8:2, 6:4, 4:6, 2:8, and 0:10 to test for specificity between these two species. No template controls (NTC) were included to control for non-specific fluorescence in the assay. The assay is able to identify 1 Palmer amaranth seed in a mixture of 4 total seeds (see 2:8 mixture ratio).

Figure 11:
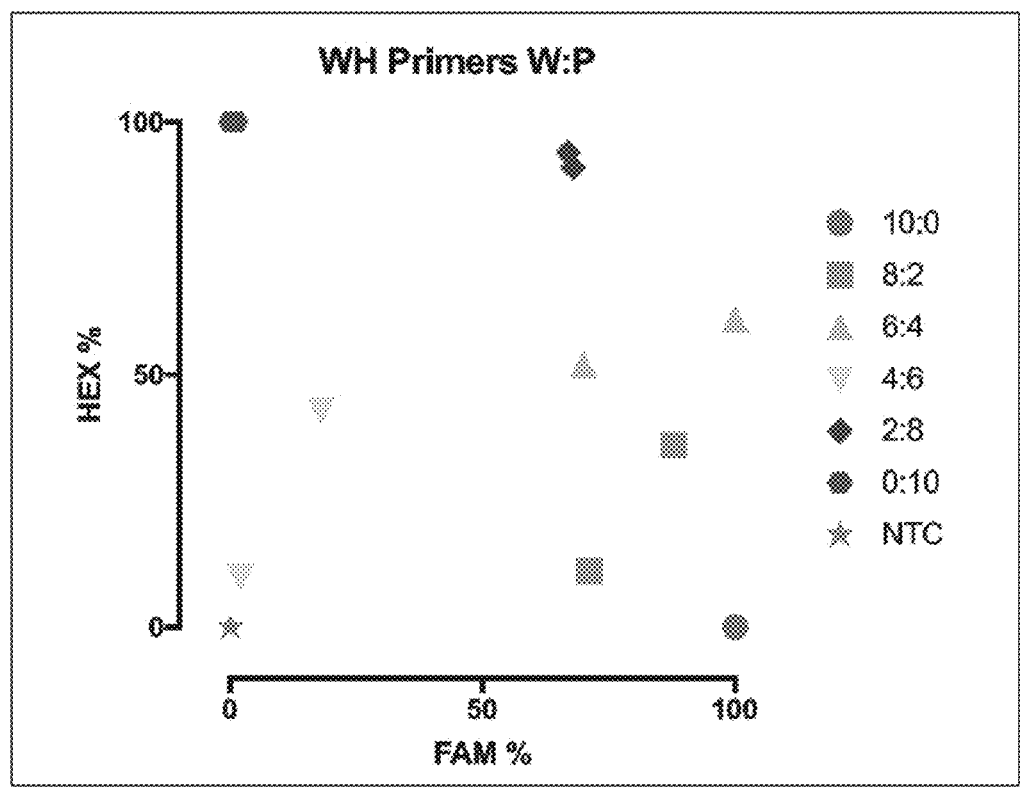
FIG. 11 is a graph showing results of an assay where waterhemp is identified with forward primer FAM and all other *Amaranthus* species identified by forward primer HEX. NTC refers to no template controls.
Figure 12:
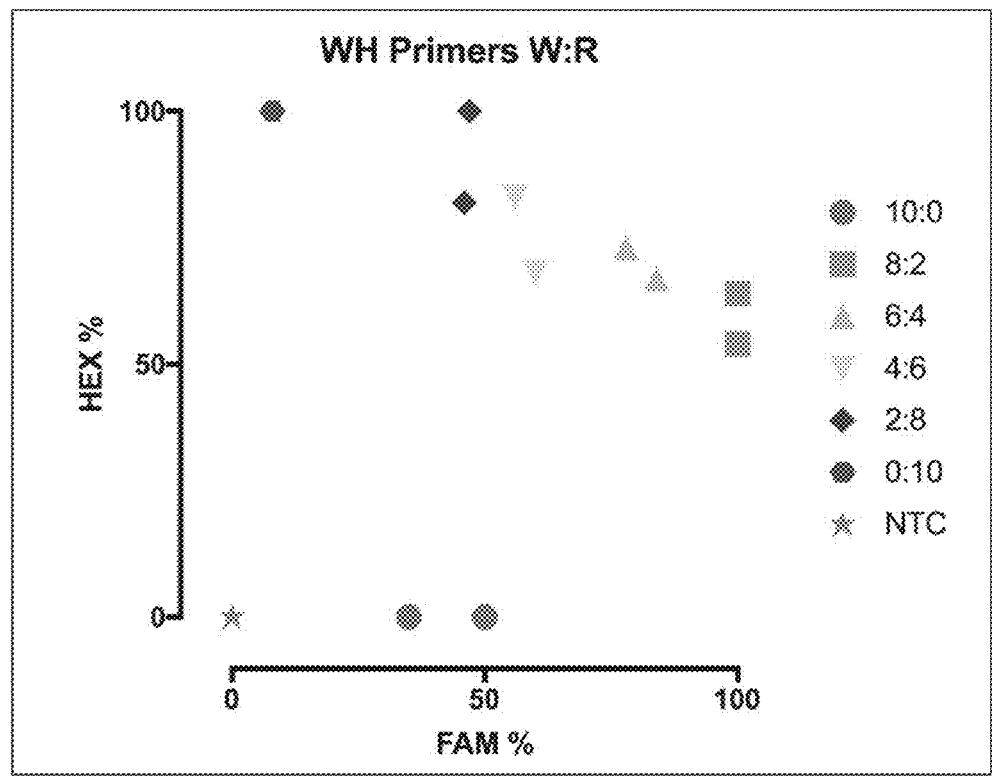
FIG. 12 is a graph showing results of an assay where waterhemp is identified with forward primer FAM and all other *Amaranthus* species identified by forward primer HEX. NTC refers to no template controls.

FIG. 11 shows waterhemp forward primer (FAM) and all other *Amaranthus* species forward primer (HEX). Waterhemp seeds were mixed with Palmer amaranth in ratios of 10:0, 8:2, 6:4, 4:6, 2:8, and 0:10 to test for specificity between these two species. No template controls (NTC) were included to control for non-specific fluorescence in the assay. The assay is able to identify 1 waterhemp seed in a mixture of 4 total seeds (see 2:8 mixture ratio). One data point is missing. In FIG. 12 results are shown with waterhemp forward primer (FAM) and all other *Amaranthus* species forward primer (HEX). Waterhemp seeds were mixed with redroot pigweed in ratios of 10:0, 8:2, 6:4, 4:6, 2:8, and 0:10 to test for specificity between these two species. No template controls (NTC) were included to control for non-specific fluorescence in the assay. The assay is able to identify 1 waterhemp seed in a mixture of 4 total seeds (see 2:8 mixture ratio).

As can be seen, the KASP assay for the ITS region can detect at a minimum one Palmer amaranth seed in a mixture of five total seeds (FIGS. 9 and 10), and one waterhemp seed in a mixture of five total seeds (FIGS. 11 and 12). This assay enables reliable assessment of an *Amaranthus* seed mixture as to whether or not it contains the species of interest, Palmer amaranth or waterhemp.

Figure 13:
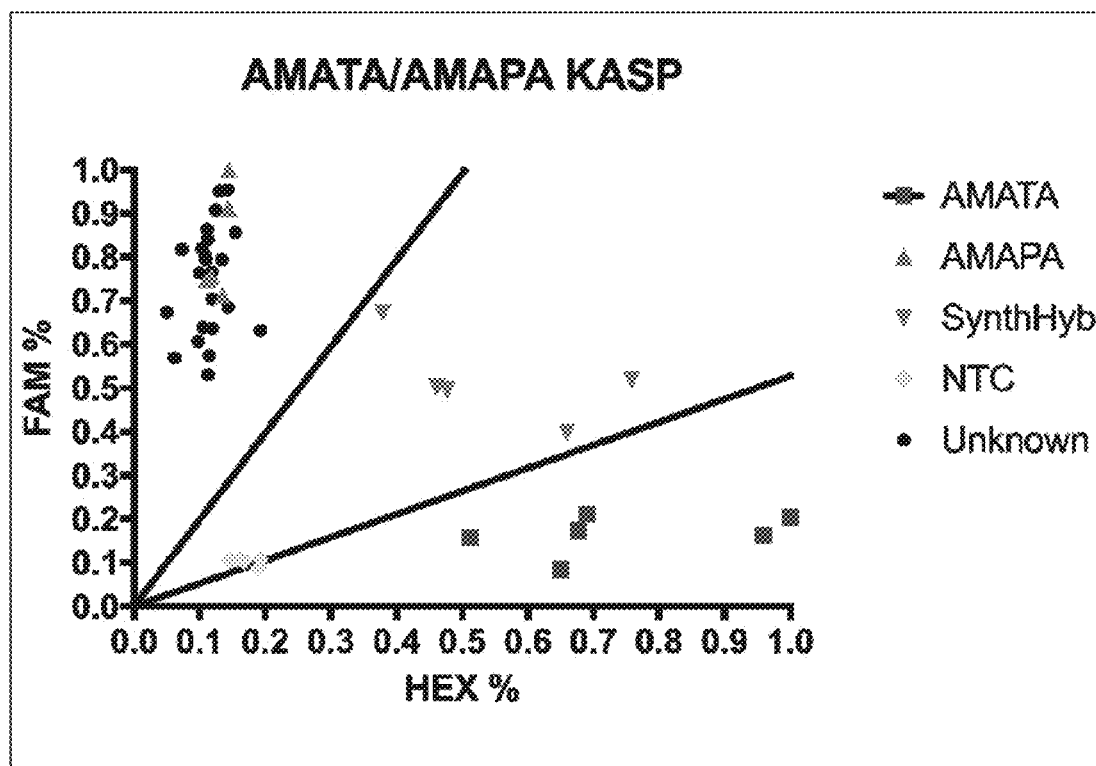
FIG. 13 is a graph showing a KASP assay for the ALS SNP differentiating waterhemp from Palmer amaranth NTC refers to no template controls (NTC).

The KASP assay for the ALS SNP can accurately differentiate waterhemp from Palmer amaranth (FIG. 13), and this assay can also be used to differentiate waterhemp in a mixture with spiny amaranth, Powell amaranth, and redroot pigweed. Synthetic hybrids were created by mixing Palmer and waterhemp DNA in a 50:50 mixture. A KASP assay with a waterhemp forward primer (HEX, AMATA) and a Palmer amaranth forward primer (FAM, AMAPA) was used to identify samples including known waterhemp, known Palmer amaranth, synthetic hybrids, and unknown samples (shown to be Palmer amaranth). No template controls (NTC) were included to control for non-specific fluorescence in the assay.

LITERATURE CITED

Berger S T, Netherland M D, MacDonald G E (2015) Laboratory documentation of multiple-herbicide tolerance to fluridone, norflurazon, and topramazone in a hybrid watermilfoil (*Myriophyllum spicatum*×*M. sibiricum*) population. Weed Sci 63:235-241.

Coffey B T, McNabb C D (1974) Eurasian water-milfoil in Michigan. Mich Bot 13:159-165.

Couch R, Nelson E (1988) *Myriophyllum quitense* (Haloragaceae) in the United States. Brittonia 40:85-88.

Doyle J (1991) DNA protocols for plants—CTAB total DNA isolation. In 'Molecular techniques in taxonomy'. (Eds G M Hewitt, A Johnston) pp. 283-293 Springer: Berlin.

Eiswerth M E, Donaldson S G, Johnson W S (2000) Potential environmental impacts and economic damages of Eurasian watermilfoil (*Myriophyllum spicatum*) in Western Nevada and Northeastern California. Weed Technol 14:511-518.

Grafe S F, Boutin C, Pick F R, Bull R D (2014) A PCR-RFLP method to detect hybridization between the invasive Eurasian watermilfoil (*Myriophyllum spicatum*) and the native northern watermilfoil (*Myriophyllum sibiricum*), and its application in Ontario lakes. Botany 93:117-121.

Hovick S M, Whitney K D (2014) Hybridisation is associated with increased fecundity and size in invasive taxa: meta-analytic support for the hybridisation-invasion hypothesis. Ecol Lett 17:1464-1477.

LaRue E A, Zuellig M P, Netherland M D, Heilman M A, Thum R A (2013) Hybrid watermilfoil lineages are more invasive and less sensitive to a commonly used herbicide than their exotic parent (Eurasian watermilfoil). Evol Appl 6:462-471.

Madsen J D, Sutherland J, Bloomfield J, Eichler L, Boylen C (1991) The decline of native vegetation under dense Eurasian watermilfoil canopies. J Aquatic Plant Mgmt 29:94-99.

Moody M, Les D (2007) Geographic distribution and genotypic composition of invasive hybrid watermilfoil (*Myriophyllum spicatum*×*M. sibiricum*) populations in North America. Biol Inv 9:559-570.

Moody M L, Les D H (2002) Evidence of hybridity in invasive watermilfoil (*Myriophyllum*) populations. Proc Natl Acad Sci USA 99:14867-14871.

Moody M L, Palomino N, Weyl P S, Coetzee J A, Newman R M, Harms N E, Liu X, Thum R A (2016) Unraveling the biogeographic origins of the Eurasian watermilfoil (*Myriophyllum spicatum*) invasion in North America. Am J Bot 103:709-718.

Olden J D, Tamayo M (2014) Incentivizing the public to support invasive species management: Eurasian milfoil reduces lakefront property values. PloS one 9:e110458.

Semagn K, Babu R, Hearne S, Olsen M (2014) Single nucleotide polymorphism genotyping using Kompetitive Allele Specific PCR (KASP): overview of the technology and its application in crop improvement. Mol Breeding 33:1-14.

Sturtevant A P, Hatley N, Pullman G, Sheick R, Shorez D, Bordine A, Mausolf R, Lewis A, Sutter R, Mortimer A (2009) Molecular characterization of Eurasian watermilfoil, northern milfoil, and the invasive interspecific hybrid in Michigan lakes. J Aquatic Plant Mgmt 47:128.

Zuellig M P, Thum R A (2012) Multiple introductions of invasive Eurasian watermilfoil and recurrent hybridization with northern watermilfoil in North America. J Aquatic Plant Mgmt 50:1-19.

---

What is claimed is:

1. A process for determining the genotype of a population of *Myriophyllum* plants, plant parts, or seeds, the process comprising,
   a) providing a first primer set comprising,
      (i) a first primer recognizing a first target nucleotide sequence in the genome of said *Myriophyllum* specific to *Myriophyllum spicatum* and further comprising a first reporter sequence;
      (ii) a second primer recognizing a second target nucleotide sequence in the genome of said *Myriophyllum* specific to *Myriophyllum sibiricum* and further comprising a second reporter sequence; and
      (iii) a third primer recognizing a third target nucleotide sequence in the genome of both *Myriophyllum spicatum* and *Myriophyllum sibiricum*;
   b) providing a cassette comprising sequences complementary to said first and second reporter sequences which when bound to said first or second primer releases a first or second reporter molecule;
   c) obtaining samples comprising DNA from a plurality of plants in said population of *Myriophyllum* plants;
   d) contacting said first primer set and said cassette with each of said samples under conditions such that said primers bind to and amplify any of said nucleotide sequences in said samples recognized by said primers, and when bound to said recognized nucleotide sequence results in said reporter molecule generating a measurable signal; and
   e) detecting the presence or absence of measurable signal and determining if said sample DNA in each of said samples comprises DNA of said *Myriophyllum spicatum*, *Myriophyllum sibiricum*, or a hybrid of said *Myriophyllum spicatum* and *Myriophyllum sibiricum* to determine the genotype of said population.

2. The method of claim 1, wherein said process is repeated with a second and third primer set, each of said first, second, and third primer sets different from each other, combining the results of said measurable signals obtained from said first, second and third primer sets together and identifying samples in which the same measurable signal is detected in all three primer sets to determine the genotype of said population.

3. The method of claim 1, further comprising transforming at least one *E. coli* with a plasmid comprising said first target nucleotide sequence and a second *E. coli* with a plasmid comprising said second target sequence and extracting said plasmids from said *E. coli*, producing a first control plasmid comprising said first target sequence, a second control plasmid comprising said second target sequence and a third control plasmid mixture comprising a 1:1 mixture of plasmids of said first and second control target sequence, contacting said control plasmids with said primers and cassette and comparing measurable signal of said control plasmids to measurable signal produced from said samples.

4. The method of claim 1, further comprising selecting a method of controlling plants of said population that reduces growth of a higher number of said hybrid and/or *Myriophyllum spicatum* plants than when said hybrid plants and/or *Myriophyllum spicatum* plants are not detected.

5. The method of claim 1, further comprising increasing the application rate of herbicide and/or changing said herbicide applied to said population of *Myriophyllum* when said population comprises hybrid and/or *Myriophyllum spicatum* plants.

6. The method of claim 1, wherein said target region comprises at least one sequence within the nuclear ribosomal internal transcribed spacer region of said *Myriophyllum* genome.

7. A process for determining the genotype of a population of plants, plant parts or plant tissue, the process comprising
   a) providing a first primer set comprising,
      (i) a first primer recognizing a first target nucleotide sequence in the genome of a plant genus specific to a first species and further comprising a first reporter sequence;
      (ii) a second primer recognizing a second target nucleotide sequence in the genome of said plant genus specific to a second species or group of species and further comprising a second reporter sequence; and
      (iii) a third primer recognizing a third target nucleotide sequence in the genome of both said first and second species;
   b) providing a cassette comprising sequences complementary to said first and second reporter sequences which when bound said first or second primer releases a first or second reporter molecule;
   c) obtaining samples comprising DNA from said plurality of plants, plant parts or plant tissue in said population;
   d) contacting said fi primer set and said cassette with said samples under conditions such that said primers bind to and amplify any of said nucleotide sequences in said samples recognized by said primers, and when bound to said recognized nucleotide sequence results in said reporter molecule generating a measurable signal; and
   e) detecting the presence or absence of measurable signal and determining if said sample DNA in each of said samples comprises DNA of said first species, second species, or a hybrid of said first and second species to determine the genotype of said population.

8. The method of claim 7, wherein said process is repeated with a second and third primer sets, each of said first, second and third primer sets different from each other and identifying samples combining the results of said measurable signals obtained from said first, second and third primer sets together and identifying samples in which the same measurable signal is detected in all three primer sets to determine the genotype of said population.

9. The method of claim 7, further comprising transforming at least one *E. coli* with a plasmid comprising said first target nucleotide sequence and a plasmid comprising said second target sequence and extracting said plasmids of said first and second target sequences from said *E. coli*, producing a first control plasmid comprising said first target sequence, a second control plasmid comprising said second target sequence and a third control plasmid mixture comprising a 1:1 mixture of plasmids comprising said first and second control target sequence, contacting said control plasmids with said primers and cassette and comparing measurable signal of said control plasmids to measurable signal produced from said samples.

10. The method of claim 7, wherein at least one of said species is a weed species, and further comprising selecting a method of controlling plants of said population that reduces growth of a higher number of said hybrid and/or weed species plants than when said hybrid plants and/or said weed species plants are not detected.

11. The method of claim 7, wherein at least one of said species is a weed species and further comprising increasing the application rate of herbicide and/or changing the herbicide applied to said population of plants when said population comprises hybrid plants and/or weed species plants.

12. The method of claim 7, wherein said first species is selected from *Amaranthus palmeri* (*A. palmeri*) or *Amaranthus tuberculatus* (*A. tuberculatus*) and said second group of species comprises *Amaranthus* species other than *A. palmeri* where said first species is *A. palmeri*, or *Amaranthus* species other than *A. tuberculatus* where said first species is *A. tuberculatus*, and determining if said population of plants or seed 13 comprises *A. palmeri* or *A. tuberculatus*.

13. The method of claim 7, wherein said first species is selected from *Myriophyllum spicatum* or *Amaranthus palmeri* and said second species is selected from *Myriophyllum sibiricum* or *Amaranthus tuberculatus*.

14. A method of controlling a population of plants, said method comprising,
  a) determining genotype of said population comprising,
    (i) providing a first primer set comprising,
      (a) a first primer recognizing a first target nucleotide sequence in the genome of a plant genus specific to a first species and further comprising a first reporter sequence;
      (b) a second primer recognizing a second target nucleotide sequence in the genome of said plant genus specific to a second species and further comprising a second reporter sequence; and
      (c) a third primer recognizing a third target nucleotide sequence in the genome of both said first and second species;
    (ii) providing a cassette comprising sequences complementary to said first and second reporter sequences which when bound to said first or second primer releases a first or second reporter molecule;
    (iii) obtaining samples comprising DNA from a plurality of plants in said population of plants;
    (iv) contacting said first primer set and said cassette with said samples under conditions such that said primers bind to and amplify any of said nucleotide sequences in said samples recognized by said primers, and when bound to said recognized nucleotide sequence results in said reporter molecule generating a measurable signal; and
    (v) detecting the presence or absence of measurable signal and determining if said sample DNA in of said samples comprises DNA of said first species, second species, or a hybrid of said first and second species to determine the genotype of said population; and
  b) determining if said population has hybrid plants and/or plants that are a weed species and when said hybrid and/or weed species are present in said population, selecting a method of controlling plants of said population that reduces growth of a higher number of said hybrid and/or weed species plants than when said hybrid plants and/or weed species plants are not present.

15. The method of claim 14, further comprising determining if there are more hybrid plants than non-hybrid plants and/or more weed species plants than non-weed species plants in said population.

16. The method of claim 14, wherein said method of control comprises application of herbicide and increasing application of said herbicide and/or selection of said herbicide that controls said hybrid and/or weed species where said hybrid and/or weed species are detected.

17. The method of claim 14, wherein said first species is selected from *Amaranthus palmeri* (*A. palmeri*) or *Amaranthus tuberculatus* (*A. tuberculatus*) and said second group of species comprises *Amaranthus* species other than *A. palmeri* where said first species is *A. palmeri* or *Amaranthus* species other than *A. tuberculatus* where said first species is *A. tuberculatus* and determining if said population of plants or seed comprises *A. palmeri* or *A. tuberculatus*.

18. The method of claim 14, wherein said first species is selected from *Myriophyllum spicatum* or *Amaranthus palmeri* and said second species is selected from *Myriophyllum sibiricum* or *Amaranthus tuberculatus*.

19. The method of claim 1, further comprising selecting said first, second and third target species that, when present in a plant, are co-inherited.

20. The method of claim 1, wherein said genotype of said population is determined by converting said measurable signal to a data point and conducting linear discriminant analysis to determine the genotype of said population.

21. The method of claim 7, wherein said genotype of said population is determined by converting said measurable signal to a data point and conducting linear discriminant analysis to determine the genotype of said population.

22. The method of claim 14, wherein said genotype of said population is determined by converting said measurable signal to a data point and conducting linear discriminant analysis to determine the genotype of said population.

23. The method of claim 3, wherein said first target sequence comprises three single nucleotide polymorphisms (SNPs) of said *M. spicatum*, said second target sequence comprising three SNPs of said *M. sibiricum*.

* * * * *

UNITED STATES PATENT AND TRADEMARK OFFICE
CERTIFICATE OF CORRECTION

PATENT NO. : 9,963,750 B2  
APPLICATION NO. : 15/589172  
DATED : May 8, 2018  
INVENTOR(S) : Kallie C. Kessler et al.

Page 1 of 1

It is certified that error appears in the above-identified patent and that said Letters Patent is hereby corrected as shown below:

In Column 54, Claim 7, Line 55:
DELETE "fi" before primer
INSERT --first--

In Column 55, Claim 12, Line 38:
DELETE "13" after seed

In Column 56, Claim 14, Line 9:
INSERT --each-- between "in" and "of"

Signed and Sealed this
Twenty-eighth Day of August, 2018

Andrei Iancu
*Director of the United States Patent and Trademark Office*